(12) United States Patent
Grossman

(10) Patent No.: US 7,506,760 B2
(45) Date of Patent: Mar. 24, 2009

(54) PACKAGING AND DISPENSERS FOR ADHESIVE BACKED ELEMENTS

(76) Inventor: Victor A. Grossman, 91 Rupert Ave., Staten Island, NY (US) 10314

( * ) Notice: Subject to any disclaimer, the term of this patent is extended or adjusted under 35 U.S.C. 154(b) by 507 days.

(21) Appl. No.: 11/032,295

(22) Filed: Jan. 10, 2005

(65) Prior Publication Data

US 2006/0151347 A1    Jul. 13, 2006

(51) Int. Cl.
*A61B 19/02* (2006.01)
(52) U.S. Cl. .................. 206/440; 206/441; 602/57
(58) Field of Classification Search ............ 206/440, 206/441, 447, 469; 602/41, 42, 43, 57, 900, 602/904
See application file for complete search history.

(56) References Cited

U.S. PATENT DOCUMENTS

| | | | | |
|---|---|---|---|---|
| 2,946,435 A | * | 7/1960 | Schladermundt et al. | 206/441 |
| 2,973,859 A | * | 3/1961 | Schladermundt et al. | 206/441 |
| 3,072,249 A | * | 1/1963 | Tritsch | 206/441 |
| 3,612,265 A | * | 10/1971 | Dickerson | 206/441 |
| 3,835,992 A | | 9/1974 | Adams | 206/390 |
| 3,874,581 A | | 4/1975 | Fox et al. | 206/268 |
| 4,182,449 A | | 1/1980 | Lozlow | 206/441 |
| 4,304,333 A | * | 12/1981 | Kozlow, Sr. | 206/441 |
| 4,310,509 A | | 1/1982 | Berglund et al. | 424/448 |
| 4,323,557 A | | 4/1982 | Rosso et al. | 424/448 |
| 4,418,822 A | | 12/1983 | Dotta | 206/441 |
| 4,728,323 A | | 3/1988 | Matson | 604/304 |
| 4,781,293 A | | 11/1988 | Johns | 206/441 |
| 4,851,076 A | | 7/1989 | Manusch | 156/577 |
| 4,852,734 A | | 8/1989 | Allen et al. | 206/273 |
| 4,913,138 A | | 4/1990 | Yoshida et al. | 128/155 |
| 4,993,586 A | | 2/1991 | Taulbee et al. | 221/25 |
| 5,080,227 A | | 1/1992 | Focke | 206/273 |
| 5,133,477 A | | 7/1992 | Etheredge et al. | 221/25 |
| 5,160,315 A | | 11/1992 | Heinecke et al. | 602/57 |
| 5,275,284 A | | 1/1994 | Onotsky | 206/441 |
| 5,333,753 A | | 8/1994 | Etheredge | 221/33 |
| 5,397,297 A | * | 3/1995 | Hunter | 602/54 |
| 5,435,459 A | | 7/1995 | Huck et al. | 221/70 |
| 5,499,740 A | | 3/1996 | Huck et al. | 221/70 |
| 5,511,689 A | | 4/1996 | Frank | 221/73 |
| 5,685,833 A | | 11/1997 | Turngren | 602/58 |
| 5,738,642 A | | 4/1998 | Heinecke et al. | 602/58 |
| 5,782,786 A | | 7/1998 | Tomaiuolo | 602/41 |

(Continued)

OTHER PUBLICATIONS

3M Tegaderm and Tegaderm HP Transparent Dressing, 3M Product Catalog, 2000.

(Continued)

*Primary Examiner*—David T Fidei
(74) *Attorney, Agent, or Firm*—Howard Zaretsky; Zaretsky Patent Group PC

(57) ABSTRACT

An element dispensing package suitable for dispensing adhesive strips or bandages. Each element is contained within an envelope formed by opposed upper and lower sheets. The lower sheet has a release liner secured thereto to protect the element while it is within the dispenser. The element is releasably secured to a first tab and is separated from the package when the envelope is opened. The first tab has one or more gripping means to facilitate dispensing of the element contained within the package. Additionally, the upper sheet and the lower sheet have optional gripping means (e.g., a second tab) to facilitate dispensing of the element contained within the package.

10 Claims, 32 Drawing Sheets

U.S. PATENT DOCUMENTS

| | | | |
|---|---|---|---|
| 5,792,092 A | 8/1998 | Turngren | 602/58 |
| 5,891,078 A | 4/1999 | Turngren et al. | 602/58 |
| 5,902,260 A | 5/1999 | Gilman et al. | 602/57 |
| 5,947,998 A | 9/1999 | Cartmell et al. | 606/213 |
| 5,976,117 A | 11/1999 | Dunshee et al. | 604/307 |
| 6,010,002 A | 1/2000 | Petterson | 206/441 |
| 6,018,092 A | 1/2000 | Dunshee | 602/54 |
| 6,050,413 A | 4/2000 | Benedetti | 206/440 |
| 6,053,318 A | 4/2000 | Petterson | 206/440 |
| 6,079,190 A | 6/2000 | Simpson | 53/492 |
| 6,124,522 A | 9/2000 | Schroeder | 602/57 |
| 6,140,549 A | 10/2000 | Pompei | 602/57 |
| 6,169,224 B1 | 1/2001 | Heinecke et al. | 602/58 |
| 6,225,522 B1 * | 5/2001 | Schroeder | 602/57 |
| 6,503,855 B1 | 1/2003 | Menzies et al. | 442/328 |
| 6,923,320 B2 * | 8/2005 | Grossman | 206/440 |

OTHER PUBLICATIONS

D. Satas, Handbook of Pressure-Sensitive Adhesive Technology, Van Nostrand Reinhold, pp. 585-642, 1989.

3M Foam Tapes, Transdermal Drug Delivery Components, 3M Product Catalog, 1999.

Industrial Laser Processes-An Introduction, The Association For Manufacturing Technology.

* cited by examiner

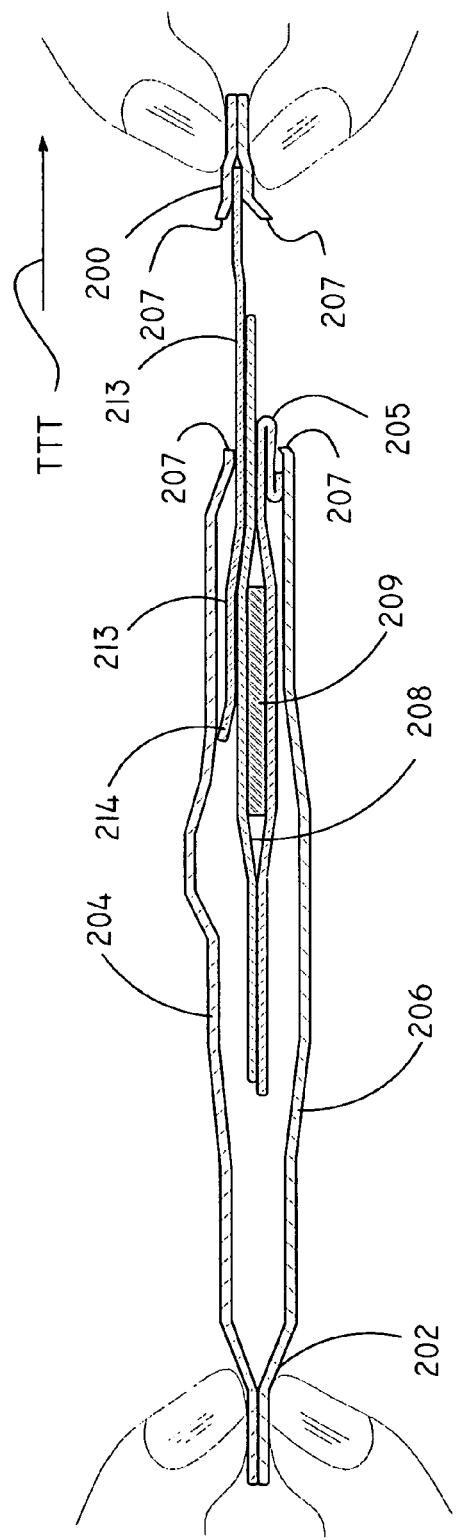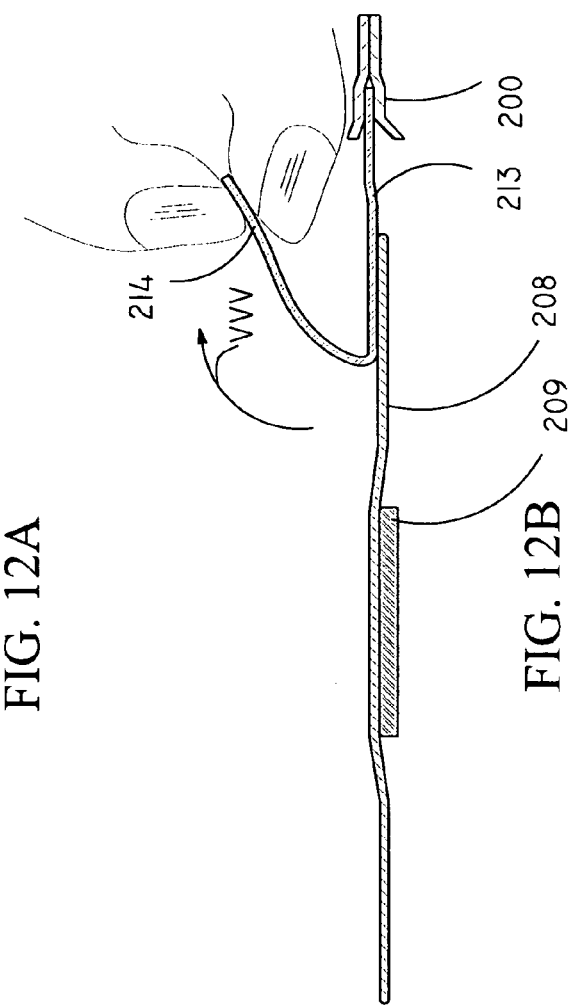
FIG. 12A
FIG. 12B

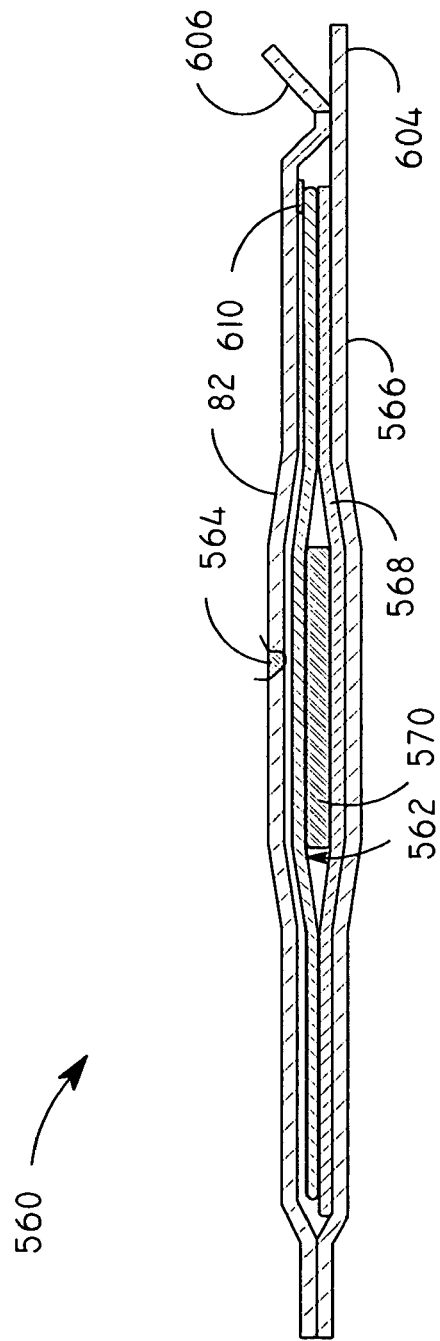
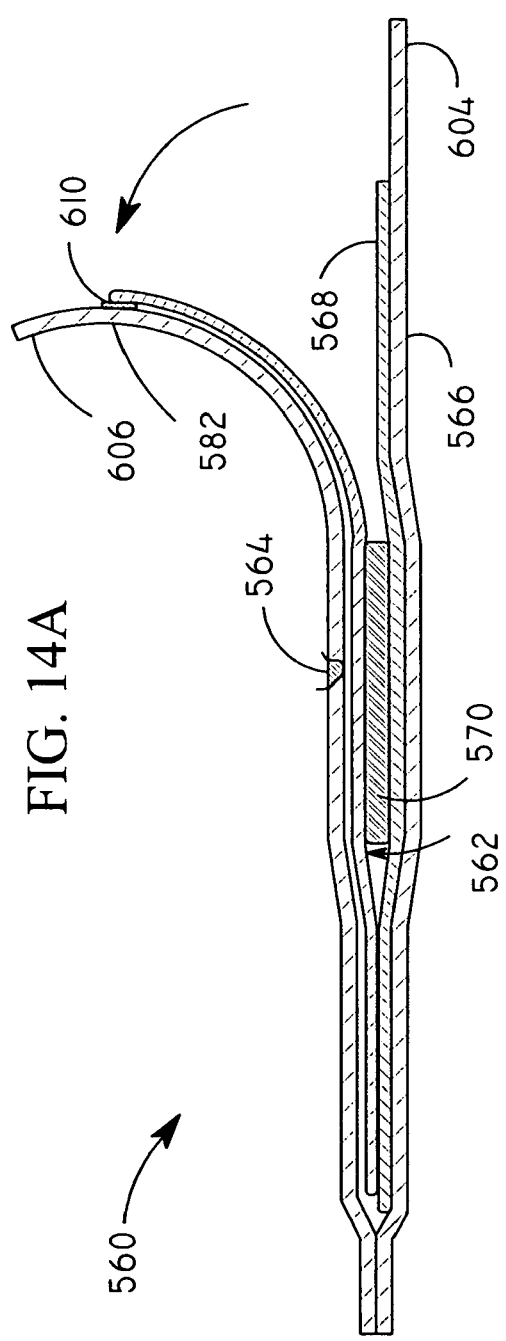
FIG. 14A
FIG. 14B

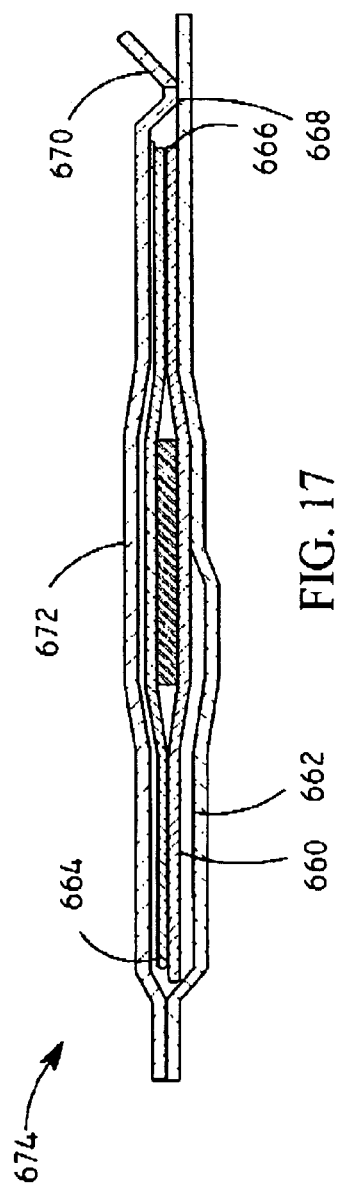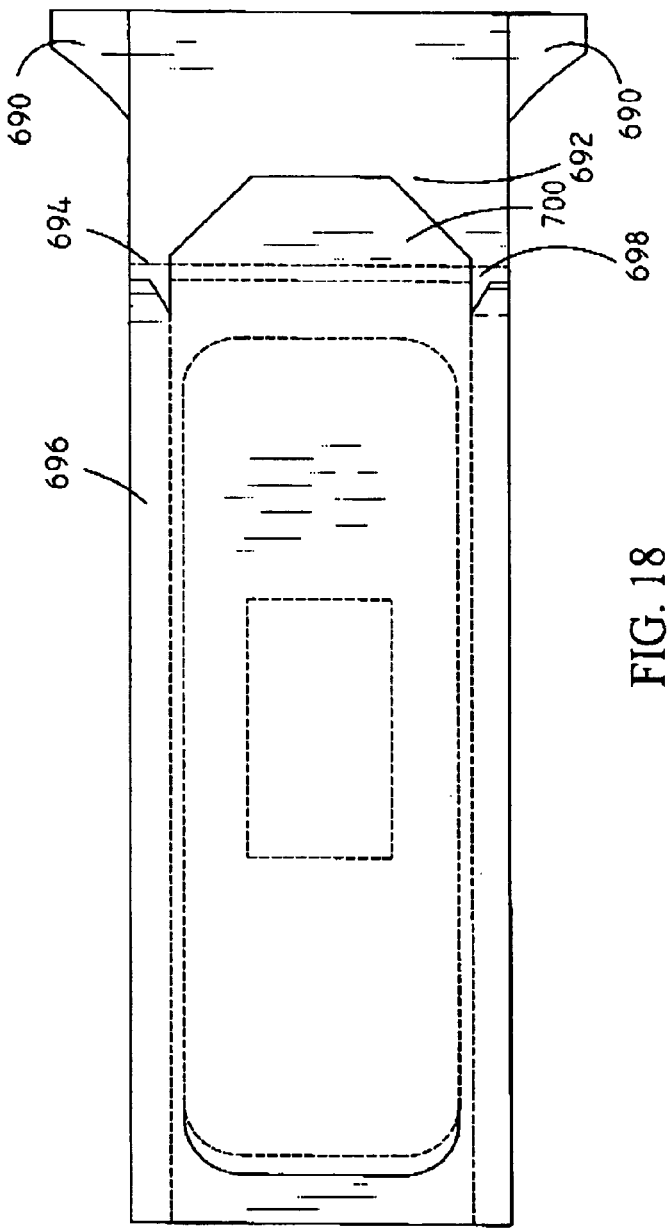
FIG. 17
FIG. 18

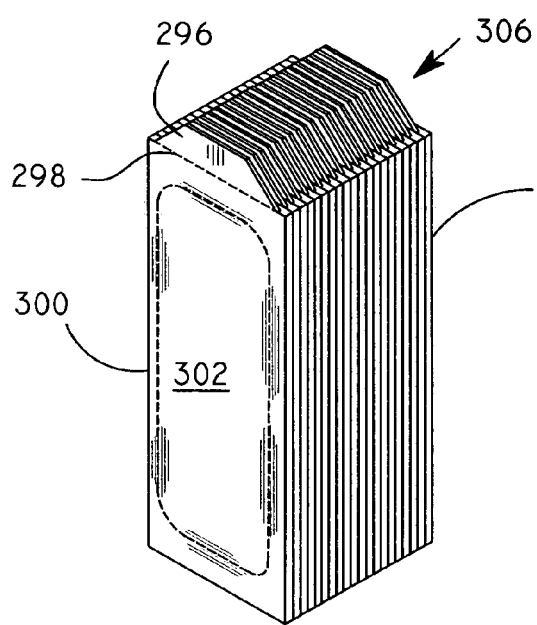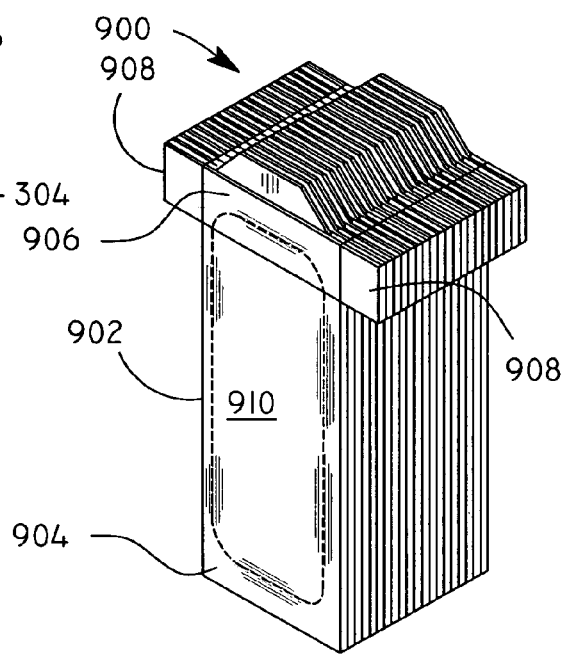
FIG. 27A
FIG. 27B
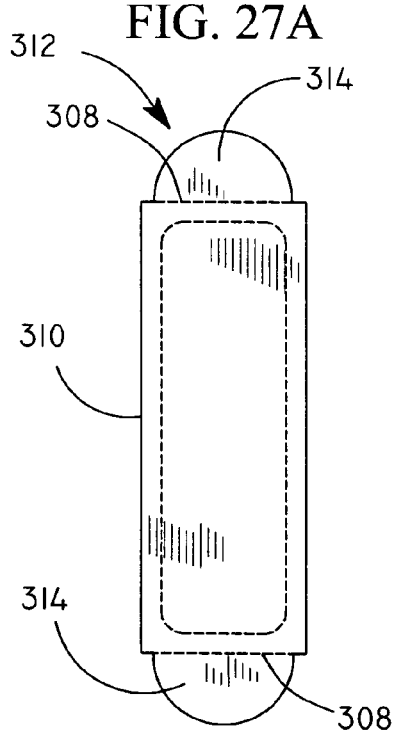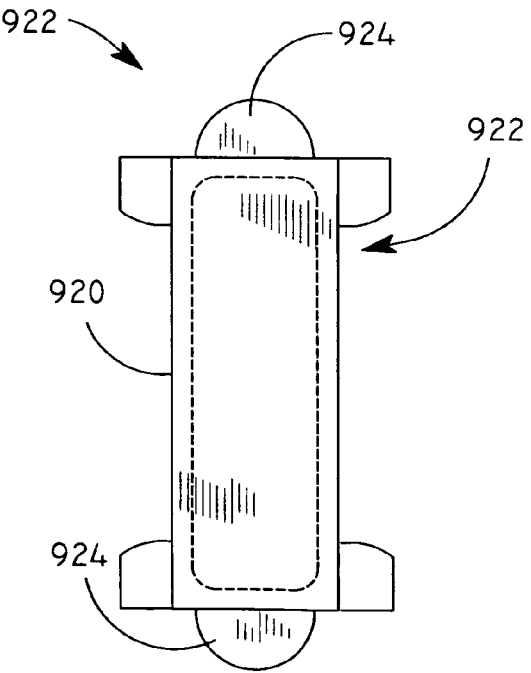
FIG. 28A
FIG. 28B

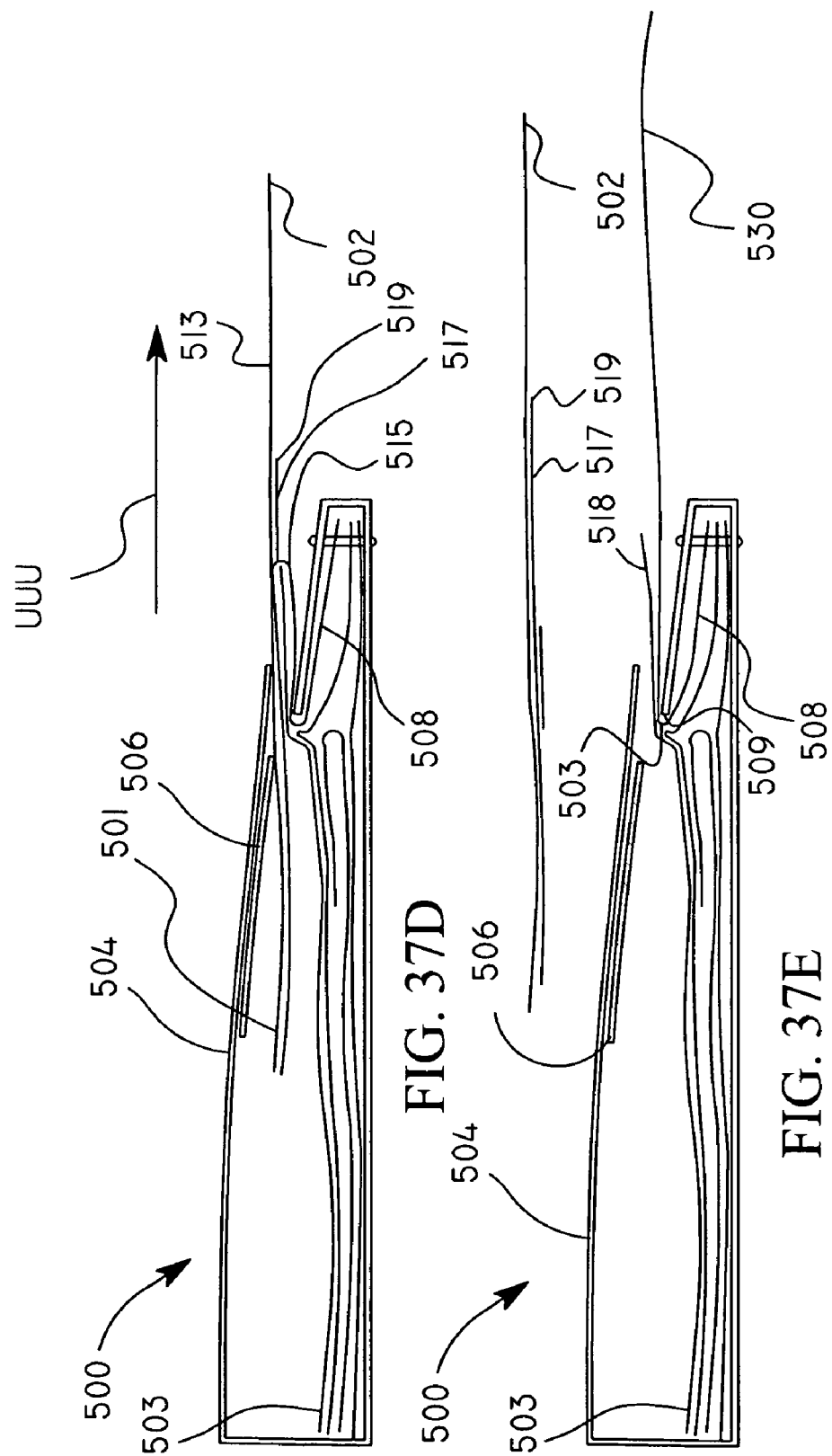

PACKAGING AND DISPENSERS FOR ADHESIVE BACKED ELEMENTS

FIELD OF THE INVENTION

The present invention relates generally to packaging and dispensing systems for adhesive-backed rigid and non-rigid elements such as bandages, strips, and the like, and more particularly to a single-step dispensing system for the elements therein.

REFERENCE TO RELATED APPLICATIONS

The subject matter of the present application is related to, and may be advantageously combined with, the subject matter of the U.S. application Ser. No. 10/190,195, to Grossman, filed Jul. 6, 2002, entitled, "Bandage Package and Dispenser," now U.S. Pat. No. 6,923,320, incorporated herein by reference in its entirety.

BACKGROUND OF THE INVENTION

Packaging and dispensing systems for commonly known adhesive bandages are known in the art and described below. Adhesive bandages, commonly called finger bandages, strip bandages, and first-aid bandages, are well known in the prior art. Commercially available adhesive bandages such as the Band-Aid™ brand bandages are for the most part individually packaged. The most widely used packaging means comprises outer wrappers which must be stripped apart to remove the bandage. The bandage typically consists of a backing on which an adhesive layer is applied to one side, and on which a sterile pad suitable for covering wounds is centrally placed. Two removable liners are placed upon the adhesive-coated side of the backing (or adhesive-backed flexible strip) covering both the pad and the adhesive layer.

Typical prior art adhesive bandages and wrappers require one to open an envelope or package containing the bandage, remove the bandage, peel off the removable liners to expose the adhesive layer and pad and then apply the bandage to the body. Such packaging, however, has certain disadvantages, chief of which are: (a) the possibility of touching the sterile pad before application, which may result in loss of sterility; (b) awkwardness and difficulty in applying the bandage to the body, especially with one hand; (c) having the adhesive surface stick to itself while in the process of applying the bandage to the body, thus requiring either the removal of the bandage and an additional application attempt or discarding the bandage entirely and starting the entire process over with a new bandage; and (d) having to dispose of individual wrapping components, which typically consist of the two removable liners and one or two pieces of outer wrapping.

These disadvantages are exacerbated by the conditions under which bandages are often applied. For example, opening of the package is often done under urgent conditions, which increases the likelihood that the bandage will accidentally fall out of the outer wrapper, resulting in loss of sterility of the bandage.

While some prior designs have simplified the process of application of the bandage, they have several disadvantages. One such prior art approach described in U.S. Pat. No. 4,182,449, to Kozlow, entitled "Adhesive bandage and package" discloses a bandage wherein the user is required to place his fingers near the sterile pad to remove the lining, thus increasing the likelihood of inadvertently touching and contaminating the sterile pad.

There have been other attempts to improve the bandage dispensing and application process, such as by folding the bandage over itself and providing for an automatic removal of the liner, as in U.S. Pat. No. 5,333,753 to Etheredge, entitled "Finger bandage package and dispenser." While this design does provide for removal of the bandage and liner, it requires skill in application, as the opened package is cumbersome and typically requires the use of both hands during application of the bandage. Additionally, as the package is folded over itself, it is difficult for the user to determine the size of the bandage contained therein before the package is opened and the bandage unfolded.

U.S. Pat. No. 5,397,297, to Hunter, entitled "Adhesive Bandage With Improved Application System," discloses an adhesive bandage having essentially flat, planar structural components and including a system to facilitate simplified application of the bandage by providing pairs of release strips folded back across themselves to furnish end members sealed within respective ends of a package so that when the package is opened a release strip is simultaneously pulled away from an adhesive coating of a bandage film thereby further allowing its application with only one hand when necessary. This system requires the release liner to be folded back over itself for the substantially its entire length which increases cost and adds to assembly complexity. Additionally, in order to rip the outer cover, the user must manipulate the package with either both hands or place the package in his or her mouth which is undesirable and would not work with dispensing systems (e.g., linear pulling dispensing packs as are described infra).

With the advent of so called "thin-film" bandages and wound dressings (also known as "Transparent film dressings") there has developed a need to provide sufficient rigidity to the adhesive strip or bandage using a carrier strip, also referred to as a carrier member, outer frame, blocking member, frame style carrier or other means, until the bandage is successfully applied to the desired object. The carrier strip also prevents the thin-film bandage from stretching excessively when the bandage is removed from the package. One commonly used design to impart rigidity to the thin-film strip or bandage is the partial carrier (or frame-style carrier), which is essentially a ring-like structure removably attached to the strip. This design is used in commercially available bandages such as 3M™ NEXCARE™ WATERPROOF BANDAGES. This design, however, requires that the partial carrier be removed upon application of the bandage. Many users, especially those unfamiliar with the design, tend to pull the carrier strip off the bandage before the bandage is removed from the release liner attached to the lower sheet of the package, thus destroying the bandage. Additionally, users often pull the carrier strip off the bandage at the wrong location, and/or try to pull the carrier strip off in the wrong direction, before or after application of the bandage, both of which result in destruction of the bandage. Additionally, this design has the drawback of requiring the user to pull off the carrier sheet after the bandage is applied to the desired object.

Another known thin-film type bandage is the commercially available 3M™ TEGADERM™ TRANSPARENT DRESSING. This bandage uses a frame style carrier and for the most part is similar to the 3M™ NEXCARE™ bandage. One significant difference is that some TEGADERM™ products have a "window" that must be removed before the bandage is applied to a desired surface. This design has the drawback of requiring the user to pull off the "window" section before the bandage is applied to the desired object.

Another known thin-film bandage is the ADVANCED CURAD™ AQUA-PROTECT™ bandage distributed by FUTURO Inc., which uses a full carrier sheet which superposes the adhesive strip or bandage. In this bandage the carrier sheet is releasably attached to the adhesive strip or bandage so that it can be removed by pulling on an attached pull tab (also called a blue flap) once the adhesive strip or bandage is applied to the desired object. A disadvantage, however, is that many users, especially those unfamiliar with the operation of the design, remove the full-length carrier sheet before applying the bandage, resulting in the destruction of the bandage or try to remove the carrier sheet by pulling on a corner of the bandage thereby inadvertently pulling the bandage off the desired object. Moreover, many users, while trying to determine how to remove the carrier sheet, attempt to pull some part of the bandage, but not knowing what or where to pull, they attempt to grasp the pull tab at the interior edge rather than the exterior edge and not being able to grasp it at that point, they give up and do not remove the carrier sheet and therefore do not benefit from the use of the thin-film materials.

Thus, there is a need for an easy to use one-handed bandage package and dispensing system that is capable of dispensing bandages, adhesive strips, flexible strips, or other elements from a dispenser that avoids the problems and disadvantages of prior art systems.

SUMMARY OF THE INVENTION

The present invention is a bandage packaging and dispensing system particularly suited for dispensing adhesive-backed elements such as bandages and the like.

The current invention comprises two major embodiments, a first major embodiment and a second major embodiment each of which has several alternative embodiments.

In the first major embodiment, the package comprises an upper sheet, a lower sheet, an inner tab member, a flexible adhesive strip, and a release liner. The upper sheet has end regions, edge regions, and a weakened line (or area) defining a first tab region. The lower sheet has end regions, side regions, and a weakened line (or area) defining a first tab region. Both the upper sheet and the lower sheet are optionally at least partially coated on one side with a cohesive material (and/or an adhesive) which is suitable for securing the package and which can maintain a sterile seal if desired. The upper sheet superposes (or substantially superposes) the lower sheet and is releasably attached thereto along the outer perimeter of the package. Alternatively, an adhesive or other suitable means is used to bond the upper sheet to the lower sheet.

The adhesive backed elements comprise a backing of suitable material, on one surface of which a pressure-sensitive adhesive is applied to at least a portion thereof and an optional pad suitable for covering the wound is centrally or otherwise placed. The adhesive-coated surface of the flexible strip or bandage is placed in contact with and at least partially superposes a release liner. At least a portion of the release liner is in contact with, and attached to, the lower sheet proximate to the weakened line of the lower sheet. The inner tab member is attached to either or both the tab region of the upper sheet and the tab region of the lower sheet. The second end of the inner tab member has an optional gripping means, such as a removal tab, to assist the user in removing the inner tab member and the attached first tab from the adhesive strip after the adhesive strip has been applied to a desired object. In optional embodiments, the optional wound pad is placed off-center on the adhesive strip.

The end regions and the edge regions of the upper sheet and the lower sheet are fixably attached or releasably attached to each other except at those points where the optional blocking member intervenes between them, at which points the upper and/or lower sheets may be fixably attached or releasably attached to the blocking member so as to form a seal around the outer periphery of the combination formed by the adhesive strip, the release liner, and parts of the inner tab member. Moreover, the blocking member may intervene between the optional inner tab member and either the upper sheet or the lower sheet, in which case the inner tab member can be optionally attached to the blocking member.

The adhesive strip or bandage is placed in an envelope within the package formed by the upper sheet and the lower sheet and is releasably attached to the inner tab member, and is protected by the release liner.

The end regions and the edge regions of the upper sheet and the lower sheet are fixably attached or releasably attached to each other so as to form a seal around the outer periphery of the combination formed by the adhesive strip, the release liner, and the inner tab member.

Optional notches (or cutouts, thinned lines, perforations, etc.) can be placed along the weakened line to assist the separation of the weakened line.

In the second major embodiment, the package comprises an upper sheet, a lower sheet, a flexible adhesive strip and a release liner. The upper sheet has an outer periphery which has end regions, edge regions, a first tab and optional weakened lines defining a pull cover. The lower sheet has an outer periphery comprising end regions, side regions and a first tab. The both the upper sheet and the lower sheet are optionally at least partially coated on one side with a cohesive (or other suitable adhesive) material which is suitable for securing the package and can maintain a sterile seal if desired. The upper sheet superposes the lower sheet and except for that portion which forms the first tab and the second tab, is releasably attached thereto along the outer perimeter of the package.

The adhesive backed elements comprise a backing of suitable material on one surface of which a pressure-sensitive adhesive is applied to at least a portion thereof and an optional pad suitable for covering wound is centrally placed. The adhesive-coated surface of the flexible strip or bandage is placed in contact with and at least partially superimposes a release liner. At least a portion of the first end of the release liner is in contact with and is attached to the lower sheet proximate to the first end region of the lower sheet. Alternatively, the release liner is formed integrally with the lower sheet (e.g., by coating the lower sheet with a U.V. curable release coating).

The pull cover is releasably attached to first end of the adhesive strip. The second end of the pull cover has an optional gripping means, such as a removal tab, to assist the user in removing the pull cover from the adhesive strip after the adhesive strip has been applied to a desired object. In alternative embodiments, the pull cover can extend for a length which is shorter than the length of the upper sheet.

The end regions and the edge regions of the upper sheet and the lower sheet are fixably attached or releasably attached to each other so as to form a seal around the outer periphery of the combination formed by the adhesive strip and the release liner. In alternative embodiments comprising circular (or the like) packages, the end and edge regions are the same and refer to an area which lies somewhere between the periphery of the adhesive strip or bandage and the periphery of the upper sheet and/or the lower sheet so as to envelope the adhesive strip.

Alternatively, one or more optional blocking members are placed along the perimeter of the package to equalize the exterior thickness of the package in desired areas. The blocking member or members are placed at selected locations or continuously along the perimeter of the package.

The end regions and the edge regions of the upper sheet and the lower sheet are fixably attached or releasably attached to each other except at those points where the optional blocking member intervenes between them, at which points the first and/or lower sheets may be fixably attached or releasably attached to the blocking member so as to form a seal around the outer periphery of the combination formed by the adhesive strip and the releasably attached release liner.

Optionally, the upper sheet and the lower sheet are formed integrally from the same sheet of material.

A removal means located opposite the first tab on the pull cover and is suitable for grasping such that the user can remove the pull cover after the bandage is applied. Suitable removal means include a removal tab.

The adhesive strip or bandage is placed in an envelope within the package formed by the upper sheet and the lower sheet and is releasably attached to the pull cover.

Optionally, depending upon the particular embodiment used, the upper sheet and the lower sheet are formed integrally from the same sheet of material.

Optional blocking members may be placed in both major embodiments along the perimeter of the package to equalize the thickness of the package in desired areas. The blocking member or members are placed at selected locations or continuously along the perimeter of the package. If the blocking members superpose the weakened lines of the upper sheet and the lower sheet, then the blocking members should also have weakened lines in those areas which superpose the weakened lines of the upper sheet and the weakened lines of the lower sheet.

In both major embodiments, the package and dispenser are incorporated into a larger assembly by attaching the upper sheet or the lower sheet to additional upper sheets or lower sheets, respectively, along their transverse ends or lateral ends or both so as to form a continuous sheet packaging and dispensing mechanism. The first tabs of each individual package should remain free from each other so that the user can easily grasp individual tabs.

In another embodiment, a plurality of packages is stacked upon each other to form a dispensing pack suitable for dispensing a plurality of elements. Additionally, a box stores a plurality of individual packages or a containing-pack and dispenses elements such as bandages or flexible strips as needed. Alternatively, a plurality of packages and dispensers can be aligned with each other and attached to attachment strips or to a continuous sheet.

An advantage of the present invention is that it simplifies and expedites the bandage-application process by eliminating the need to separate a release liner from the bandage or adhesive strip once the package and dispenser are opened. Furthermore, the present invention obviates the need to dispose of removed release liners. Moreover, as only the first tab, and inner tab member (and/or the optional carrier sheet) remain attached to the bandage during application to the wound, they do not obscure the user's view of the wound or get in the way during the application process. This facilitates precise and convenient one-handed application of the bandage to the wound. Furthermore, the attached tab section or support layer operates as a handle and enhances the user's grip on the bandage during application. Thus, use of the present invention significantly increases the likelihood of successful, precise application of the bandage.

Another advantage of the present invention is that it does not require folds in the packaging material as the package is assembled.

A further advantage of the present invention is that in certain embodiments the force required to open the package is optionally minimized by reducing the length of the weakened line. Additionally, because much of the seal between the upper sheet and the lower sheet does not have to be broken, the adhesives used can be more aggressive which would thus assure a more sterile seal. Additionally, heat bonding can be used which would obviate the need for latex based adhesives which can cause allergic reactions.

An additional advantage of the present invention is the incorporation of features that reduce the complexity and cost of manufacturing. Note that one skilled in the art can easily adapt the packaging and dispensing mechanism of the present invention to package and dispense numerous items such as surgical drapes, nasal strips, diagnostic strips, diagnostic smart bandages, flexible thermometers, medical testing devices, transdermal patches, etc.

The present invention is suitable for use with all types of bandages and adhesive strips including the commercially available bandages such as 3M™ NEXCARE™ WATERPROOF BANDAGES, 3M™ TEGADERM™ TRANSPARENT DRESSING with frame-style carriers (and other types of carriers and including window-style frames as well as other types of frames), 3M™ NEXCARE™ bandage. Additionally, the current invention works with bandages having full carriers such as the ADVANCED CURAD™ AQUA-PROTECT™ bandage distributed by FUTURO Inc., which uses a full carrier sheet which superposes the adhesive strip or bandage.

Additionally, the present invention provides several schemes for dispensing a plurality of flexible strips, adhesive strips, bandages, or other elements, as described elsewhere in this document, from a dispensing packs which use the current invention as well as currently commercial available bandages such as QwikStrip™ brand bandages, manufactured by Qwikstrip Products, A GMP Company, Houston, Tex., which are commercially available and is shown and described in U.S. Pat. Nos. 6,124,522 and 6,225,522, entitled "Packaging for Adhesive-Sided Articles to Allow One Handed Application," and "Assembly for Dispensing Packaged Adhesive-Sided Articles," respectively, to Schroeder. Other adhesive strip dispenser packages which use a carrier or support layer, an adhesive strip attached thereto and a release backing releasably attached to the adhesive strip (or bandage) are also suitable. One such design is described in U.S. Pat. No. 5,685,833, to Tungren, entitled "Sterile Adhesive Bandage and Associated Methods."

Thus, the present invention provides a sterile package dispensing mechanism for flexible strips, bandages or the like which can be easily removed from the dispenser with minimal effort and which can be applied with a single hand thus minimizing the possibility of contaminating the adhesive strip or the absorbent pad or diminishing the adhesive properties of the adhesive strip.

The present invention is compatible with the dispensing packs shown and described in U.S. Pat. No. 6,923,320, to Victor A. Grossman, entitled "Bandage package and dispenser," which is incorporated herein by reference in its entirety.

BRIEF DESCRIPTION OF THE DRAWINGS

The invention is herein described, by way of example only, with reference to the accompanying drawings, wherein:

FIG. 12A is a cross sectional view illustrations of an individual package according to the first major embodiment of the present invention as it is opened and the adhesive strip being removed from the package;

FIG. 12B is a cross sectional view illustration of an inner tab member and first tab being removed from an adhesive strip of the first major embodiment of the present invention;

FIG. 14A is a cross sectional view illustration of the adhesive strip or bandage and dispenser package according to the second major embodiment of the current invention taken along line 14-14 of FIG. 13;

FIG. 14B is a cross sectional view illustration of the adhesive strip or bandage and dispenser package according to second major embodiment of the current invention with the upper sheet, the pull cover and the attached adhesive strip peeled back;

FIG. 17 is a cross sectional view illustration of a second alternative embodiment of second major embodiment of the present invention, which shows an alternative attachment of the release liner to the lower sheet;

FIG. 18 is a detailed top view illustration of a third alternative embodiment of the second major embodiment of the present invention, which shows an alternative second tab which is suitable for side attachment;

FIG. 27A is a perspective view illustration of a sixth embodiment of a dispensing pack;

FIG. 27B is a perspective view illustration of a seventh embodiment of a dispensing pack;

FIG. 28A is a front side view illustration of a eighth embodiment of a dispensing pack adapted to dispense adhesive strips from opposing sides;

FIG. 28B is a front side view illustration of a ninth embodiment of a dispensing pack adapted to dispense adhesive strips from opposing sides;

FIG. 37D is a detailed side view illustration of the container assembly of FIG. 37A as the package is opened; and FIG. 37E is a detailed side view illustration of the container assembly of FIG. 37A as the package is opened.

DETAILED DESCRIPTION OF THE INVENTION

Figure 1:
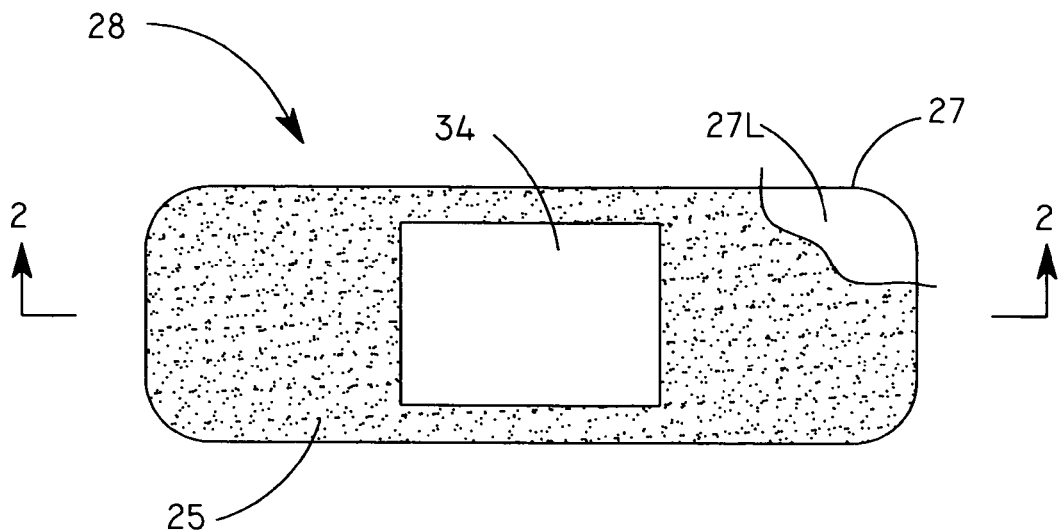
FIG. 1 is a bottom planar view illustration of the flexible strip of the present invention with an adhesive layer and an absorbent pad affixed thereon.

The following terms and definitions may apply throughout this document.

The term flexible strip can be used to denote a strip, spot, transdermal patch (e.g., a medical patch), patch, eye occlusion, testing strip, wound dressing of various shapes and materials (such as commonly-known foam wound dressings), or like device which flexes easily and which has two surfaces, including an upper surface and a lower surface.

The term adhesive strip denotes a flexible strip upon which a suitable adhesive coating is applied to at least a portion of a surface thereof. For example, if a transdermal patch (e.g., a medical patch) is used then the adhesive can contain a desired pharmaceutical composition such as a drug that is to be delivered to a user.

The term bandage can denote a flexible strip with an adhesive coating applied to a surface thereof, upon which an absorbent pad is placed. Alternatively, the term bandage can include medical bandages (or wound dressings) which do not have an absorbent pad placed upon the adhesive surface (e.g., the aforesaid foam or any other suitable bandage material). Moreover, the term bandage can also refer to medical patches. For the sake of clarity, though, when referring to bandages in the drawings a flexible strip with an adhesive coating applied to a surface thereof, upon which an absorbent pad is placed will be shown and used.

In all embodiments of this invention, cohesives may be used rather than adhesives to join or bond surfaces together, except, of course, where practical considerations require otherwise.

The term weakened line denotes a weakened area. For example it can comprise one or more weakened lines or weakened areas. Suitable methods for forming weakened lines include, cutting, scoring, etching, shaving, perforating, orienting fibers (or polymers or strands) in materials, joints made with releasable bonds, or combinations thereof. Additionally, laminated materials with at least one of the laminates having a weakened area such that, when subject to a given force, the material will break in a desired location. Furthermore, any other suitable method of forming a weakened line which will break apart when subject to a desired force can be used.

Note that throughout the present invention, interchangeability of components is contemplated and the corresponding terms throughout this specification including the claims may therefore be substituted for one another as desired as would be reasonable to one skilled in the art. For example, a bandage may be substituted for an adhesive strip.

The term package refers to the combination formed for the most part by an upper sheet, a lower sheet, a first tab and an optional release means. However, when the first tab is separated from the other elements, the term "package" refers to the combination formed by the upper sheet, the lower sheet, and the release means (e.g., the release liner).

The term bond denotes bonds, seams and seals, welds, or other suitable methods of attaching materials to each other unless the context indicates otherwise.

Throughout this invention, when using a blocking member that is placed between, and attached to, both the upper sheet and the lower sheet, it will be assumed that the upper sheet is attached to the lower sheet.

The present invention is applicable to medical dressings and the like and is characterized by an adhesive strip interposed between at least an upper sheet and a lower sheet with an attached removal means included to remove the adhesive strip from the package. A release means is included to protect the adhesive coating of the adhesive-strip. It will be appreciated that the adhesive strip is completely contained between the upper sheet and the lower sheet, the package thus formed constituting a sterile enclosure without the need for additional packaging.

It will be further appreciated by one skilled in the art that the embodiments of the present invention may be constructed using different materials, such as polymers, which include polyurethane, polyolefin, polyester, polyethylene, polyethylene/EVA, polyvinyl, polyvinyl-chloride, plastic, paper, treated paper, cloth, and other materials of suitable construction as well as laminates formed of any suitable materials.

A bottom planar view illustration of the flexible strip of the present invention with an adhesive layer and an absorbent pad affixed thereon is shown in FIG. 1. The adhesive strip 28 comprises a backing layer 27 upon which a pressure-sensitive adhesive surface 25 is applied to a lower surface 27L. An optional absorbent pad 34 suitable for use on wounds is disposed upon the adhesive-coated lower surface, leaving exposed adhesive for securing the flexible strip to a desired object. Although the flexible strip is depicted in a rectangular shape, it will be appreciated that other shapes, such as circular, square, "X," "H," "clover," and "star," are also possible with minimal modifications.

Figure 2:
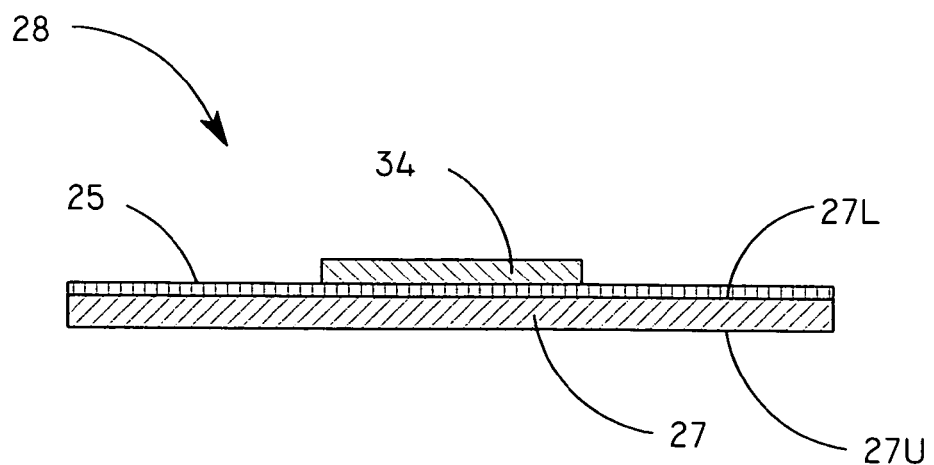
FIG. 2 is a cross section view illustration of the flexible strip of FIG. 1 taken along line 2-2.

A cross section view illustration of the flexible strip taken along line 2-2 of FIG. 1, is shown in FIG. 2. The flexible strip 28 has an upper surface 27U and an opposed lower surface 27L. A pressure-sensitive adhesive surface 25 is applied upon the lower surface 27L. An absorbent pad 34, suitable for use on wounds, is centrally disposed upon the adhesive-coated lower surface, leaving exposed adhesive for securing the adhesive strip to a desired object. Note that for illustration purposes the adhesive surface is depicted as separate from the surface upon which it rests. In other figures which include the adhesive surface the adhesive strip is omitted from the drawings for clarity purposes but is assumed to be present. When the flexible strip is coated with adhesive it will be assumed that the lower surface of the adhesive strip is the adhesive surface.

The flexible strip is constructed from any suitable flexible material rigid enough such that the flexible strip does not fold upon itself during application. Alternatively, if the flexible strip is not constructed from a material of such rigidity, it can be reinforced by using a rigidity-enhancing carrier as described infra. Suitable materials for the adhesive strip include polymers, which include polyurethane, polyolefin, polyester, polyethylene, polyethylene/EVA, polyvinyl, polyvinyl-chloride, plastic, paper, treated paper, cloth, and other materials of suitable construction as well as laminates formed of any suitable materials.

Figures 3, 4A, 4B:
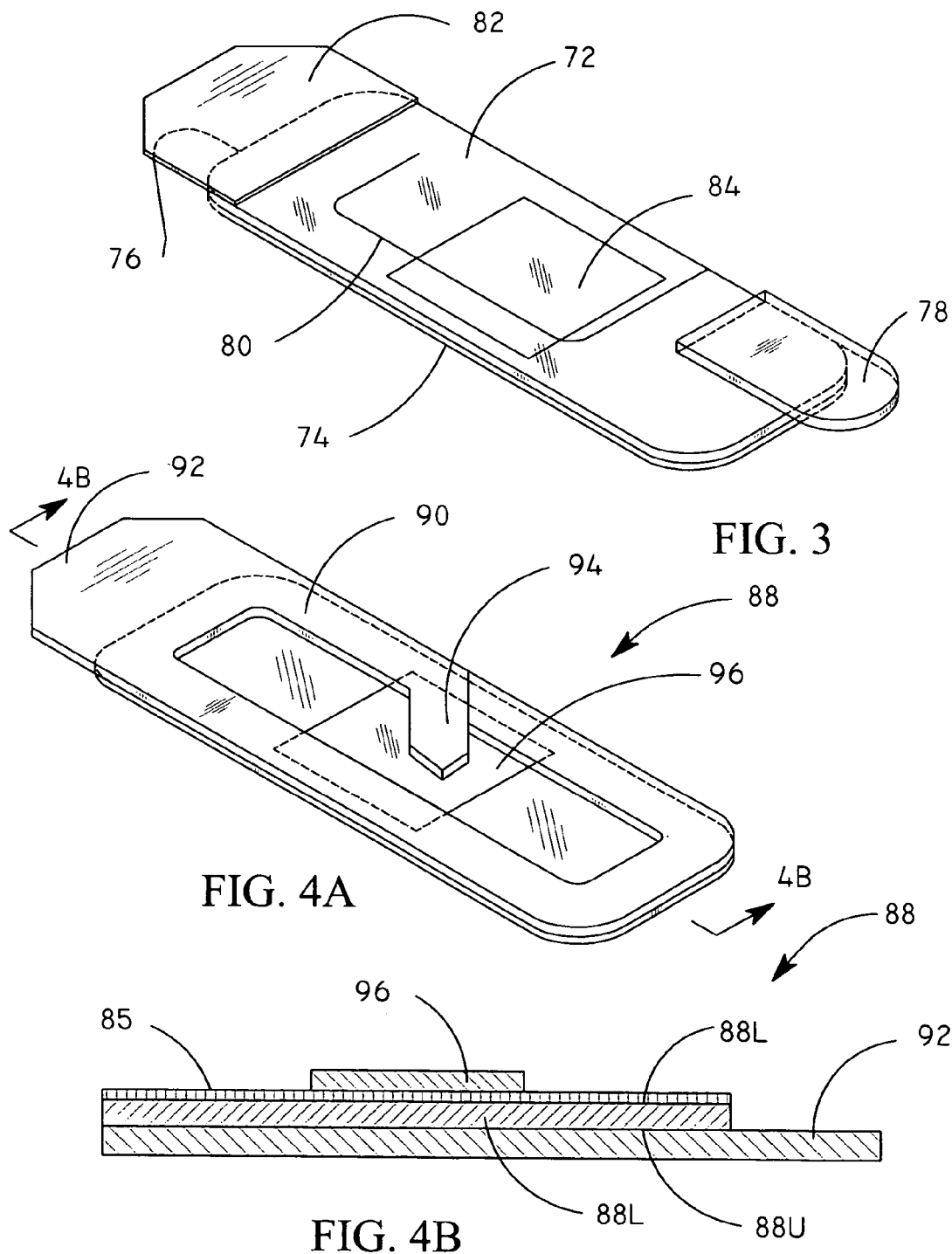
FIG. 3 is a cross-sectional view illustration of a first alternative embodiment of the adhesive strip or bandage with a full carrier and having inner tab members which are attached to the carrier.
FIG. 4A is a perspective view illustration of a second alternative embodiment of the adhesive strip or bandage incorporating a partial carrier.
FIG. 4B is a cross section view illustration of the flexible strip and carrier combination of the present invention, taken along line 4B-4B of FIG. 4A.

A cross-sectional view illustration of a first alternative embodiment of the adhesive strip or bandage with a full carrier and having inner tab members which are attached to the carrier are shown in FIG. 3. The carrier 72 is releasably laminated to the upper surface of the adhesive strip 74, which is releasably laminated to the release liner. The adhesive strip is preferably constructed from thin films (or other types of polymers) of suitable known construction, such as polyurethane or polyethylene, which are commercially available from the 3M Corporation, St. Paul, Minn. The carrier is preferably manufactured from a material rigid enough to prevent curling of the adhesive strip before it is applied to the desired surface, and is releasably laminated using a suitable means such as cold bonding. The carrier is shaped and sized similarly to the adhesive strip so that it is substantially or fully congruent with the adhesive strip. The carrier is preferably bonded to the adhesive strip using a low-tactile adhesive or other suitable means such as is common in the art. The carrier is bonded more aggressively in the area that lies adjacent to the leading edge 76 of the adhesive strip than in other areas of the adhesive strip in order to prevent the carrier from separating from the adhesive strip during removal of the adhesive strip from the package. In an alternative embodiment, the carrier is bonded to the adhesive strip uniformly.

A removal tab 78 is attached to the carrier thus providing a means for grasping the carrier to remove it from the adhesive strip once the adhesive strip is applied to the desired surface. In an alternative embodiment, the removal tab is formed integrally from the same sheet of material as the carrier. The removal tab is preferably located substantially opposite the leading edge of the adhesive strip at a point where it will easily separate the carrier from the adhesive strip. The removal tab is folded over itself and may be releasably bonded to a part of the package so that the removal tab unfolds and is easy to grasp once the adhesive strip is removed from the package and applied to the desired surface. In alternative embodiments, the removal tab is not folded. Optionally, the removal tab may be colored, permitting the user to readily notice if the carrier has not been removed from the adhesive strip after the adhesive strip has been applied to a desired surface.

An optional slit 80 is made in the carrier in order to reduce the effort required to remove the carrier from the adhesive strip. The slit is used to direct the progression of separation of the carrier from the adhesive strip so that it will be perpendicular to the more aggressively-bonded area that lies adjacent to the leading edge of the adhesive strip, thereby reducing the width of the bond at the point of separation. This design is less likely to disturb the bond between the adhesive strip and the surface to which it is attached. In an alternative embodiment, the slit may be omitted.

Either or both the upper sheet and the sheet are attached to the inner tab member 82 which is itself formed integrally with the carrier. The inner tab member extends beyond the perimeter of the adhesive strip so as to form an attachment tab. An optional wound pad 84 is attached to the lower planar surface of the adhesive strip.

Suitable materials for construction of the carrier comprise without limitation polyethylene, polyester, or any other transparent material and/or polymeric material that is suitable for use with the adhesive strip. Such materials are commercially available from the DCP-LOHJA Corp. or the 3M Corporation Medical Specialties Division, St. Paul, Minn.

A perspective view illustration of a second alternative embodiment of the adhesive strip with a one-piece carrier member and inner tab member attached thereto as is shown in FIG. 4A. The adhesive strip 88 has a carrier 90 bonded thereto. The carrier, inner tab member 92, and removal tab 94, are formed integrally from the same sheet of material. A wound pad 96 is shown attached to the adhesive strip. In alternate embodiments, the inner tab member is not necessarily formed from the same sheet of material as the optional carrier. Suitable means for attaching the carrier to the adhesive strip depend upon the type of materials used to construct the adhesive strip and may comprise pressure sensitive adhesives, cohesives, or other means which are commonly known in the art. The bond between the carrier and the adhesive strip should be sufficiently strong so that the carrier does not separate from the adhesive strip before the adhesive strip is applied to a desired surface, but should not be so strong that the carrier, when removed from the adhesive strip, damages the adhesive bond between the adhesive strip and the desired surface. Such carriers are well known in the art.

The outer perimeter of the carrier is shaped and sized similarly to or identically to the adhesive strip so that it is substantially or fully congruent with the outer perimeter of the adhesive strip to which it is attached. In alternative embodiments, the carrier is shaped and sized so that the outer perimeter of the carrier may be located either inside or outside the outer perimeter of the adhesive strip. In other alternative embodiments, the carrier may be die-cut from the same sheet of material as the adhesive strip and may therefore lie in the same plane as the adhesive strip and may surround the perimeter of the adhesive strip. It should be noted that the first end of the inner tab member should always lie outside the outer periphery of the adhesive strip.

The carrier has an opening termed a window in its center section, which enables the user to observe the surface to which it is intended to apply the adhesive strip, thereby allowing for application of the adhesive strip at the precise location desired. Furthermore, the carrier is shaped so that it generally forms a ring-like structure or frame (which may be broken in certain areas) adjacent to the outer perimeter of the adhesive strip which is rigid enough to prevent curling of the adhesive strip during the process of dispensing and applying the adhesive strip. Alternatively, the carrier may be formed to have other shapes, such as described infra.

In alternative embodiments the inner tab member is attached to the carrier rather than directly to the adhesive strip itself.

The carrier may be constructed using any suitable material such as treated paper or kraft paper. Alternatively, the carrier may be made from other suitable materials as are commonly known in the art and which include, without limitation, polymers, etc. which are commercially available. Other types of carriers, such as those which are commonly known in the arts, are also contemplated by the invention. Carriers are well known in the art.

The user is also directed to U.S. Pat. No. 5,160,315, to Heinecke, et al., entitled "Combined adhesive strip and transparent dressing delivery system," and U.S. Pat. Nos. 5,738,642 and 6,169,224, both to Heinecke, et al., and entitled "Carrier delivered dressing and method of manufacture," all of which describe transparent dressings with carrier layers in more detail and are incorporated herein by reference in their entirety.

The carrier has at least one removal means, such as a removal tab 94, to assist the user in removing the carrier from the adhesive strip. Preferably, the removal tab is located within the interior portion of the carrier. Alternatively, however, the pull tab may extend beyond the outer perimeter of the carrier. An optional slit 100 or weakened line is located adjacent to the removal tab. In alternative embodiments, a plurality of removal tabs are used.

In alternative embodiments the carrier comprises one or more holding means. The holding means functions to enable the user to grasp and hold the carrier and the attached adhesive strip. The pull cover functions as a suitable holding means. An alternative holding means comprises a tab that projects beyond the outer perimeter of the adhesive strip and which is large enough for a user to grasp. A cross section view illustration of the flexible strip and carrier combination of the present invention, taken along line 4B-4B of FIG. 4A, is shown in FIG. 4B. The flexible strip 88 has an upper surface 88U and an opposed lower surface 88L. A pressure-sensitive adhesive surface 85 is applied to the lower surface 88L. An absorbent pad 96, suitable for use on wounds, is centrally disposed upon the adhesive-coated lower surface, leaving exposed adhesive for securing the adhesive strip to a desired object. The carrier layer is laminated upon the upper surface of the adhesive strip. Note that for illustration purposes the adhesive surface is depicted as separate from the surface upon which it rests. In other figures which include the adhesive surface the adhesive surface is omitted from the drawings for clarity purposes but is assumed to be present.

Figure 5:
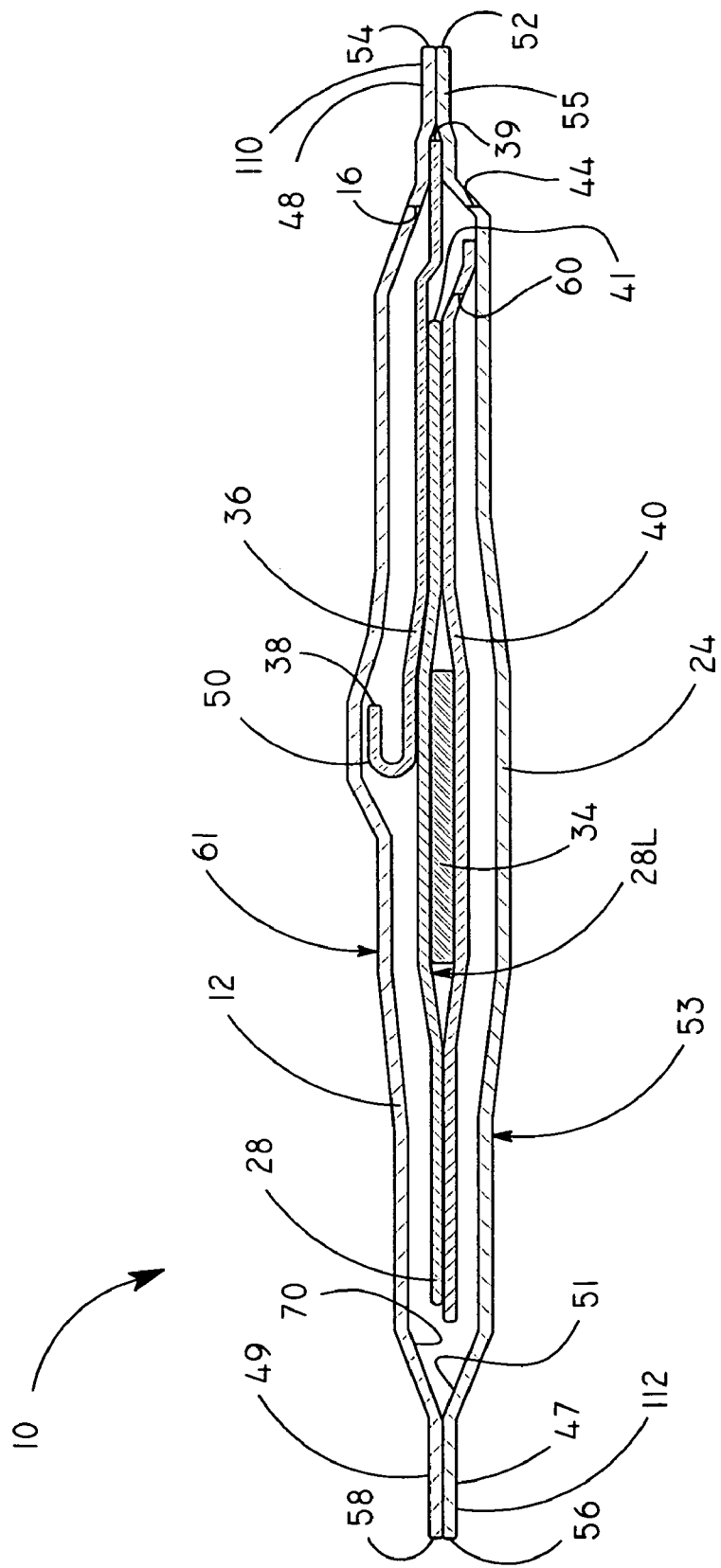
FIG. 5 is a side view illustration of the adhesive strip or bandage and dispenser package with the side edges unattached to each other constructed in accordance with the first major embodiment of the present invention.
Figure 6:
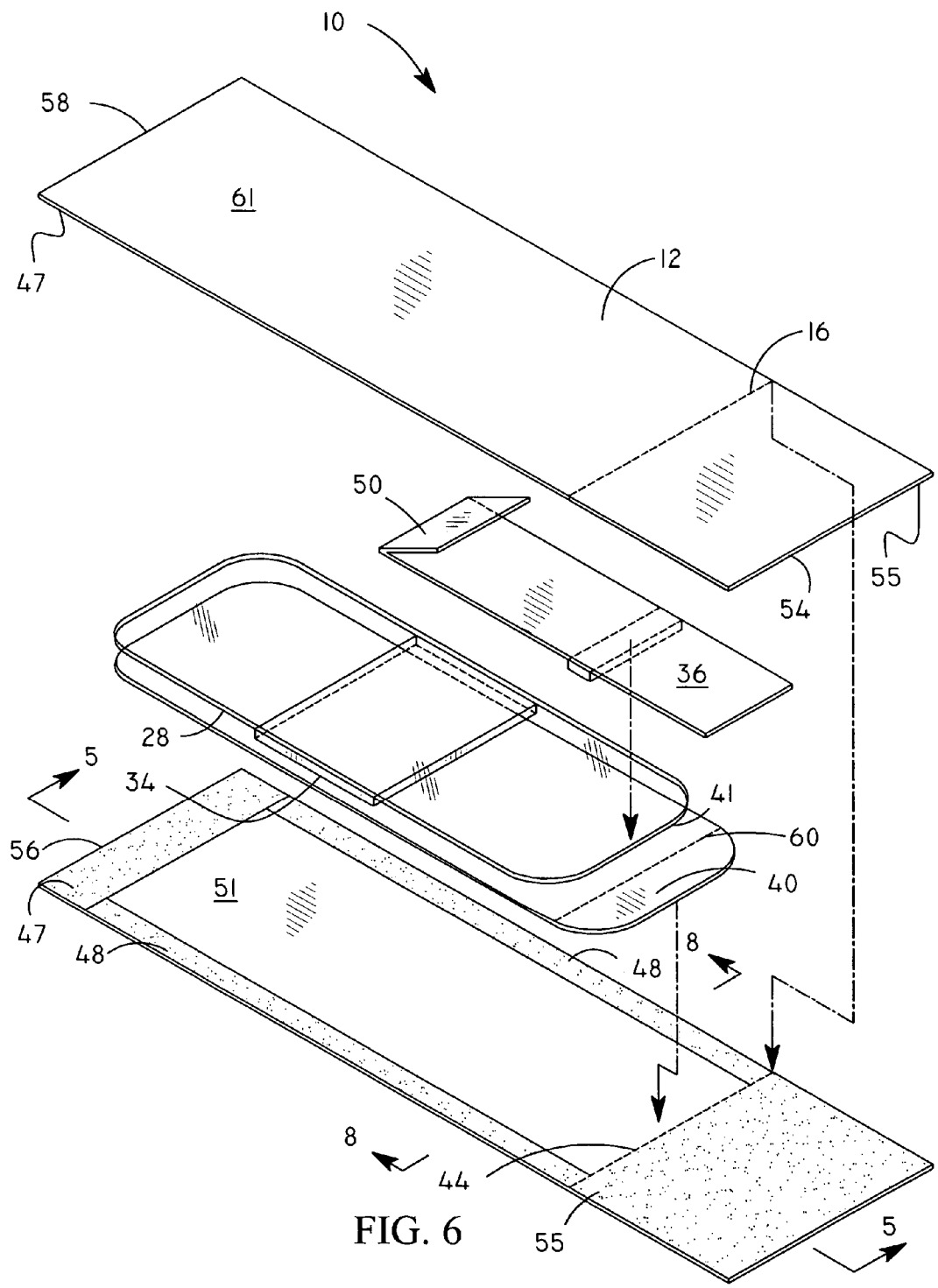
FIG. 6 is an exploded perspective view illustration of the adhesive strip or bandage and dispenser package according to the first major embodiment of the current invention.

A cross sectional view illustration of the adhesive strip or bandage and dispenser package with the side edges unsealed (for illustrational purposes), constructed in accordance with the first major embodiment of the present invention, taken along line 5-5 of FIG. 6 is shown in FIG. 5. A dispenser package 10 comprises a package in which an adhesive strip 28 is incorporated. The package 10 comprises an upper sheet 12, a lower sheet 24, and a release liner 40. The adhesive strip upon which an adhesive surface is applied to the lower surface 28L is suitable for medical applications (e.g., first aid bandages or medical patches), but the invention is not limited to such. The lower surface of the adhesive strip is in direct contact with and is protected by at least one release liner. An optional wound pad 34 is attached to the adhesive surface of the adhesive strip.

The release liner has an optional weakened line 60 which helps the release liner fold when the package is opened, and also lowers the force required to remove the release liner from an opened package. If a single release liner is used, then the release liner extends beyond the outer periphery of the adhesive strip so that the adhesive strip does not adhere to either the upper sheet or the lower sheet. Alternatively, if a plurality of release liners is used, then the release liners can be shaped and sized as desired as long as they operate within the context of this invention. In yet other alternative embodiments, the release liner does not extend beyond the outer periphery of the bandage.

The release liner preferably has a low coefficient of cohesion so that it is easy to remove from the adhesive strip. Additionally, the release liner is flexible enough so that the flexible strip is easily removed from the package. Release liners are well known in the art, and may comprise, for example, a silicone-coated treated paper.

The removal means comprises an inner tab member 36 which has a first end 39 and a second end 38 and is releasably attached to the upper surface of the adhesive strip at a location which is proximate to the leading edge 41 of the adhesive strip using any suitable means which would enable the inner tab member to separate the adhesive strip from the release liner when the package is opened. An optional removal tab 50 is located proximate to the second end of the inner tab member and should be sized such that a user may easily grasp it during use. The first end of the inner tab member extends beyond the exterior periphery of the adhesive strip. The inner tab member can also be releasably attached to other areas of the adhesive strip as desired. A suitable means of attaching the inner tab member to the adhesive strip is by using a pressure-sensitive adhesive applied to the inner tab member so that the inner tab member is releasably attached to the leading edge of the adhesive strip. Alternatively, any other suitable means of attaching the inner tab member to the adhesive strip can be used. The tenacity of the bond between the adhesive strip and the inner tab member should be great enough such that the adhesive strip remains attached to the inner tab member until the adhesive strip is applied to a desired object. Care must be taken so that the strength of the bond between the inner tab member and the adhesive strip allows the inner tab member to be removed from the adhesive strip with minimal effort and without damaging the bond formed by the adhesive surface on the lower surface of the adhesive strip once the adhesive strip has been applied to the desired surface. Alternatively, the inner tab member is attached to, or formed integrally with, a carrier which is attached to the adhesive strip or is releasably attached to the adhesive surface of the adhesive strip.

The removal tab is optionally folded over itself and releasably bonded to the lower surface of the upper sheet such that the removal tab peels away from the upper sheet when the package is opened and the bandage is removed. This will cause the removal tab to extend outward from the bandage when the bandage is applied and thus be more readily seen and pulled by the user.

The upper sheet has an upper surface 61, a lower surface 70, a first end 54 and a second end 58, a first end region 48, a second end region 49, two edge regions and a weakened line 16 (e.g., scoring, thinning, die cutting, laser scoring, or other suitable method). Likewise, the lower sheet has an upper surface 51, a lower surface 53, a first end 52 and a second end 56, a first end region 55, a second end region 47, two edge regions and a weakened line 44. A cohesive is applied to at least the edge regions and the end regions of the lower surface of the upper sheet. A cohesive is applied to at least the edge regions and the end regions of the upper surface of the lower sheet. The upper sheet and the lower sheet are larger than the combination formed by the adhesive strip and the inner tab member so as to be capable of forming a seam around the perimeter of the package formed by the combination of the upper sheet and the lower sheet. The weakened lines of the upper sheet and the lower sheet substantially superpose each other. But, in alternative embodiments the weakened lines of the upper sheet and lower sheet only superpose each other in that area which is closest to the edge regions. The release liner is attached to the lower sheet using any suitable adhesive or bonding method. The inner tab member is sandwiched between and attached to either or both the upper sheet and the lower sheet using adhesive, cohesive, pressure bonding or other suitable bonding method. Alternatively, the upper sheet and the lower sheet may be sealed together using any suitable means.

The end regions of the upper sheet are attached to the end regions of the lower sheet so as to form a first tab 110 and a second tab 112. The release liner is attached to the lower sheet adjacent to the weakened line of the lower sheet. The bond between the release liner and the lower sheet preferably does not separate in use, and should be able to flex sufficiently in order to facilitate the separation of any bonds adjacent to this bond and so that the adhesive strip can easily be separated from the release liner. One suitable method of bonding the release liner to the interior end of the lower sheet is by using a high-tactile pressure-sensitive adhesive. Alternatively, other suitable methods as are well known in the art can also be used. The tab extension is sandwiched between and attached to both the upper sheet and the lower sheet. In alternative embodiments the end region of the first sheet and the end region of the second sheet are joined and share a common weakened line.

The lower surface of the adhesive strip is releasably attached to, and protected by, all or a part of the release liner. The adhesive strip is retained within the package by either or both the release liner and the envelope formed by the attached upper and lower sheets. A low-tack adhesive (or cohesive) is optionally applied to either or both the upper sheet and the lower sheet in the area where it contacts the adhesive strip, the carrier, and/or the release liner, so as to maintain the desired amount of friction when removing the adhesive strip from the package.

The first tab, suitable for grasping, is formed by attaching the first tab regions of the upper sheet and the lower sheet to each other. The optional second tab is formed by attaching the upper sheet and the lower sheet to each other at a location proximate to either the second end of the upper sheet or the trailing end of the lower sheet, and should be suitable for grasping. The bond between the upper sheet and the lower sheet at this location should be sufficiently aggressive so that these sheets do not substantially pull apart from each other when opening the package. Additionally, the second tab should be of sufficient size so that the user can easily grasp it during use. In an alternative embodiment, the upper sheet and the lower sheet are formed from one sheet of material by folding the lower sheet across its width (transverse axis) at a location that is adjacent to the second end of the lower sheet. Alternatively, the upper sheet and the lower sheet are formed from a single sheet of material which is folded across its longitudinal axis so as to form both the upper sheet and the lower sheet. Additionally, the sheets are bonded together so as to form the package and the second tab. Alternatively, the second tab may be omitted.

Preferably, the upper sheet and the lower sheet are constructed from flexible treated paper as is common in the art. Alternatively, other material may be used. An optional wound pad is attached to the lower surface of the adhesive strip. Alternatively, a plurality of optional wound pads may be used.

An exploded perspective view illustration of the adhesive strip or bandage and dispenser package according to the first major embodiment of the current invention is shown in FIG. 6 The upper sheet and the lower sheet are releasably attached to each other along their outer perimeter (i.e., the region defined by the edge regions 48 and the first and second end regions 55 and 47 respectively—the upper sheet having similar edge and end regions which superpose those of the lower sheet which are not shown) except for that portion where they are attached to the inner tab member, so as to form a sterile enclosure for the adhesive strip contained within. One suitable method of attaching the upper sheet to the lower sheet comprises a cohesive or optionally a pressure-sensitive adhesive, pressure bonding, heat bonding, or other suitable bonding method. In alternative embodiments, cold bonding, thermal bonding, pressure bonding, or other suitable bonds, which are common in the art, may also be used. Care should be taken so that the upper sheet and the lower sheet can separate far enough from each other so as to allow the adhesive strip to be easily removed from the package. An optional wound pad is attached to the lower planar surface of the adhesive strip.

Figure 7:
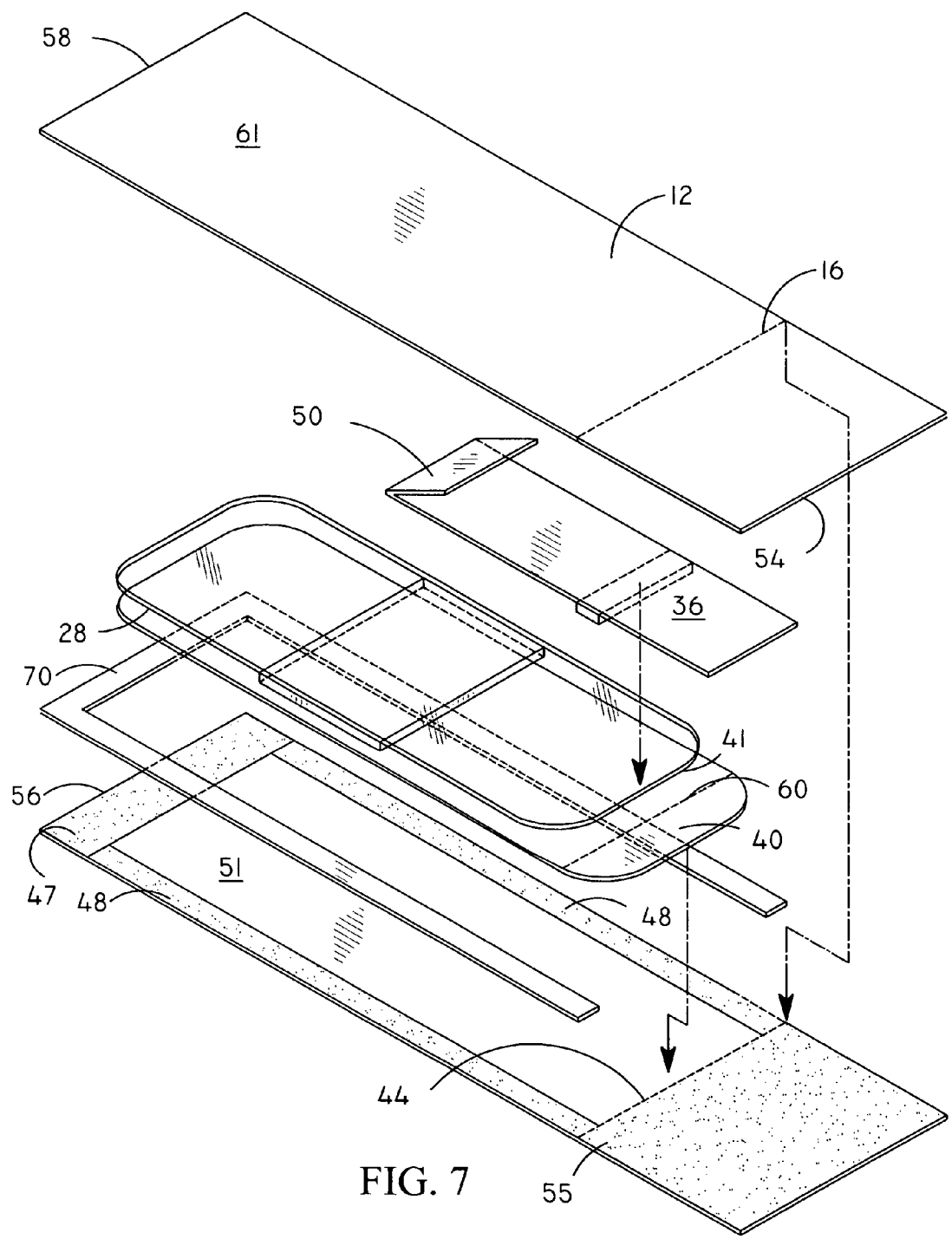
FIG. 7 is an exploded perspective view illustration of the adhesive strip or bandage and dispenser package using a carrier and blocking member according to an alternative embodiment of the first major embodiment of the current invention.

An exploded perspective view illustration of the adhesive strip or bandage and dispenser package using a carrier and blocking member according to an alternative embodiment of the first major embodiment of the current invention is shown in FIG. 7. This embodiment is similar to the embodiment illustrated in FIG. 1, the difference being the inclusion of a blocking member 70 which is well known in the art, which is used to attach the upper sheet to the lower sheet. The upper sheet and the lower sheet are attached to the adjacent side of the blocking member.

Figure 8:
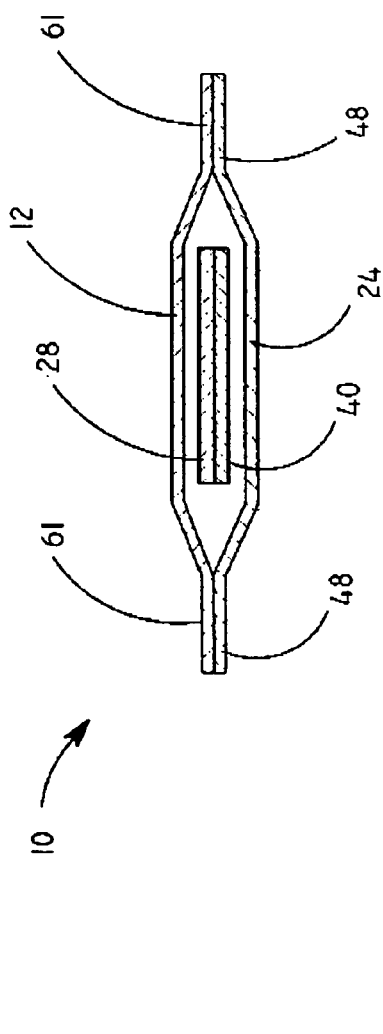
FIG. 8 is a cross-sectional view illustration of the adhesive strip or bandage and dispenser package according to the first major embodiment of the present invention, taken along line 8-8 of FIG. 6.

A cross-sectional view illustration of the adhesive strip or bandage and dispenser package according to the first major embodiment of the present invention, taken along line 8-8 of FIG. 6, is shown in FIG. 8. The side edge regions 61 of the upper sheet are attached to side edge regions 48 of the lower sheet so as to seal the package along the outer periphery of the combination formed by the adhesive strip and the releasably attached release liner and so as to provide an optional sterile envelope for the adhesive strip.

Figure 9:
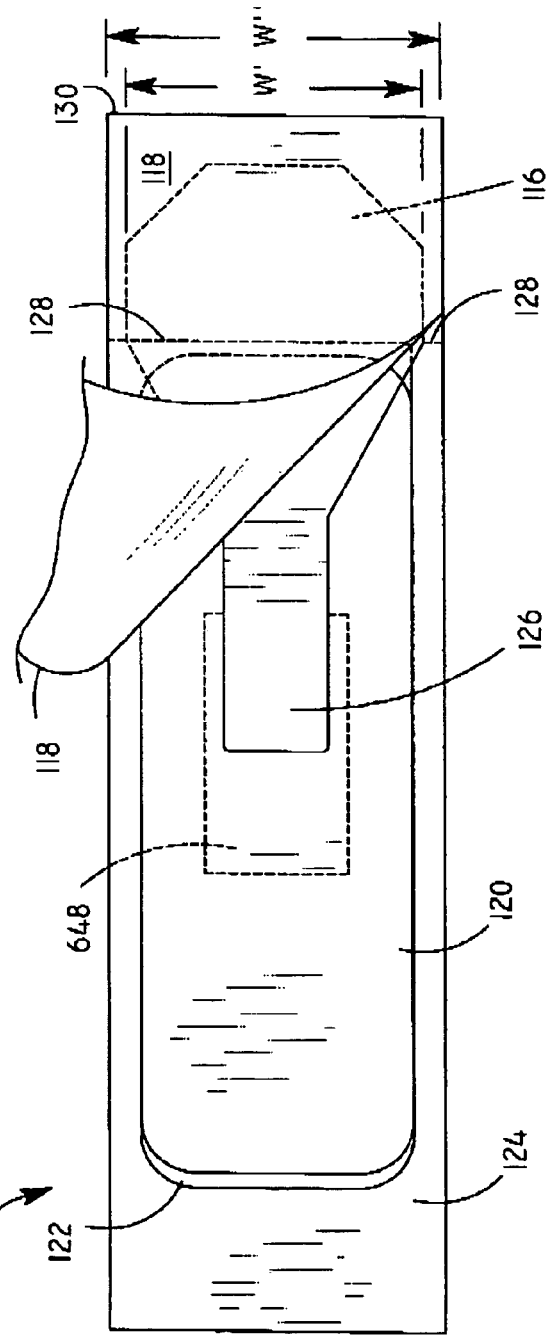
FIG. 9 is a detailed top view illustration of an alternative embodiment of the first major embodiment of the present invention with the upper sheet partially peeled away.

A detailed top-view illustration of an alternative embodiment of the first major embodiment of the present invention with the upper sheet partially peeled away is shown in FIG. 9. The package 114 is essentially similar to the package which is shown and described in FIGS. 5 and 6, the only difference being that the inner tab member 116 is shaped differently. The width (W') of the inner tab member which is located in that area which lies between the weakened line 128 and the first end 130 of the upper sheet (i.e., the first tab region) is narrower than the width (W") of the package. Alternatively, if sterility is not desired then the tab extension can be as wide as (or wider than) the width of the package. The weakened line 128 extends across the width of the package. The width of the inner tab member should be less than the width of the cavity which is defined as that area which lies between edge region bonds of the upper sheet and the lower sheet. This will assure that the inner tab means does not become stuck to the interior of the package. The upper sheet 118 is peeled back to expose the lower sheet 124 and the bandage 120, the removal tab 126, and the release liner 122 which are contained within the package. The weakened line of the lower sheet extends across the width of the package and superposes (or at least partially superposes) the weakened line of the upper sheet.

In alternative embodiments, the release liner is provided with a release means so that at least a major portion of it may be separated from the lower sheet. Without limitation, suitable release means comprise a releasable bond or a weakened line (e.g., either a scored or perforated line) on the lower sheet or on the release liner so as to enable the release liner to be separated from the package 114 after the package is opened.

An alternative embodiment of the first major embodiment of the present invention comprises optional separation notches (not shown). In this embodiment, the package is essentially similar to the package shown in FIG. 9, the only difference being the addition of optional separation notches and the use of a transparent upper sheet. The separation notches are located on either side of the weakened line between the weakened line and the adjacent side edge of the upper and lower sheet. The optional separation notches concentrate separation forces on the weakened line causing it to separate with less force, thus reducing the effort required by the user to open the package. The separation notches may be V-shaped cutouts or the separation notches may also comprise a slit or other weakening.

Figure 10A:
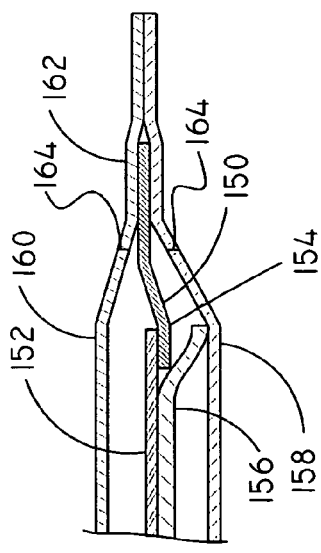
FIG. 10A is a detailed cross-sectional view illustration of a first alternative embodiment of a method of attaching a tab extension to an adhesive strip or bandage.

A detailed cross-sectional view illustration of a first alternative embodiment of a method of attaching the inner tab member to an adhesive strip or bandage is shown in FIG. 10A. The second end 154 of the inner tab member 150 is releasably attached to the adhesive surface of the adhesive strip 152. The second end of the inner tab member is adapted to have a desired coefficient of adhesion in order that it remain attached to the adhesive strip until the adhesive strip is attached to the desired object. The aggressiveness of the attachment is preferably such that the inner tab member remains attached to the adhesive strip until the adhesive strip is applied to a desired object, at which time the inner tab member is able to separate from the adhesive strip without damaging the bond between the adhesive strip and the desired object to which it is attached. The release liner 156 is attached to the lower sheet 158 at a location proximate to the weakened lines 164. The inner tab member is sandwiched between and attached to the upper sheet 160 and the lower sheet in the first tab region 162. In alternative embodiments, the leading end of the release liner can be folded over itself before it is attached to the lower sheet.

Figure 10B:
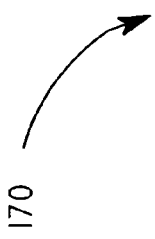
FIG. 10B is a detailed cross sectional view illustration of the present invention showing an alternative attachment of said release liner to said lower sheet using a folded release liner.

A detailed cross sectional view illustration of the present invention showing an alternative attachment of said release liner to said lower sheet using a folded release liner is shown in FIG. 10B. The release liner 57 is folded proximate to its leading end 59 and attached to the upper surface of the lower sheet.

In various embodiments of the present invention, without limitation, the various tabs which are used for grasping may be modified to enable the user more easily to use the present invention. Modifications include, for example, (1) coloring to contrast with the rest of the package, (2) embossing to enhance user touch, feel, and sight, (3) cutting in a way to indicate direction, and (4) numbering, embellishing with arrows, or printing with directions to indicate proper use.

It will also be appreciated that various embodiments of the present invention can be used to dispense items other than adhesive strips or bandages, such as surgical drapes, transdermal patches or the like. In an alternative embodiment, the package or adhesive strip may be inverted so that the adhesive strip emerges with the adhesive surface facing up.

Figure 11:
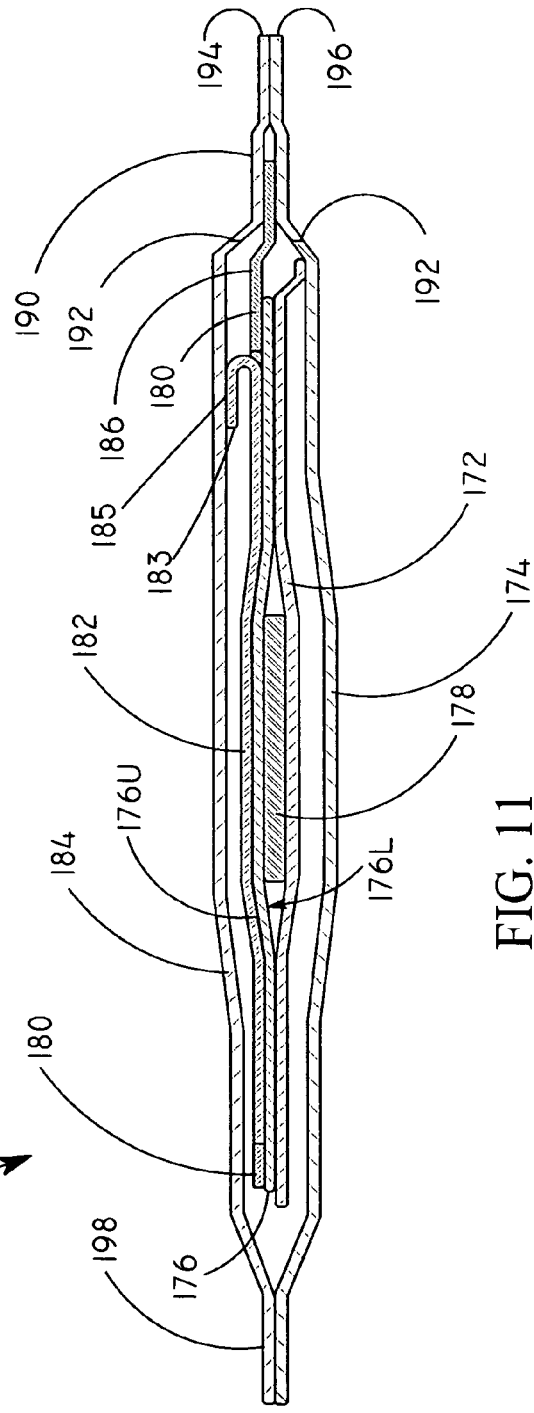
FIG. 11 is a cross sectional view illustration of an alternative embodiment of the first major embodiment of the present invention having an adhesive applied to both the upper and lower surfaces of the adhesive strip and including a carrier.

A cross sectional view illustration of an alternative embodiment of the first major embodiment of the present invention having an adhesive applied to both the upper and lower surfaces of the adhesive strip and including a carrier is shown in FIG. 11. The package 170 is similar to other packages described elsewhere in this document. The release liner 172 is attached to the lower sheet 174 and is releasably attached to the adhesive strip 176. The inner tab member 186 is formed integrally with the carrier from the same sheet of material. The inner tab member is attached to the upper sheet 184 and the lower sheet 174 in the first tab area 190 which lies between the weakened lines 192 of the upper sheet and the lower sheet and the first ends 194 and 196 of the upper sheet and the lower sheet respectively. The second tab 198 is suitable for grasping by the user.

The adhesive strip has an adhesive applied to both the upper surface 176U and the lower surface 176L. A wound pad 178 is optionally attached to the adhesive strip as shown in this example. For example, a carrier 180 (with a window) is attached to the adhesive strip. The upper release liner 182 (which in this example is also a carrier window section) fits within the window formed by the carrier sheet and is releasably attached to the adhesive strip. The upper release liner is removed either automatically during the removal of the pull cover and the adhesive strip from the package in a manner similar to that whereby the release liner is removed, or manually after the adhesive strip is removed from the package. If it is desired that the upper release liner be removed during the removal of the adhesive strip from the package, then the upper release liner should be constructed similarly to the release liner and should be attached to the upper sheet in a manner similar to that whereby the release liner is attached to the lower sheet as described elsewhere in this document. For example, the leading edge of the upper release liner is attached to the upper sheet at bond 105. Alternatively, if it is desired that the upper release liner be removed from the adhesive strip after the package is opened, then the upper release liner should be shaped and sized similar to, or larger than, that upper portion of the adhesive strip which has adhesive applied to it, to protect the adhesive which is applied to the upper surface of the adhesive strip and should not hinder the operation of the invention. Additionally, the upper release liner should include a means (e.g., a tab) to aid the user in removing it from the adhesive strip.

Additionally, if the adhesive strip or bandage comprises a carrier "window" (e.g., such as that which is used in 3M TEGADERM™ Transparent Dressings, Original Frame Style, numbers 1634, 1626, 1628, and 1629, see 3M product catalog, which is similar to the upper release liner 340 as shown and will henceforth also be called a carrier window section) which must be removed before application of the adhesive strip or bandage to the desired surface, then the carrier "window" section may be attached to either the upper sheet or the lower sheet in a manner similar to that by which the release liner is attached to the lower sheet as described hereinabove. This would allow for the removal of the carrier "window" section during the removal of the adhesive strip or bandage from the package while leaving the carrier (if present) attached to the adhesive strip until after the adhesive strip is attached to a desired object. It is noted that the upper surface of adhesive strips which use carrier "window" sections generally have either no adhesive applied or have an adhesive which is not noticeable.

A cross sectional view illustration of an individual package according to the first major embodiment of the present invention (as shown in FIG. 5) as it is opened and the adhesive strip being removed from the package is shown in FIG. 12A. The package is held by the first and second tabs 200 and 202, respectively. The user then pulls the first and second tabs in opposite directions (as indicated by arrow TTT), which causes the first tab to break its bond with the upper sheet 204 and the lower sheet 206 at the weakened lines resulting in separation ends 207. If desired, the user can slightly twist the first tab in relation to the body of the package to aid in the separation of the first tab from the package. The adhesive strip 208 (or bandage) then separates from the release liner 210 beginning at the leading edge of the adhesive strip (or bandage) and continues separating until the adhesive strip (or bandage) fully detaches from the release liner 205. During the separation of the adhesive strip (or bandage) from the release liner, the release liner folds over itself and is pulled out of the envelope formed by the upper and lower sheets. After the pull cover and the attached adhesive strip (or bandage) are separated from the upper sheet, the lower sheet and the release liner, the adhesive strip (or bandage) is applied to the desired surface with the aid of the first tab and any other optional holding means. The adhesive strip (or bandage) is then applied to the desired surface.

A side view illustration of an inner tab member and first tab being removed from an adhesive strip of the first major embodiment of the present invention is shown in FIG. 12B. Note that cross hatching has been used to better illustrate the invention. The adhesive strip has been applied to a desired object (e.g., the user's hand, which is not shown). The inner tab member 213 and the attached first tab 212 are removed by pulling the removal tab 214 in the direction of arrow VVV so that the inner tab member is pulled back over itself and separated from the bandage 208. The wound pad 209 is attached to the bandage. The inner tab member and the attached first tab are then discarded. If a single package is used alone, the package is then discarded. Alternatively, if a dispenser pack is used, then the release liner is optionally separated from the remainder of the package and discarded.

Figure 13:
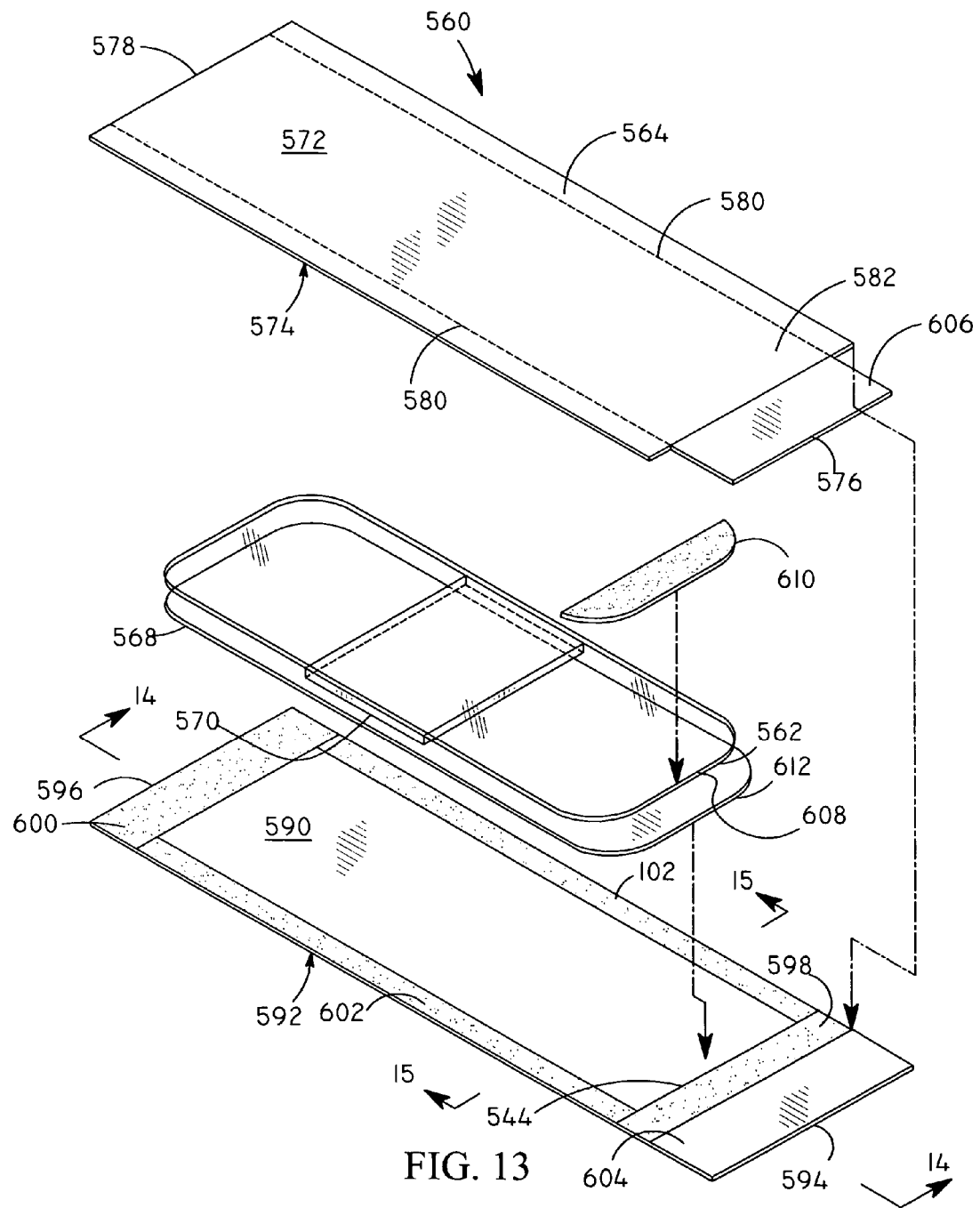
FIG. 13 is an exploded perspective view illustration of the adhesive strip or bandage and dispenser package constructed in accordance with the second major embodiment of the present invention.

An exploded perspective view illustration of the adhesive strip or bandage and dispenser package constructed in accordance with the second major embodiment of the present invention is shown in FIG. 13. The dispenser package 560 comprises a package in which an adhesive strip 562 is incorporated. The package comprises an upper sheet 564, a lower sheet 566, and a release liner 568. A removal means is included to remove the adhesive strip or bandage from the package. The adhesive strip, upon which an adhesive surface is applied to the lower surface, can be suitable for medical applications (e.g., first aid bandages or medical patches) but the invention is not limited to such. The lower surface of the adhesive strip is in direct contact with and is protected by at least one release liner. An optional wound pad 570 is attached to the adhesive surface of the adhesive strip.

The release liner has a low coefficient of cohesion so that it is easy to remove from the adhesive strip. Additionally, the release liner is flexible enough so that the flexible strip is easily removed from the package. Release liners are well known in the art.

The upper sheet, has an upper surface 572, a lower surface 574, a first end 576, a second end 578, a second end region, two edge regions, and one or more optional weakened lines 580 (e.g., scoring, thinning, die cutting, laser scoring, or other suitable method) which define a pull cover 582. The lower sheet has an upper surface 590, a lower surface 592, a first end 594 and a second end 596, a first end region 598, a second end region 600, two edge regions 602, and a second tab region 604. By way of example only, the second end region and the two edge regions of the upper sheet superpose the corresponding locations of the lower sheet. An optional adhesive/cohesive is applied to at least the edge regions and the end region of the lower surface of the upper sheet. An optional adhesive/cohesive is applied to at least the edge regions and the end regions of the upper surface of the lower sheet. The size of the combination formed by the upper sheet and the attached pull cover is similar to the size of the lower sheet. The size of the lower sheet is larger than the size of the combination formed by the adhesive strip, the releasably attached release liner (and the optional carrier) so as to be capable of forming a seam around the perimeter of the package formed by the combination of the upper sheet the releasably attached pull cover and the lower sheet. Alternatively, the upper sheet and the lower sheet could be sealed together using any suitable means. The first end region of the pull cover is releasably attached to the lower sheet using an adhesive/cohesive or other suitable bonding method. The release liner is attached to the lower sheet using any suitable adhesive/cohesive or other suitable bonding method. In optional embodiments, only the leading end 612 of the release liner is attached to the lower sheet (proximate to the first end region of the lower sheet). In yet other alternative embodiments, a substantial part of the release liner is attached to the lower sheet. In alternative embodiments, the outer perimeter of the package is not fully sealed.

The bond between the release liner and the lower sheet preferably does not separate in use, and should be able to flex sufficiently in order to facilitate the separation of any bonds adjacent to this bond and so that the adhesive strip can easily be separated from the release liner.

The removal means comprises a pull cover which has a first end 576, a second end 578, and a first tab 606 which is proximate to the first end and is suitable for grasping. The pull cover is releasably attached to the upper sheet at the weakened lines 580, and is releasably attached to the upper surface of the adhesive strip at a location which is proximate to the leading edge 608 of the adhesive strip using any other suitable means which would enable the pull cover to separate the adhesive strip from the release liner when the package is opened. The pull cover can also be releasably attached to other areas of the adhesive strip as desired. A suitable means of attaching the pull cover to the adhesive strip is by using a pressure-sensitive adhesive 610 applied to the pull cover so that the pull cover is releasably attached to the leading edge of the adhesive strip. Other means of attaching the pull cover to the adhesive strip include double sided adhesive tape or any other suitable methods as are common and well known in the art. The tenacity of the bond between the adhesive strip and the pull cover should be great enough such that the adhesive strip remains attached to the pull cover until the adhesive strip is applied to a desired object. Care must be taken so that the strength of the bond between the pull cover and the adhesive strip allows the pull cover to be removed from the adhesive strip with minimal effort and without damaging the bond formed by the adhesive surface on the lower surface of the adhesive strip once the adhesive strip has been applied to the desired surface. Alternatively, the pull cover is attached to, or formed integrally with, a carrier which is attached to the adhesive strip or is releasably attached to the adhesive surface of the adhesive strip. When the package is opened the pull cover separates from the upper sheet at the weakened lines. The bond between the upper sheet and the lower sheet is stronger than the bond between the upper sheet and the pull cover so that when the package is opened the pull cover separates from the upper sheet along the weakened lines without disturbing the bond between the upper sheet and the lower sheet.

The lower surface of the adhesive strip is releasably attached to, and protected by, all or a part of the release liner. The adhesive strip is retained within the package by either or both the release liner and/or the envelope formed by the envelope formed by the attached first and lower sheets. In alternative embodiments, a low-tack adhesive (or cohesive) is optionally applied to either or both the upper sheet and/or the lower sheet in the area where it contacts the adhesive strip, the carrier and/or release liner, so as to maintain the desired amount of friction when removing the adhesive strip from the package.

In an alternative embodiment, the upper sheet and the lower sheet are formed from one sheet of material by folding the lower sheet across its width (transverse axis) at a location that is adjacent to the second end of the lower sheet. Alternatively, the upper sheet and the lower sheet are formed from a single sheet of material which is folded across its longitudinal axis so as to form both the upper sheet and the lower sheet. Additionally, the sheets are bonded together so as to form the package and the second tab.

Preferably, the upper sheet and the lower sheet are constructed from flexible treated paper as is common in the art. Alternatively, other material may be used. An optional wound pad is attached to the lower surface of the adhesive strip. Alternatively, a plurality of wound pads may be used.

A cross sectional view illustration of the adhesive strip or bandage and dispenser package according to the second major embodiment of the current invention taken along line 14-14 of FIG. 13 is shown in FIG. 14A. One suitable method of attaching the upper sheet 564 to the lower sheet 566 comprises a cohesive or, optionally, a pressure sensitive adhesive or other suitable bonding method which is compatible with the materials used. In alternative embodiments, cold bonding, thermal bonding, pressure bonding, or other suitable bonds, which are common in the art, may also be used. The bond between the pull cover and the first end region of the lower sheet can be similar to, or different from the bond between the upper sheet to the lower sheet depending upon the desired release force required. If the pull cover is not as large as or larger than the adhesive strip or bandage then care should be taken so that the upper sheet and the lower sheet can separate far enough from each other or, that the upper sheet can flex sufficiently so as to allow the adhesive strip to be easily removed from the package as it is opened. The release liner is attached to the lower sheet. In alternative embodiments the release liner is attached to the lower sheet proximate to the first end region 598. The first tab 606 and the second tab 604 are sized such that they are suitable for grasping. Alternatively, if the second tab is affixed to some object, then, the second tab can be smaller as desired. In other alternative embodiments the second tab beyond the edge regions of the lower sheet and be affixed to some object so as to position the package in a desired location.

A cross sectional view illustration of the adhesive strip or bandage and dispenser package according to second major embodiment of the current invention with the upper sheet, the pull cover and the attached adhesive strip peeled back is shown in FIG. 14B. The adhesive strip is attached to the pull cover using an adhesive. The second end region of the upper sheet and the lower sheet are sealed together, but, for purposes of illustration, the side regions of the upper sheet and the lower sheet are also not sealed together.

Figure 14C:
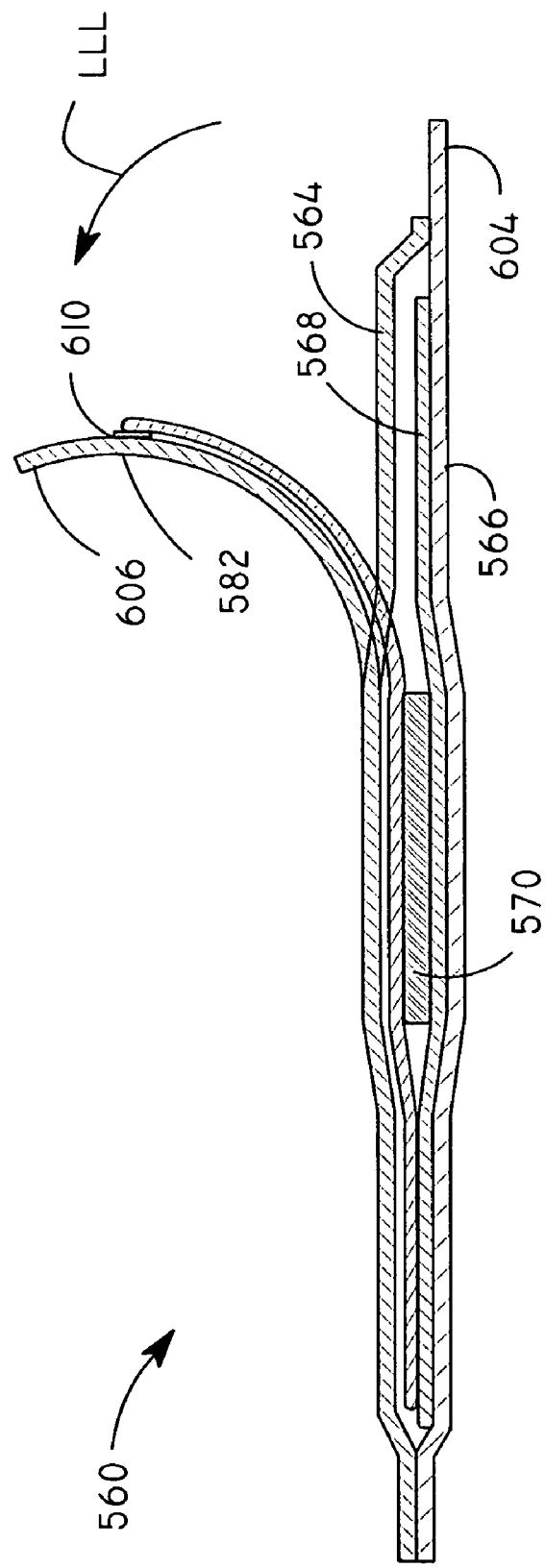
FIG. 14C is a cross sectional view illustration of the adhesive strip or bandage and dispenser package according to the second major embodiment of the current invention as it is being opened non-axially and the pull cover and the releasably attached adhesive strip being pulled away from the lower sheet and the release liner.

A cross sectional view illustration of the adhesive strip or bandage and dispenser package according to the second major embodiment of the current invention as it is being opened non-axially and the pull cover and the releasably attached adhesive strip being pulled away from the lower sheet and the release liner is shown in FIG. 14C. The pull cover is seen separating from the upper sheet at the weakened lines. The weakened lines continue to separate until the pull cover and the releasably attached adhesive strip are fully separated from the package.

In use the user grasps the first tab and second tab and then pulls them in the direction shown by arrow LLL which separates the pull cover from the upper sheet (at the weakened lines) and the lower sheet and also separates the adhesive strip (which is releasably attached to the pull cover) from the release liner. In alternative embodiments, the second tab is attached to a locating means. This illustration demonstrates the non-axial opening of the current invention.

Figure 15:
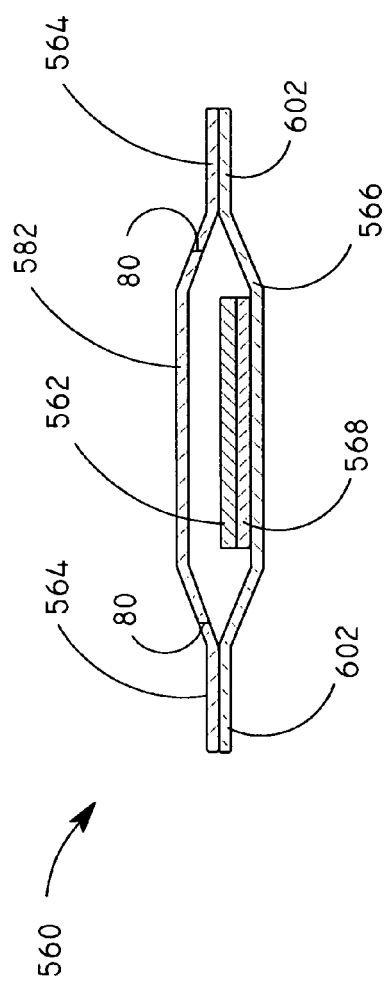
FIG. 15 is a cross-sectional view illustration of the adhesive strip or bandage and dispenser package according to the second major embodiment of the present invention, taken along line 15-15 of FIG. 13.

A cross-sectional view illustration of the adhesive strip or bandage and dispenser package according to the second major embodiment of the present invention, taken along line 15-15 of FIG. 13, is shown in FIG. 15. The side edge regions 564 of the upper sheet is attached to side edge regions 602 of the lower sheet so as to seal the package 560 along the outer periphery of the combination formed by the adhesive strip and the releasably attached release liner and so as to provide an optional sterile envelope for the adhesive strip. Suitable, optional methods of attaching the release liner to the lower sheet are also shown and described in U.S. Publication No. US20040004014, entitled "Bandage Package and Dispenser," cited hereinabove.

Figure 16:
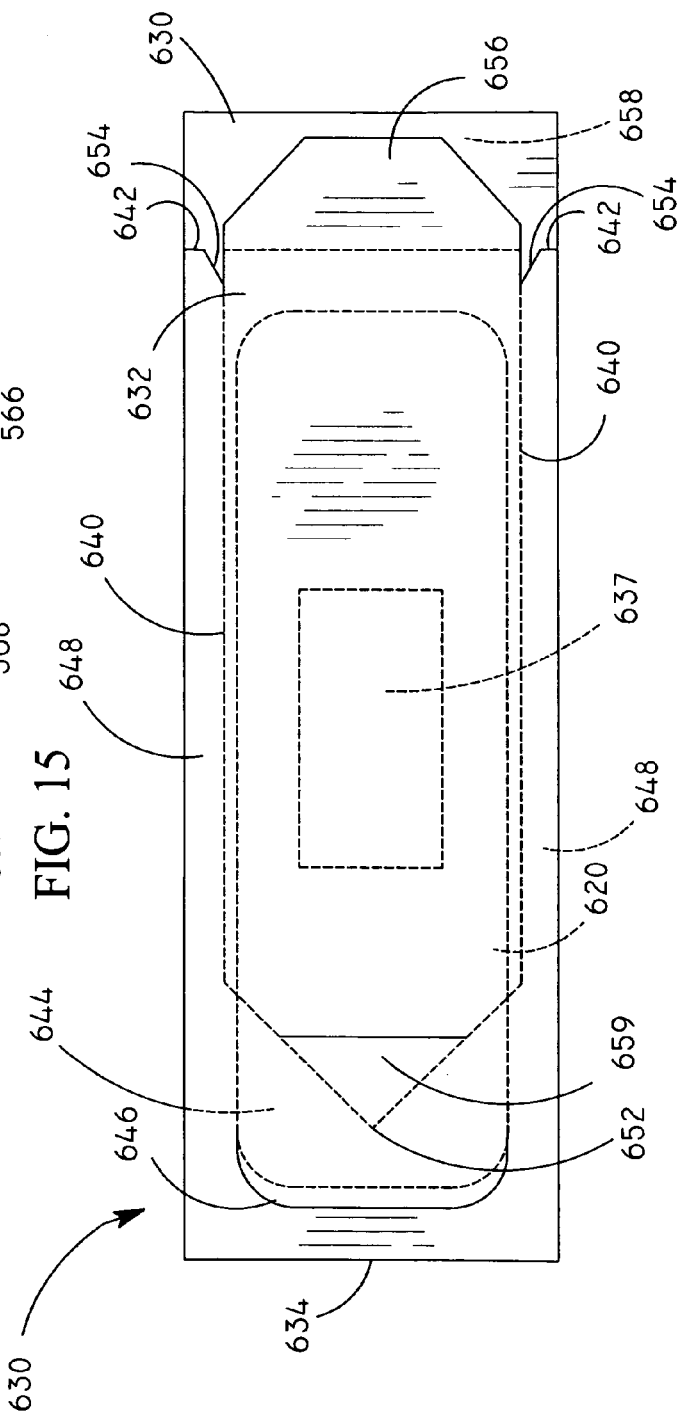
FIG. 16 is a detailed top view illustration of the adhesive strip or bandage and dispenser package according to a first alternative embodiment of the second major alternative embodiment.

A detailed top view illustration of the adhesive strip or bandage and dispenser package according to a first alternative embodiment of the second major alternative embodiment is shown in FIG. 16. The weakened lines 640 extend from the first end 642 of the upper sheet 650 and intersect with each other at a terminal point 652 which is between the first end and the second end 634 of the upper sheet, as desired so as to form a chevron. The leading end of the adhesive strip 644 is attached to the pull cover 632. Optional separation notches 654 are provided to aid in the initial separation of the weakened lines. The separation notches can be cutouts, scores, weakened lines, etc. This would reduce the peel-type stress between the first and lower sheet when the package is opened, and would assure that the upper sheet does not separate from the lower sheet. The first tab is 656 shaped as desired. The second tab 658 is extended and may be sized as desired. For example, if it is intended that individual units of the bandage dispensing package are to be used separately by holding them in a users hand, then the first and second tabs should be sized sufficiently so that they can be grasped by the user. But, in alternative embodiments where the second tab is attached to a positioning means then the second tab can be shaped as required. For example, the second tab may extend beyond the lengths of the first tab or the second tab can be folded over itself and extended to the sides of the package for attachment to an attachment and positioning means. The removal means forms a pull tab 659 which is located opposite the first tab. In optional embodiments the pull tab is located on the carrier.

In alternative embodiments the weakened lines extend from the first end to a point which is anywhere between the first end and the second end of the upper sheet. In yet other alternative embodiments the weakened line or lines intersect with other weakened lines the shape being unimportant as long as the shape of the weakened lines allow the pull cover to be removed from the upper sheet. The pull cover can be shaped and sized as desired as long as the first cover does not interfere with the adhesive strip as it is being removed from the package.

Depending upon the materials used, and the location of adhesives used to bond the pull cover to the adhesive strip, the pull cover may have a natural tendency to curl thus making it easier to remove after the adhesive strip has been applied to a desired object.

A wound pad 637 is attached to the lower surface of the adhesive strip. The edge regions 648 of the upper sheet and the lower sheet are attached to each other so as to envelope the adhesive strip contained within the package. The edge regions of the first and lower sheet should not separate from each other as the package is opened. The weakened lines are placed apart from each other so that the first cover does not interfere with the adhesive strip as it is removed from the package. As the pull cover is separated from the upper sheet the separation progresses along the weakened lines until it reaches point 652 at which point the separation member separates from the upper sheet. A pull tab, suitable for grasping, is then formed proximate to the point 652. This design has an advantage of a shorter length pull cover which would ease application of the adhesive strip or bandage in small radius applications. The weakened lines could converge with each other using straight or bent line.

The release liner is attached to the lower sheet using an adhesive/cohesive or other suitable method which is compatible with the materials used. The release liner could be attached along its entire length or alternatively, could be attached at its leading end and at any other optional points for any desired length. Alternatively, the weakened lines can be placed such that the upper cover rubs against the adhesive strip as the adhesive strip is removed from the package. This can create a desired amount of retention force.

A cross sectional view illustration of a second alternative embodiment of second major embodiment of the present invention, which shows an alternative attachment of the release liner to the lower sheet is shown in FIG. 17. The release liner 660 is attached to the lower sheet 662 along a substantial part of the release liners length. Those parts of the release liner which are not attached to the lower sheet are free to peel away from both the bandage 664 as the bandage is removed from the package and may extend beyond the perimeter of the package as the package 674 is opened. The bandage is attached to the pull cover 670, and the upper sheet 672 is attached to the lower sheet as described supra. In alternative embodiments, the leading end 666 of the release liner is attached to the lower sheet only proximate to the first end region 668 of the lower sheet. In yet other alternative embodiments, the leading end of the release liner and an additional minor portion of the release liner are attached to the lower sheet. In yet other alternative embodiments, the release liner extends beyond the outer periphery of the adhesive strip and is folded back over itself and then attached to the lower sheet.

A detailed top view illustration of a third alternative embodiment of the second major embodiment of the present invention, which shows an alternative second tab which is suitable for side attachment is shown in FIG. 18. This embodiment is similar to the embodiment illustrated in FIG. 13 the difference being the addition of transverse extension appendages 690 which are formed integrally with the second tab 692 such that when the second tab is folded at optional fold 694, such that it now is located under the lower sheet 698, it extends beyond the outer periphery of the edge regions of the larger of either or both the upper sheet 696 and/or the lower sheet. The appendages are then attached to a locating means. This design is suitable for axial pull dispensing packs which will be discussed infra. The first tab 600 may be extended as desired depending upon application. In alternative embodiments, the transverse extension appendages can be formed from a separate sheet of material which is attached to the second tab using an adhesive or other means.

A third alternative embodiment of the present invention comprises an alternative second tab which is suitable for side attachment (not shown). The second tab is folded under the lower sheet at optional fold. In alternative embodiments, the second tab is not folded and extends forward of the package. Further, optional notches may be included.

Figure 19A:
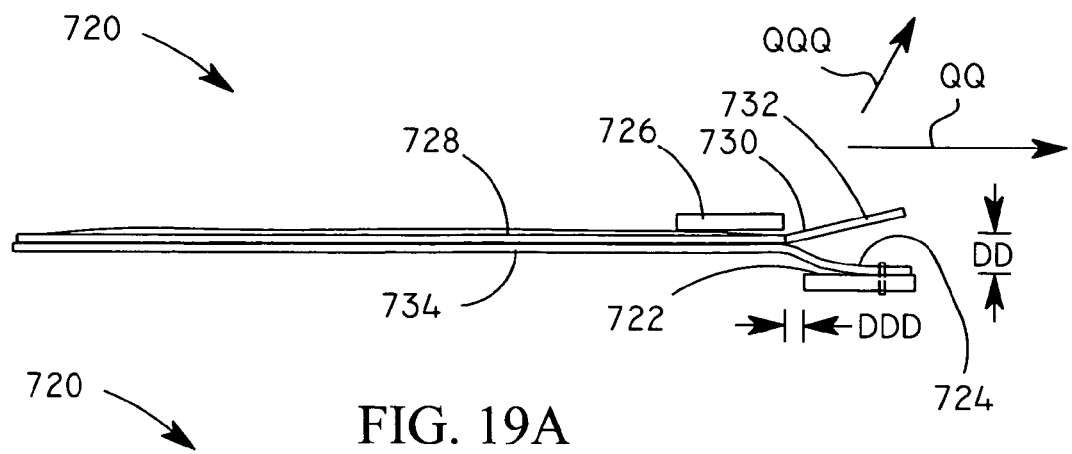
FIG. 19A is a side view illustration of the second major embodiment of the present invention attached to and held in position by a locating means.

A side view illustration of the second major embodiment of the present invention attached to and held in position by a locating means is shown in FIG. 19A. The package 720 is held in position by two locating means. A first locating means 722 is attached to the second tab 724 and holds the second tab in position. A second locating means 726 holds the package from substantially lifting while it is being opened but allows the package to slide relative to it as the package is being opened. The second locating means is optionally in contact with the upper sheet 728 and/or the pull cover 730. The first tab 732 is shaped and sized such that it can be easily grasped by the user. The first and second locating means are separated from each other by a distance DD such that the package can slide between it when the package is opened. The first and second locating means can superpose each other or be set back from each other by a distance DDD as shown. The distance between the first and second locating means will be coined an exit window. The first and second locating means should be located such that when the user pulls the first tab, the package begins to pass through the exit window and begins to open. In the preferred embodiment the user pulls the first tab in a direction indicated by arrow QQ, but, in alternative embodiments, the user can pull the first tab in a direction indicated by arrow QQQ or in other directions which are suitable for the design. The locating means is as wide as or wider than the width of either or both the upper sheet and/or the lower sheet 734 so that it extends across the width of the package and so that it extends over both edge regions of either or both the upper sheet and/or the lower sheet. Alternatively, the locating means in not as wide as the width of the package. Suitable locating means can comprise a matchbook-type container as will be discussed infra.

Figure 19B:
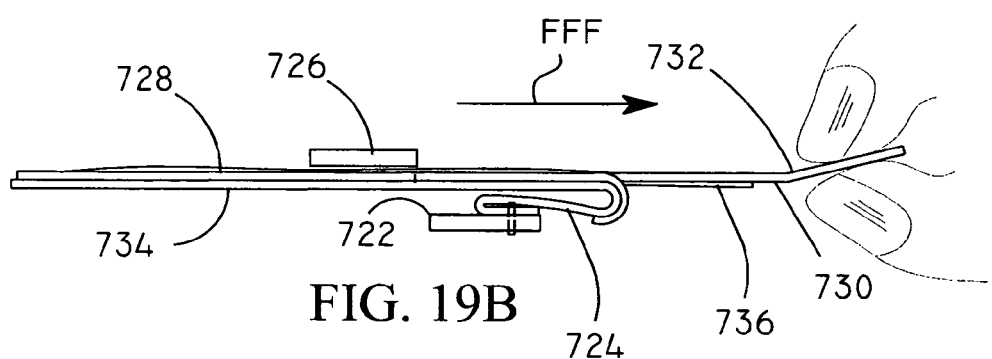
FIG. 19B is a side view illustration of the second major embodiment of the present invention which shows a package being opened by pulling linearly.

A side view illustration of the second major embodiment of the present invention which shows a package being opened by pulling linearly is shown in FIG. 19B. The user grasps the first tab and pulls it away from the dispenser linearly in the direction indicated by arrow FFF. The pull cover is seen separating from the upper sheet at the weakened lines. The weakened lines continue to separate until the pull cover and the releasably attached adhesive strip 736 are fully separated from the package. Alternatively the user can pull in upward or in other directions as desired.

Figure 20A:
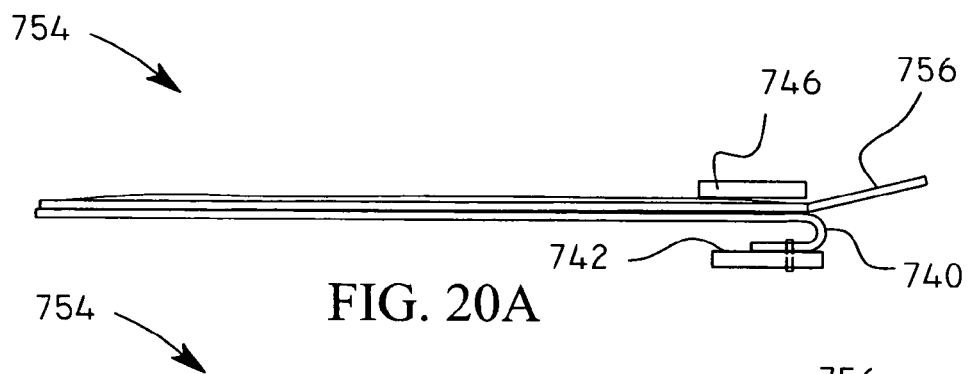
FIG. 20A is a side view illustration of an alternative embodiment of the second major embodiment of the present invention attached to and held in position by a locating means.

A side view illustration of an alternative embodiment of the second major embodiment of the present invention attached to and held in position by a locating means is shown in FIG. 20A. The package 754 is essentially similar to the embodiment shown in FIG. 19A and described in the corresponding text. The difference being that the second tab 740 is folded over itself before being attached to the first locating member 742 and the placement of the second holding member 746 substantially superposing the first holding member. Additionally, the first tab 756 protrudes beyond the exterior periphery of the lower sheet as shown.

Figure 20B:
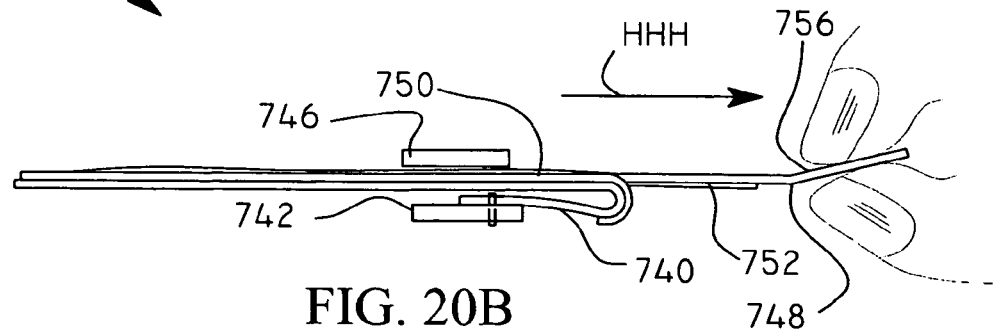
FIG. 20B is a side view illustration of an alternative embodiment of the second major embodiment of the present invention which shows the package being opened.

A side view illustration of an alternative embodiment of the second major embodiment of the present invention which shows the package being opened is illustrated in FIG. 20B. The user grasps the first tab and pulls it away from the dispenser linearly in the direction indicated by line FFF'. The pull cover 748 is seen separating from the upper sheet 750 at the weakened lines. The weakened lines continue to separate until the pull cover and the releasably attached adhesive strip 752 are fully separated from the package 754. Alternatively the user can pull at slight angles to line FFF'.

Suitable locating means include adhesives, staples, pressure bonds, or other suitable bonding method or locking method which would hold the desired object in place.

Additionally, other types of adhesive strip or bandage packages may be substituted for adhesive strip or bandage package which is shown and described in the current document. For example, QwikStrip™ brand bandages which are commercially available and is shown and described in U.S. Pat. Nos. 6,124,522 and 6,225,522, entitled "Packaging for Adhesive-Sided Articles to Allow One Handed Application," and "Assembly for Dispensing Packaged Adhesive-Sided Articles," respectively, to Schroeder, both of which are incorporated herein by reference in their entirety, can be used as a substitute in the various disclosed dispensing packs and container assemblies. Likewise, other designs such as is described in U.S. Pat. No. 5,685,833, to Tungren, entitled "Sterile Adhesive Bandage and Associated Methods," which is incorporated herein by reference in its entirety, can be substituted instead with little modification.

The present invention provides several schemes for dispensing a plurality of flexible strips, adhesive strips, bandages, or other elements, as described elsewhere in this document, from a dispensing pack. These are illustrated in FIGS. 21 through 28B. The dispensing pack comprises a plurality of packages arranged in rows so as to form a dispensing pack. It should further be noted that the rows can be staggered, if desired. Each scheme will now be described in more detail.

Figure 21:
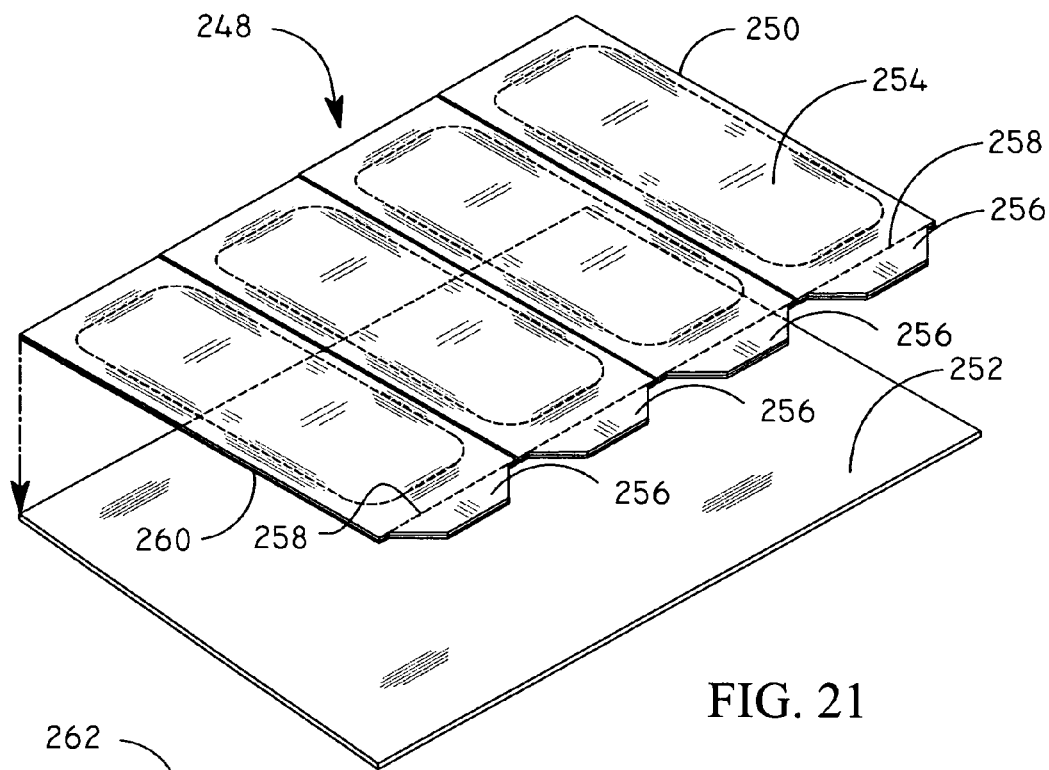
FIG. 21 is an exploded perspective view illustration of a first embodiment of a dispensing pack.

An exploded perspective view illustration of a first embodiment of a dispensing pack is shown in FIG. 21. The dispensing pack 248 comprises a plurality of packages which are aligned along their longitudinal axis in the same or substantially the same plane (which may include a curved plane). The individual upper sheets 254 and lower sheets 260 are attached to each other. A means for holding individual packages 250 functions to hold the packages in close proximity to one another. A suitable means for holding individual packages in alignment comprises a continuous sheet 252 long enough such that multiple packages can be mounted thereto. Alternatively, a suitable means for holding individual packages in alignment comprises a continuous upper sheet and/or lower sheet long enough such that multiple packages can be mounted thereto. An optional rigidity-enhancing means is associated with either the lower sheet or the upper sheet. In an alternative embodiment, either the continuous sheet, the upper sheet, or the lower sheet is constructed from a substantially rigid material. A means for holding the dispensing pack is used to hold the dispensing pack in position for dispensing the adhesive strips. If a suitable means for holding the dispensing pack is employed, then the second tab may be omitted. The first tabs 254 are connected to the upper and lower sheets via weekend lines 258. Moreover, in alternative embodiments, the first tabs 256 are separated from each other by optional score lines and are not connected in any way.

Figure 22:
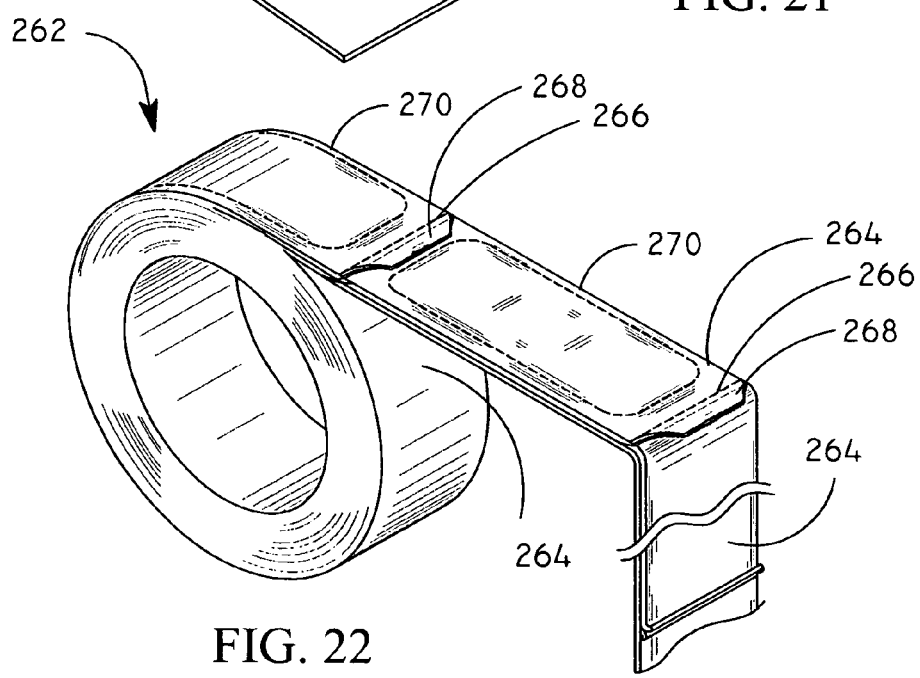
FIG. 22 is a perspective view illustration of a second embodiment of a dispensing pack.

A perspective view illustration of a second embodiment of a dispensing pack is shown in FIG. 22. The dispensing pack comprises a continuous roll sheet of material upon which a plurality of packages 270 are aligned and attached along their lateral axis. The first tabs 268 are not attached to the continuous roll sheet of material and extend such that the user can easily grasp them and separate them at weakened lines 266. The weakened lines include an optional notch on each side to reduce the effort required to remove the first tab from rest the package at the weakened line. The continuous roll dispensing pack 262 can be placed within a dispenser adapted to support and contain the continuous roll dispensing pack. To reduce the likelihood of jamming, the first tabs can be releasably attached to either the continuous sheet or the upper sheet 264 of the preceding package using a light tack adhesive. This light tack adhesive will allow the first tabs to separate from either the preceding package or the continuous sheet when the continuous sheet is torn away from the roll. Additionally, a low tack adhesive or cohesive (or other bonding means) can be applied to the upper surface of the upper sheet and/or the lower surface of the lower sheet or the lower surface of the continuous sheet, whichever comes into contact with the upper surface of the upper sheet. This light coat of adhesive will increase the force required to separate the packages from the roll. This, in turn, will provide a resistive means, said resistive means being necessary for the proper operation in some embodiments of the present invention. In alternative embodiments a physical resistive means (e.g., a friction device or other friction means) is included. In alternative embodiments the packages are attached to each other using a flexible material and a bonding means. For example, the adjacent packages can be attached to each other using individual adhesive attaching strips (such as Scotch™ Brand Tape or other suitable method). In optional embodiments, the continuous roll is wrapped around a rigid cylindrical holding member such as a spool to provide for stability.

Figure 23A:
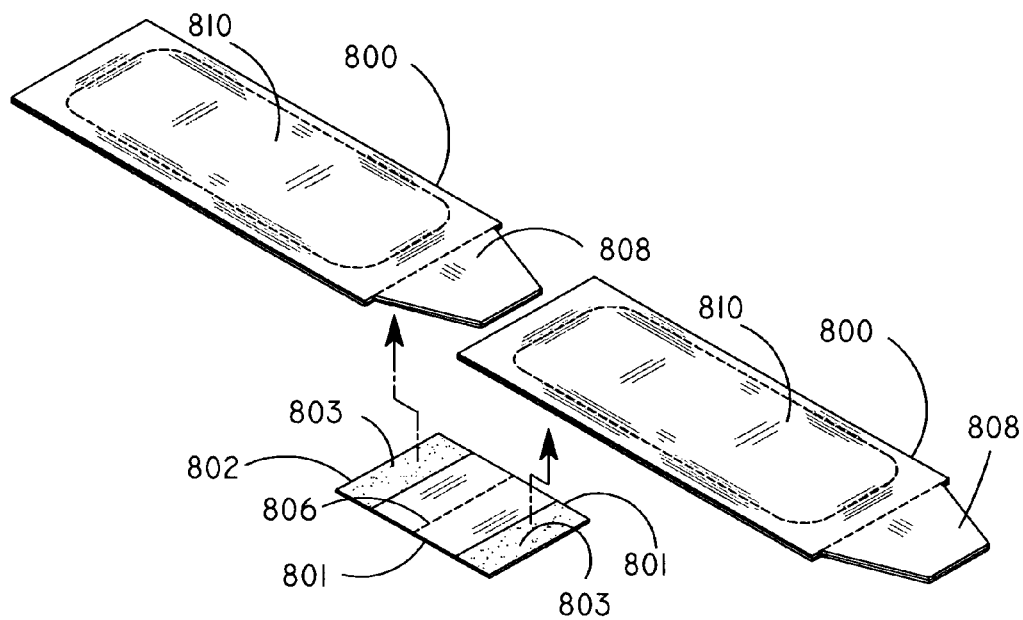
FIG. 23A is an exploded perspective view illustration of individual packages being aligned and attached to each other using attaching strips.

An exploded perspective view illustration of individual packages being aligned and attached using attaching strips is shown in FIG. 23A. The individual packages 800 are aligned along their lateral axis and attached to the attaching strips 802 using an adhesive 803 or other suitable bond. The attaching strips are preferably narrower than the width of the individual packages so as to form small locating means (e.g., a locating notch 804). The locating notches are defined by the side edges 801 of the attaching strip and the adjacent first end and second end of adjacent packages. These locating notches can be used to hold the packages as the adhesive strips are dispensed. An optional weakened detaching line 806 is included to help separate the packages as they are dispensed. The individual packages can overlap each other if desired. If overlapping, then it is preferred that only a portion of the first tabs 808 overlap the upper sheet 810 of the preceding package. The locating notches can be used on designs in which the individual packages are advanced. Such designs include the continuous roll dispensers which are described supra. In alternative embodiments, the attaching straps are attached to each other and formed from a continuous sheet of material.

Figure 23B:
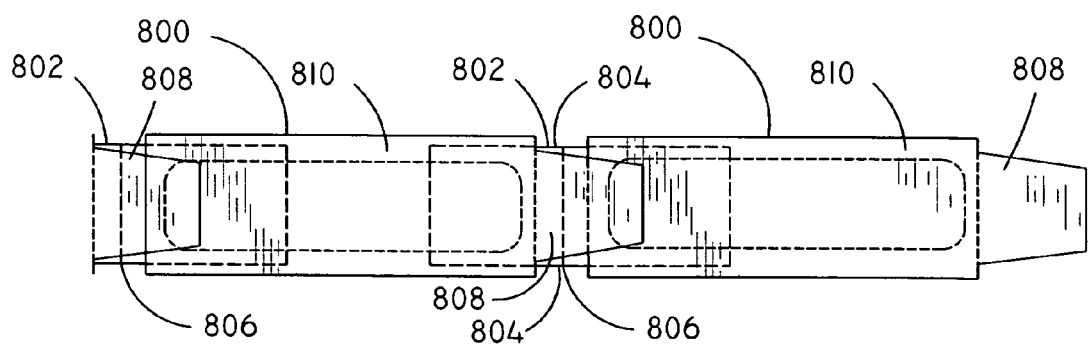
FIG. 23B is a top view illustration of the individual packages aligned and attached to each other as shown in FIG. 23A.

A top view illustration of the individual packages aligned and attached to each other as shown in FIG. 23A is shown in FIG. 23B. The optional locating notches 804 are formed between the packages by the combination of the attaching strips. The attaching strips are narrower than the width of the individual packages so as to form the locating notches. The locating notches may range in size from a small slit to any desirable length. The optional weakened detaching line is located on the attachment strip between the packages as desired. This design can also be used with other axial-pull bandage designs. Alternatively, the packages are removably attached to the attaching strips.

Figure 24:
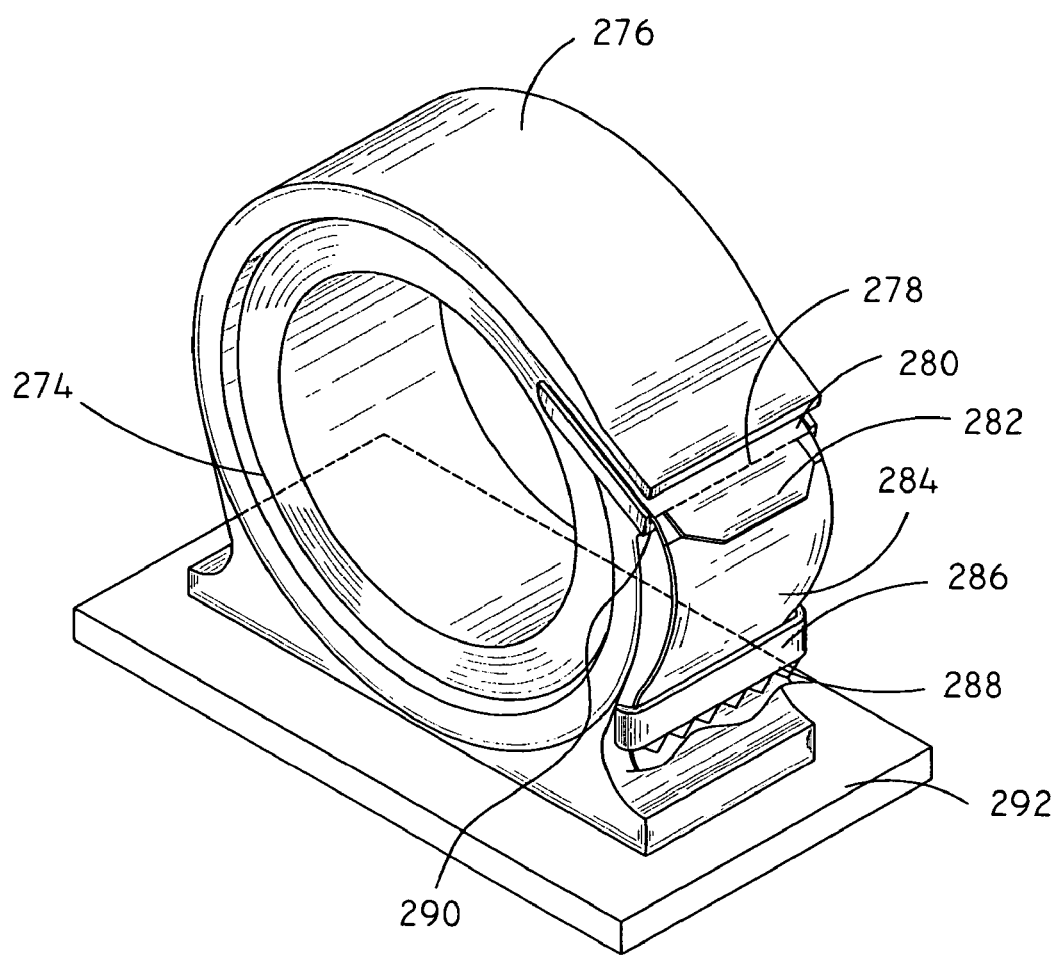
FIG. 24 is a perspective view illustration of an alternative dispenser that uses an optional external guide means suitable for use with the continuous roll dispensing pack.

A perspective view illustration of an alternative dispenser that uses an optional external guide means suitable for use with the continuous roll dispensing pack of FIGS. 23A and 23B is shown in FIG. 24. The continuous roll dispensing pack 274 is placed within a dispenser 276 such that individual adhesive strips can be dispensed by pulling on the individual first tabs 282. The weakened line 278 of the upper sheet is seen. After an adhesive strip is dispensed, a new package 280 is pulled into place by pulling on any of the upper sheet 284, the lower sheet, or the optional continuous sheet backing, or by pulling the release liner 292 (which now protrudes from the opened package, and is the preferred method). The empty packages are directed through an optional guide means, and if desired are cut by pulling the empty packages against a cutting means. The cutting means 286 may comprise a serrated strip 288 which can be placed as shown or can be optionally placed at the edge of the guide 290. Alternatively, the continuous sheet is scored or perforated so that it can be easily torn. The dispenser has an optional base 292 which provides sufficient stability. Additionally, the base can be weighed down. Dispensers are well known in the art. In alternative embodiments, the continuous roll dispensing pack can be placed within a supply spool/take-up spool dispenser (not shown). A friction means is included and restricts advancing movement of the roll. Suitable friction means include a mechanical friction element acting on the roll or an adhesive/cohesive which would stop the advancement of the roll. A stopping means is also included to help locate the first tab in the correct position for dispensing. A suitable stopping means comprises hooks or tabs which catch small notches which or other types of protrusions which are placed between or on the individual packages.

Figure 25A:
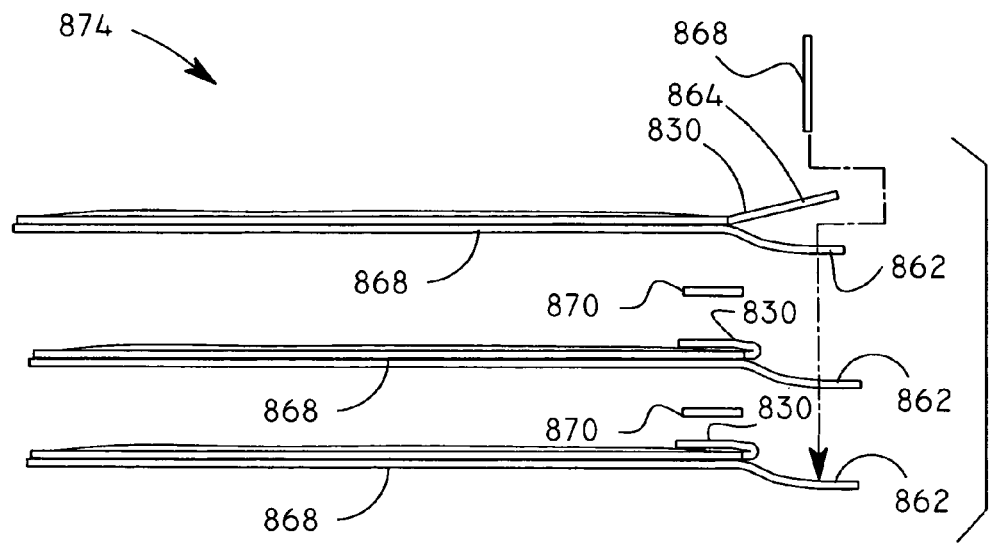
FIG. 25A is an exploded side view illustration of a third embodiment of a dispensing pack.

An exploded side view illustration of a third embodiment of a dispensing pack is shown in FIG. 25A. The dispensing pack 874 comprises a plurality of packages 860 (such as are described in the second major embodiment of the present invention) which are aligned and attached to each other along their second tabs 862 using an optional staple 868 or other suitable method (e.g., adhesives, pressure, welding, etc.) which is suitable for the material being used. The dispensing pack can be placed within a dispenser adapted to support and contain the dispensing pack. The individual first tabs 864 are optionally folded back over themselves and releasably attached to the lower sheet 872 of the preceding package using a light tack adhesive 870 such that when a first package is opened the first tab of a succeeding package unfolds and separates from the lower sheet of previous package such that it is suitable for grasping by a user. In alternative embodiments, the first tab of the upper most sheet is folded over itself.

Figure 25B:
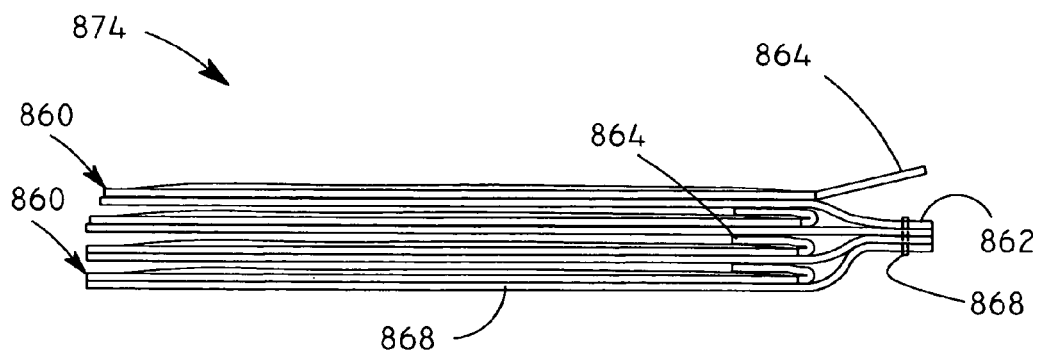
FIG. 25B is a side view illustration of the third embodiment of the dispensing pack with the packages attached to each other.

A side view illustration of the third embodiment of the dispensing pack with the packages attached to each other is shown in FIG. 25B. The dispensing pack 874 comprises a plurality of packages 860 which are aligned and attached to each other along their second tabs 862 using a staple 868 or other suitable method to attach them to each other. The dispensing pack can be placed within a dispenser adapted to support and contain the dispensing pack. The individual first tabs 864 are optionally folded back over themselves and releasably attached to the lower sheet 868 of the preceding package using a light tack adhesive 870 such that when a first package is opened the first tab of a succeeding package unfolds and separates from the lower sheet of previous package such that it is suitable for grasping by a user. The first tab of the upper most sheet is optionally not folded over itself.

Figure 26A:
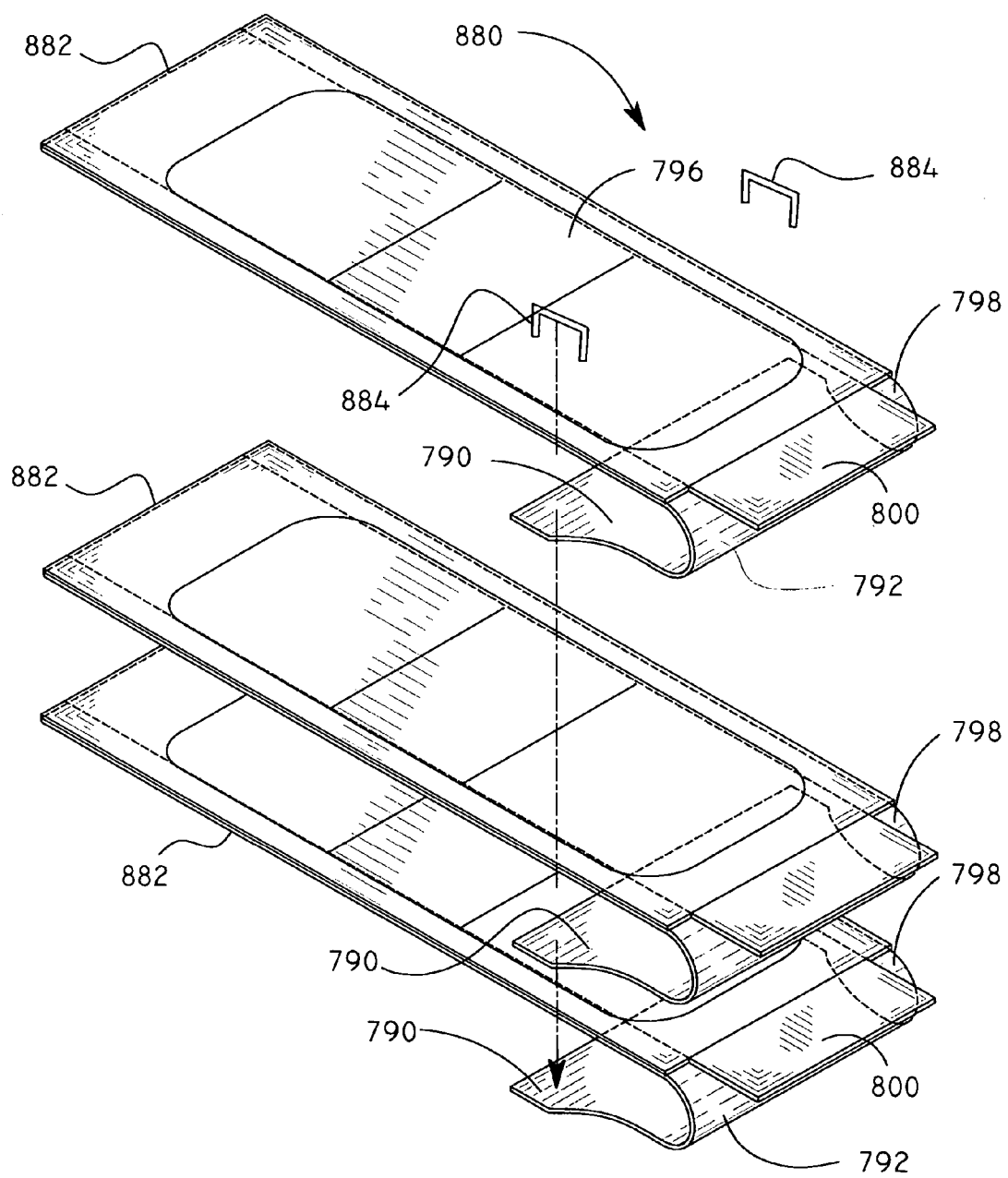
FIG. 26A is an exploded perspective view illustration of the fourth embodiment of a dispensing pack.

An exploded perspective view illustration of the fourth embodiment of a dispensing pack is shown in FIG. 26A. The dispensing pack 880 comprises a plurality of packages 882 (which are similar to the package which is shown in FIG. 18 above and described in the corresponding text) which are aligned and attached to each other. The second tabs are folded back such that the transverse extensions 790 or the second tabs or a package can be attached to the of the transverse extension of the second tab of an adjacent package, using a locating means which comprises an optional staple 884 or other suitable method (e.g., adhesives, pressure, welding, etc.) which is suitable for the material being used. This will allow the first and lower sheets to slide relative to the second tabs when the package is opened. The second tabs are optionally attached to a first locating means which is not shown. Likewise, an optional second locating means can be used. The dispensing pack can be placed within an optional dispenser adapted to support and contain the dispensing pack. The individual first tabs are optionally folded back over themselves and releasably attached to the lower sheet of the preceding package using a light tack adhesive. The first tab of the upper most sheet is optionally not folded over itself.

Figure 26B:
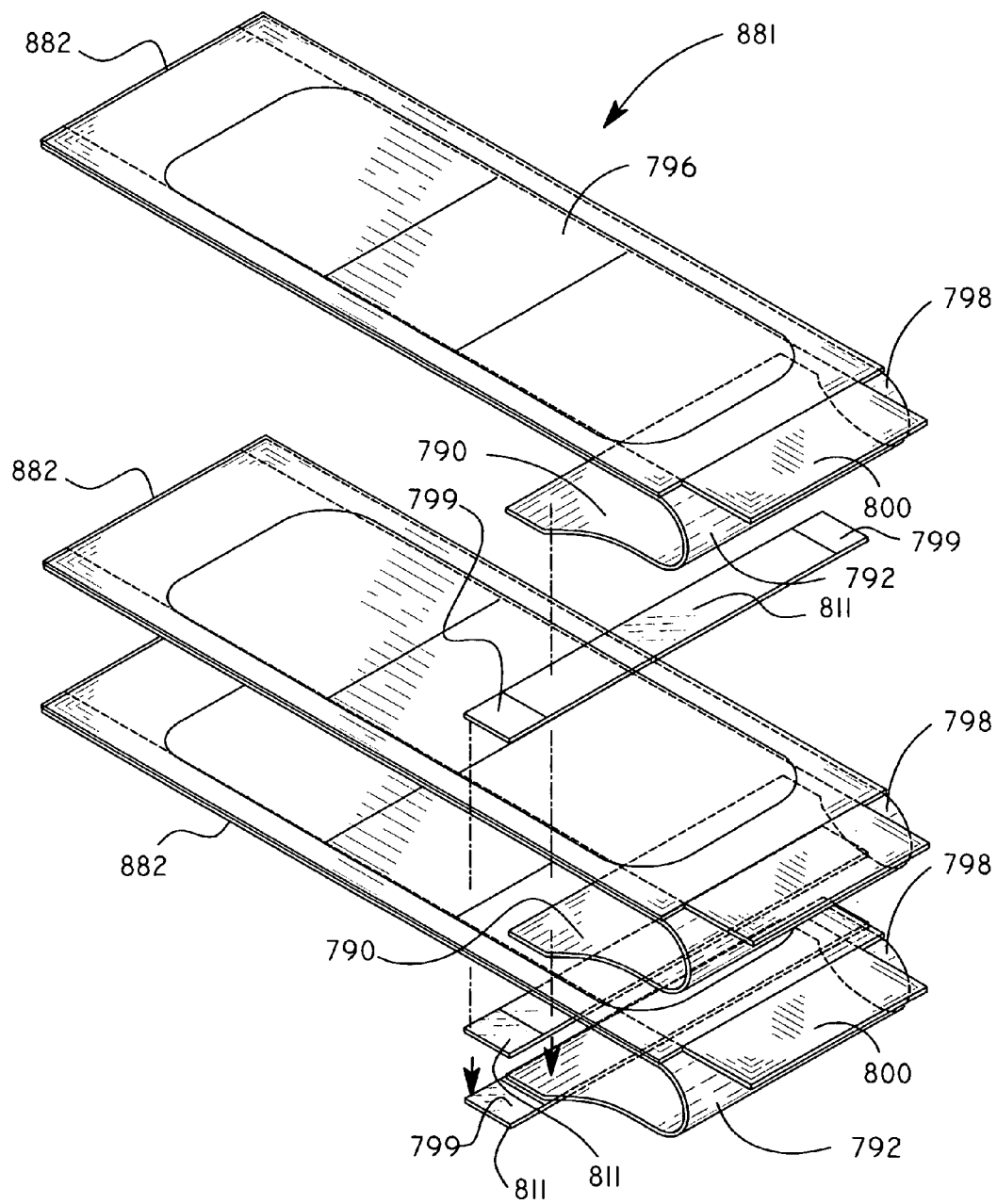
FIG. 26B is an exploded perspective view illustration of a fifth embodiment of a dispensing pack.

An exploded perspective view illustration or a fifth embodiment of a dispensing pack is shown in FIG. 26B. The dispensing pack 881 comprises a plurality of packages 882 (which are similar to the package which is shown in FIG. 18 above and described in the corresponding text) which are aligned and attached to each other but uses a locating means which comprises an attachment strip 811 to attach packages to each other. The attachment strip can be attached to the second tab 792 directly, or to the optional transverse extension appendages 190 of the second tabs, using adhesives, staples, or other suitable method which is suitable for the material being used. The second tabs are folded back upon themselves and attached to the attachment strip such that the end regions 799 of the superposing adjacent attachment strips can be attached to each other using an adhesive or other suitable means. This will allow the upper sheet 796 and lower sheet 798, to slide relative to the second tabs when the package is opened. The attachment strips are optionally attached to a first locating means which is not shown. Likewise, an optional second locating means can be used. The dispensing pack can be placed within an optional dispenser adapted to support and contain the dispensing pack. The individual first tabs are optionally folded back over themselves and releasably attached to the lower sheet of the preceding package using a light tack adhesive. The first tab of the upper most package is optionally not folded over itself. If using an adhesive to attach the attachment strips to the second tabs, then is desirable to use optional transverse extension appendages as they will reduce the likelihood of inadvertent adhesion between the first and/or lower sheet and the attachment strip. Those parts of the attachment strip which extend from the exterior periphery of the package and are suitable for attachment to a locating means or a dispensing package will be considered to be transverse extension appendages. In alternative embodiments, the transverse extension appendages of the lower sheet are not provided, and the attachment strips are directly attached to the second tab using any suitable means (e.g., adhesives, etc.).

In yet other alternative embodiments, the second tabs are not folded over themselves, and therefore extend directly in front of the lower sheet and are attached to the attachment tabs using any suitable method as discussed elsewhere in this document.

In yet other alternative embodiments, the second tab includes transverse side extensions, but, the second tab is not folded over itself. The transverse side extensions of adjacent packages are attached to each other so as to form an opening through which a package (or parts thereof) can pass through as the package is opened.

A perspective view illustration of a sixth embodiment of a dispensing pack is shown in FIG. 27A. The dispensing pack 306 is formed from a plurality of substantially superposed packages 300, (which are shown and described in the first major embodiment of the present invention) which are attached to or aligned with one another. The first tabs 296 are not attached to each other and are separated from the packages at weakened line 298. The individual packages 300 are formed from one or more sheets of material either attached to each other, held adjacent to each other, or folded in an accordion-like fashion so as to form a plurality of individual packages. In one embodiment, the dispensing pack is constructed from a single sheet of material folded in an accordion-like fashion, so as to form both the upper sheet 302 and the lower sheet 304 of the package. In another embodiment, the dispensing pack is formed from a single sheet of material that forms the lower sheet. The upper sheet is formed from individual sheets that are attached to the continuous sheet so as to form the package. In another embodiment, the dispensing pack is formed from two continuous sheets of material that are folded in an accordion-like fashion so as to form the packages. One sheet of material forms the upper sheet, while the other sheet forms the lower sheet. In another embodiment, the dispensing pack is formed from individual packages which are aligned with and stacked upon each other. In all embodiments of the dispensing pack 306 the individual sheets may be folded either along their longitudinal or lateral axis. In other alternative embodiments, in order to avoid substantial package deformation, the individual packages are held in close proximity by a locating means, which positions the packages in a desired location. Suitable locating means may comprise adhesive, staples, or other means which position individual packages in a desired position (e.g., a piece of paper bonded to several individual packages to form a dispensing pack). In alternative embodiments, either or both the upper sheet and the lower sheet are extended. A plurality of packages are then superposed upon each other and held in position by a staple which is inserted proximate to or through the second tab of the package.

In yet other alternative embodiments, the second tab includes transverse side extensions, but, the second tab is not folded over itself. The transverse side extensions of adjacent packages are attached to each other so as to form an opening through which a package (or parts thereof) can pass through as the package is opened A perspective view illustration of a seventh embodiment of a dispensing pack is shown in FIG. 27B. The dispensing pack 900 is formed from a plurality of substantially superimposed packages 902, (which are shown and described in the second major embodiment of the present invention) which are attached to or aligned with, and stacked upon one another. The individual packages 904 are either attached to each other or held adjacent. The second tab 906 of the lower sheet 910 is folded back over itself and has transverse extensions 908 which are either attached to each other or held adjacent to each other by suitable locating means (e.g., adhesives, staples etc.). In alternative embodiments, in order to avoid substantial package deformation, the individual packages are held in close proximity by a locating means, which positions the packages in a desired location. Suitable locating means may comprise adhesives, staples or other means which position individual packages in a desired position (e.g., a sheet of paper bonded to several individual packages to form a dispensing pack). In yet other alternative embodiments, a piece of paper or other blocking type member is placed between the transverse extensions of the second tabs. In yet other alternative embodiments, the transverse extensions of the second tab are extended.

A front side view illustration of an eighth embodiment of a dispensing pack adapted to dispense adhesive strips from opposing sides is shown in FIG. 28A. The individual packages 310 that comprise the dispensing pack 312 are located with their first tabs 314 opposing each other such that the adhesive strips or bandages which are adjacent to each other are dispensed from opposite ends of the dispensing pack. Additionally, if different-sized adhesive strips or bandages are used, then to aid the user in discerning the size of the adhesive strip or bandage, the individual packages that make up the dispensing pack are located with the pull covers opposing each other such that different-sized adhesive strips or bandages are located on and dispensed from opposite ends of the dispensing pack. The inner tab member is sized so that it is smaller than the first tab, so that the upper sheet can be sealed to the lower sheet and form a bond around the outer periphery of the inner tab member. This forms the first tab and will insure sterility if so desired. The first tabs are separated from the packages at weakened lines 308.

A front side view illustration of a ninth embodiment of a dispensing pack adapted to dispense adhesive strips from opposing sides is shown in FIG. 28B. The individual packages 920 that comprise the dispensing pack 922 are located with their first tabs 924 opposing each other such that the adhesive strips or bandages which are adjacent to each other are dispensed from opposite ends of the dispensing pack. Additionally, if different-sized adhesive strips or bandages are used, then to aid the user in discerning the size of the adhesive strip or bandage, the individual packages that make up the dispensing pack are located with the pull covers opposing each other such that different-sized adhesive strips or bandages are located on and dispensed from opposite ends of the dispensing pack.

Although the dispensing pack may, if desired, dispense individual adhesive strips without the aid of a suitable container means, it is preferable that the dispensing pack dispense adhesive strips while contained within a suitable container means, as illustrated and described hereinbelow in FIGS. 29 through 37E. Each scheme will now be described in more detail.

Figure 29:
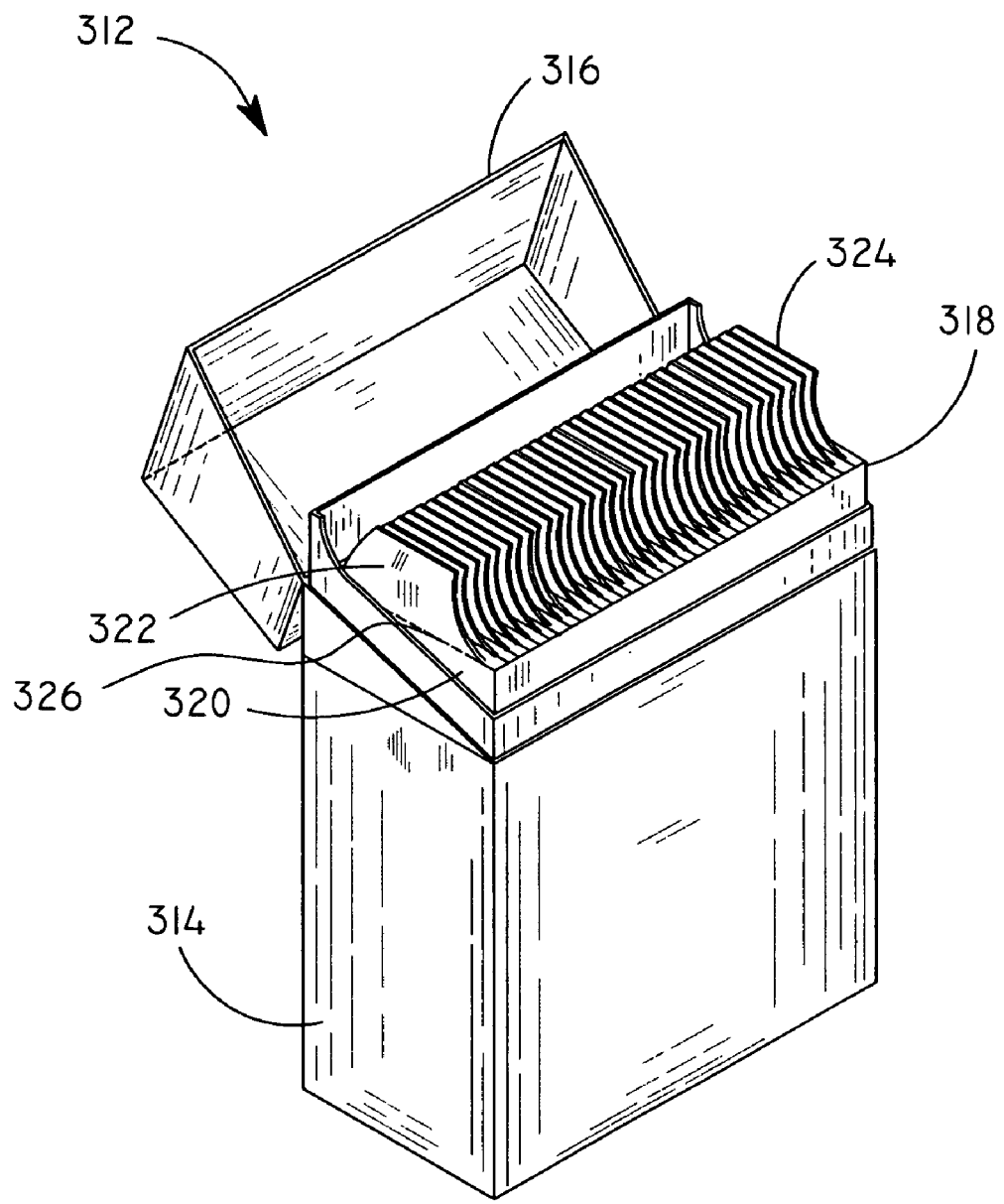
FIG. 29 is a perspective view illustration of a first embodiment of a container assembly which uses a "flip-box"

A perspective view illustration of a first embodiment of a container assembly which uses a "flip-box" is shown in FIG. 29. The container 312 is a folding-top-type box (also known as a "flip-box") which comprises a body 314 and an attached lid 316. The container comprises one or more dispensing packs 318, wherein each dispensing pack comprises a plurality of packages 320 placed such that the first tabs 322 and adhesive strips are easily removed from the package. The lid is hingedly attached to the body of the container such that the first tabs 324 are easily grasped by the user when the lid 316 is opened and separated from the individual packages at the weakened line 326. The dispensing pack is preferably attached to the body of the container using a heat glue or other suitable means (such as a locking-tab type mechanism). Such devices are commonly known as cigarette packages, and more particularly as "hard-packs," "crush-proof boxes," or "hinged-lid packages." See for example U.S. Pat. Nos. 4,852, 734 and 3,874,581, both of which are incorporated herein by reference in their entirety. The second tab is optional.

Figure 30:
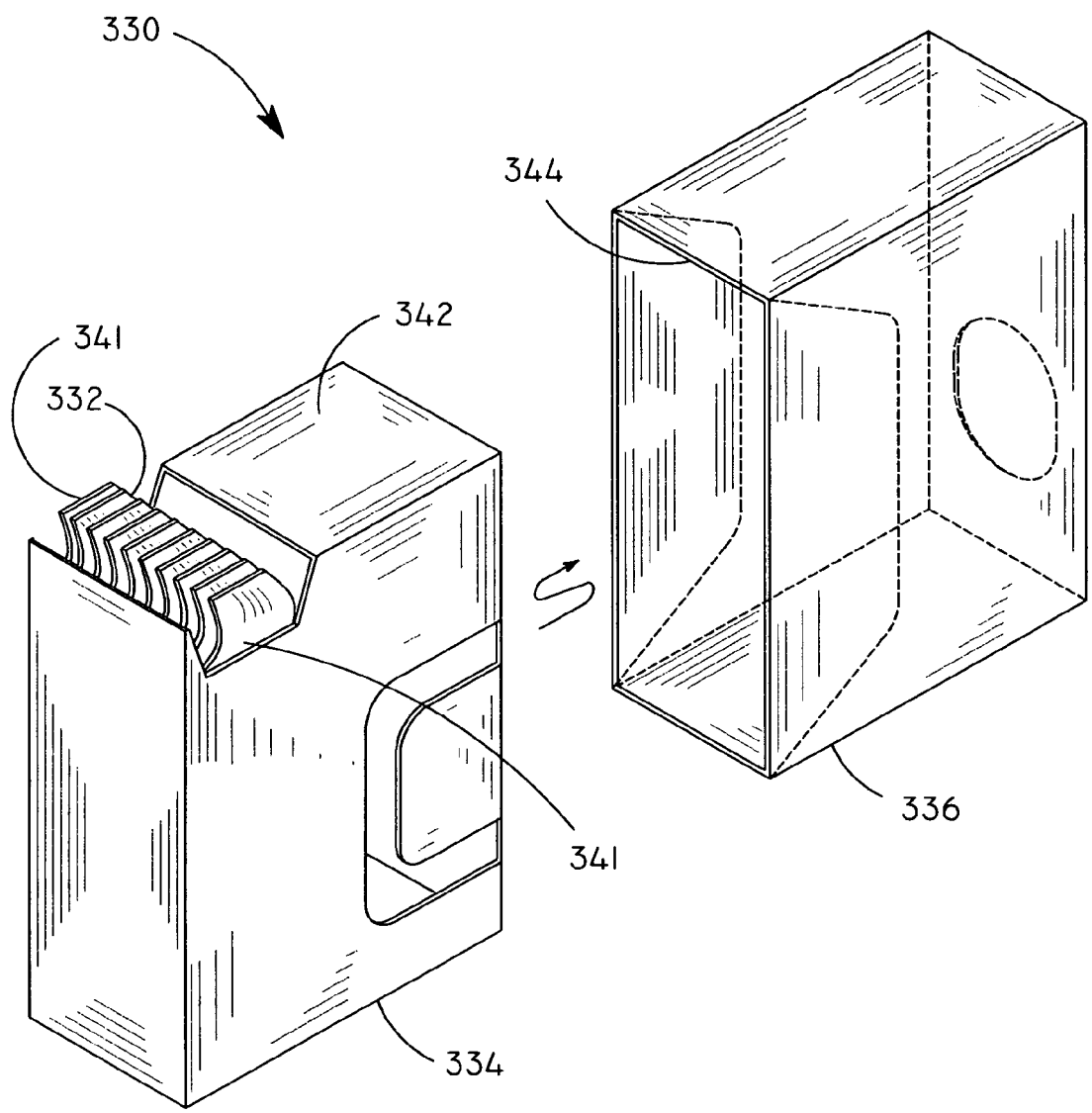
FIG. 30 is a perspective view illustration of a second embodiment of a container assembly incorporating a sliding-box.

A perspective view illustration of a second embodiment of a container assembly incorporating a sliding box is shown in FIG. 30. The sliding-box-type container 330 (hereinafter sliding box) comprises one or more dispensing packs 332. The sliding box and its structure are well known in the art. See, for example, U.S. Pat. No. 5,080,227, to Focke, entitled "Pack made of thin cardboard, especially for cigarettes," incorporated herein by reference in its entirety. The sliding-box container comprises an inner section 334 (also known as a "box part") and an outer section 336 (also known as a "casing"), both of which are slideably located relative to each other. The inner section holds the dispensing pack such that the individual first tabs 341 are easy to grasp. The dispensing pack is preferably attached to the inner section using a suitable means such as an adhesive (e.g. heat glue), or a locking-tab means. The inner section slides into a void located in the outer section. The inner section includes an opening that allows the user to grasp the first tab 341. In the preferred embodiment, the first tabs are made from a flexible material, and either or both of them extend slightly beyond the top 342 of the inner section so that the first tabs are easy to grasp by the user. The first tabs and/or the pull covers preferably include an angle cut into the side that contacts the upper opposed end 344 of the outer section so that the first tabs and/or the pull covers fold slightly and allow the outer section to enclose the inner section when the slide box type container is closed. In use, the inner section extends outward from the outer section enough so as to fully expose the individual first tabs and/or the pull covers of the dispensing pack.

Figure 31:
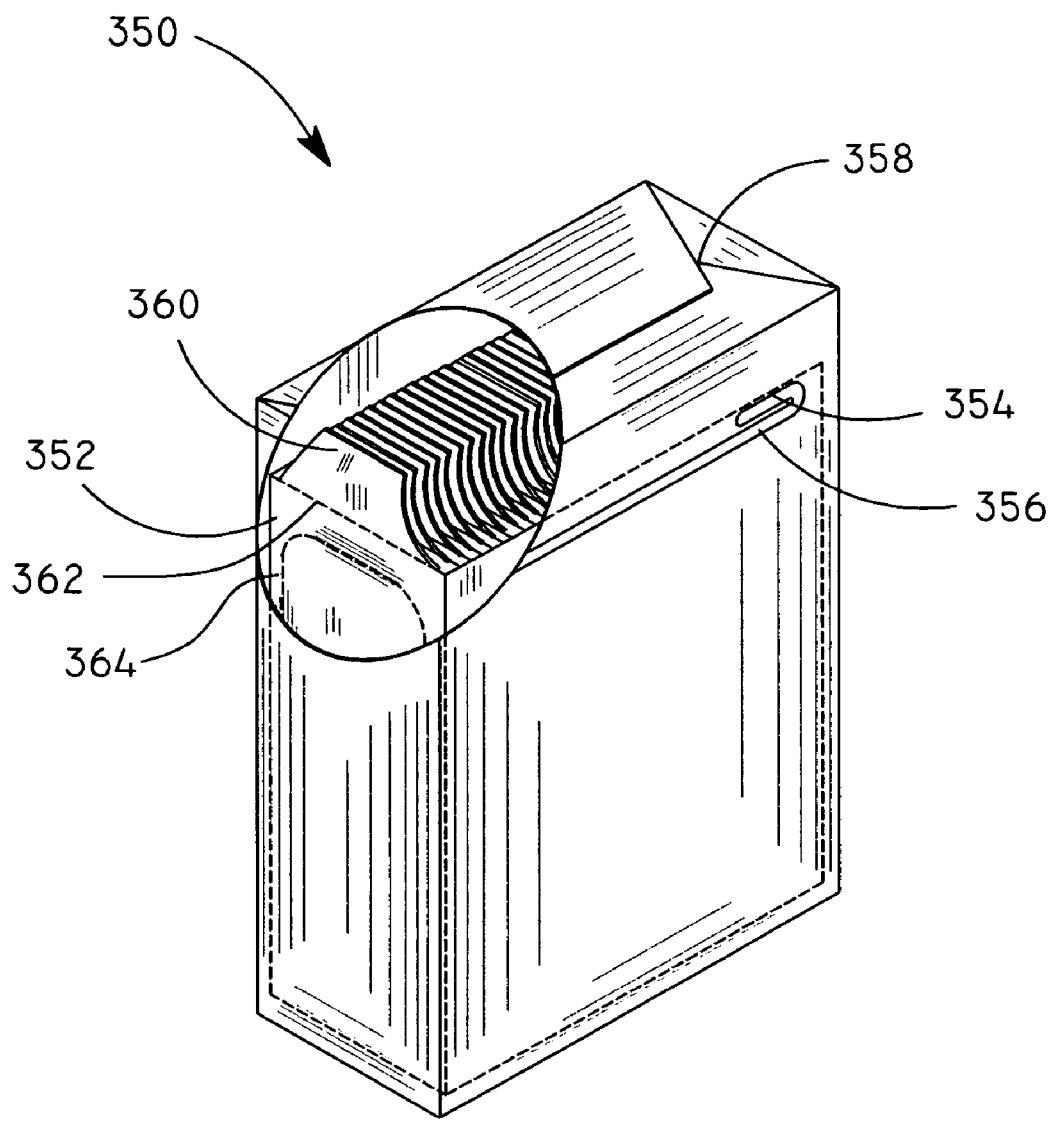
FIG. 31 is a semi-cutaway perspective view illustration of a third embodiment of a container assembly.

A semi-cutaway perspective view illustration of a third embodiment of a container assembly is shown in FIG. 31. The container 350 is a flexible cover that encloses the dispensing pack 352. Such packages are well known in the art and are often referred to as "soft-packs." The container comprises a tear tab 354 which works with a tear cord 356 located adjacent to the tear tab as shown. Alternatively, a weakened line (e.g., scoring, thinning, etc.) can be used. To open the package, the tear tab is pulled back over itself so that the container cover 358 is either opened or removed from the container, which exposes the first tabs 360 and allows for the user to remove the first tab 360 and adhesive strip from the dispensing pack. The upper sheet 364 and the upper sheet's weakened line 362 are seen.

Figure 32A:
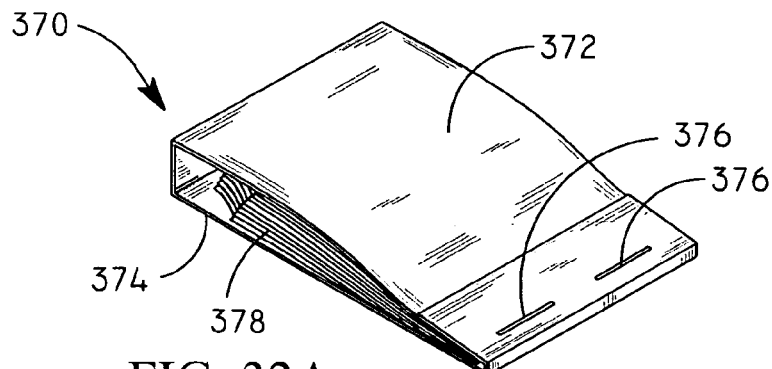
FIG. 32A is a perspective view illustration of a fourth embodiment of a container assembly incorporating a flip-cover-type box with the cover being in the closed position.

A perspective view illustration of a fourth embodiment of a container assembly incorporating a flip cover-type box with the cover being in the closed position is shown in FIG. 32A. The flipcover-type (or matchbook-like) container 370 is wrapped around and encloses one or more dispensing packs 378. The container is constructed from a single sheet of material (e.g., thin cardboard) folded to form a back cover 374 and a re-sealable front cover 372. The dispensing pack is secured to the back cover using a fastener such as a staple 376 or other suitable means such as adhesive.

Figure 32B:
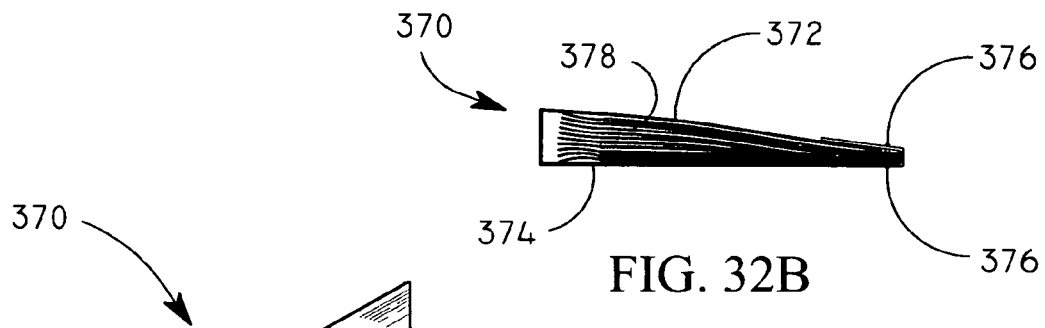
FIG. 32B is a side view illustration of the container assembly of FIG. 32A.

A side view illustration of the container assembly of FIG. 32A, is shown in FIG. 32B. The front cover 372 is retained in the closed position by a portion of the back cover 374 which wraps around and is attached to the dispensing pack.

Figure 32C:
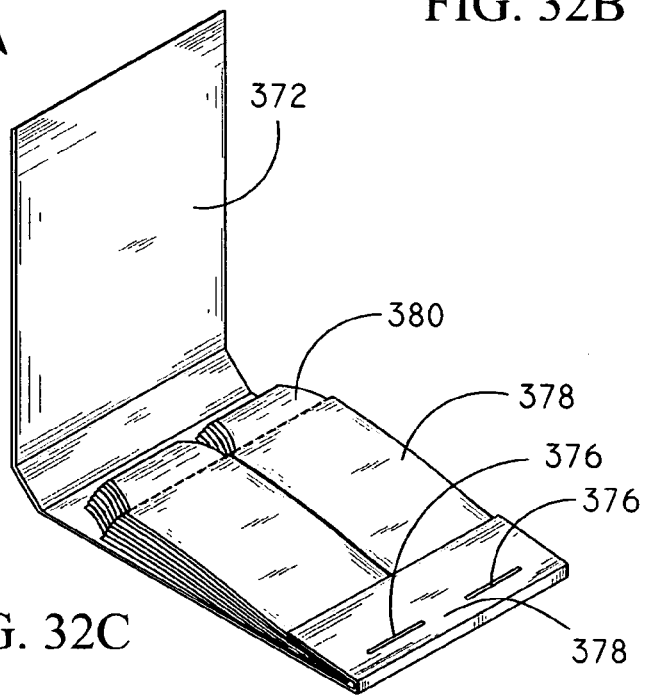
FIG. 32C is a perspective view illustration of the container assembly of FIG. 32A with the cover being in a semi-open position.

A perspective view illustration of the container assembly of FIG. 32A with the cover being in a semi-open position is shown in FIG. 32C. The front cover 372 is rotatably located relative to the back cover 374 such that the front cover is able to swing in excess of 180 degrees (and preferably swings about 270 degrees or more) from the front cover's closed position, so that the front cover does not come into contact with the adhesive strips as they are being removed from the dispensing pack. Additionally, the front cover is preferably adapted to allow easy access to the first tabs 380. Alternatively, the bandage packages can be reversed so that the first tabs are located proximate to the base flap 378.

Figures 33A, 33B:
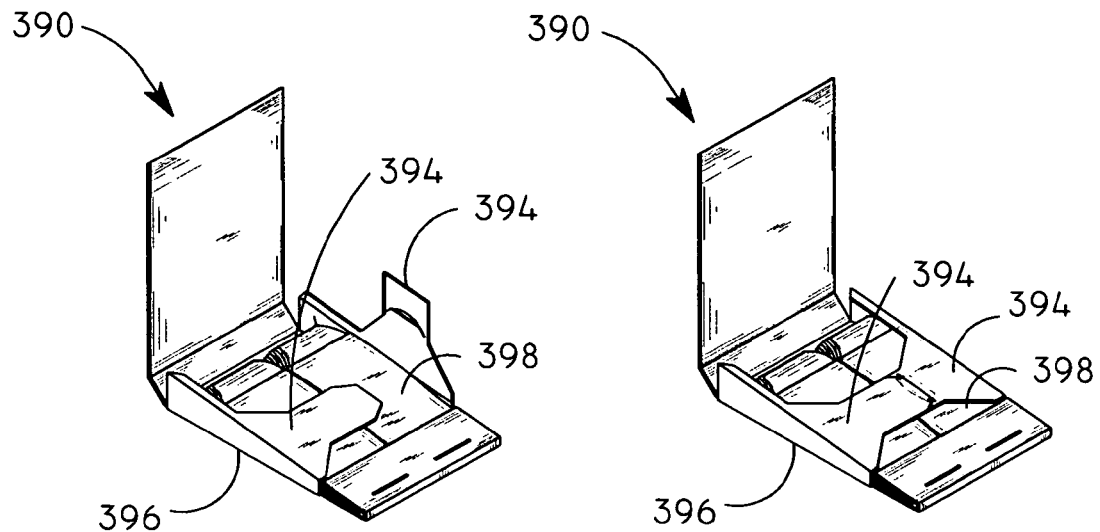
FIG. 33A is a perspective view illustration of a fifth embodiment of a container assembly incorporating a flip-cover-type box including side members, with the cover and one side member being in the semi-open position.
FIG. 33B is a perspective view illustration of the container assembly of FIG. 33A with side members secured to each other.

A perspective view illustration of a fifth embodiment of a container assembly incorporating a flip cover-type box including side members, with the cover and one side member being in the semi-open position is shown in FIG. 33A. The flip cover-type container 390 is substantially similar to the flipcover-type container illustrated in FIGS. 32A through 32C described supra, with a difference being the addition of a retention means such as side members 394 which are articulated to the rear cover 396. The side members can be attached to each other using an adhesive tape, a locking tab, or other suitable means. This type of container is known in the art.

A perspective view illustration of the container assembly of FIG. 33A with side members secured to each other is shown in FIG. 33B. The side members 394 are folded around the dispensing packs 398 and are secured to each other using a suitable attachment means (e.g., a tab, adhesive, adhesive tape, staple, pressure bond, etc.) so that they conceal the dispensing pack contained within the container assembly 390. In alternative embodiments, side members are attached to the rear cover 396 using a weakened line (e.g., scoring or perforating) so that the side member can be removed after the container assembly is initially opened.

Figure 33C:
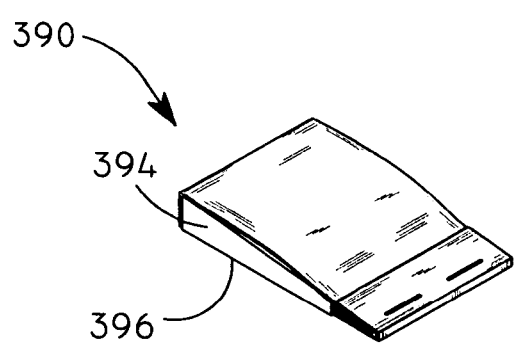
FIG. 33C is a perspective view illustration of the container assembly of FIG. 33A with the cover in the closed position.

A perspective view illustration of the container assembly of FIG. 33A with the cover in the closed position is shown in FIG. 33C. The side members 394 conceal and secure the dispensing packs 398 held within the container assembly 390, thus making the container assembly suitable for store displays and merchandising fixtures without requiring additional packaging materials. The dispenser assembly 390 may optionally be oriented in the vertical position for hanging on display rails, storage rails, or posts.

Figure 34A:
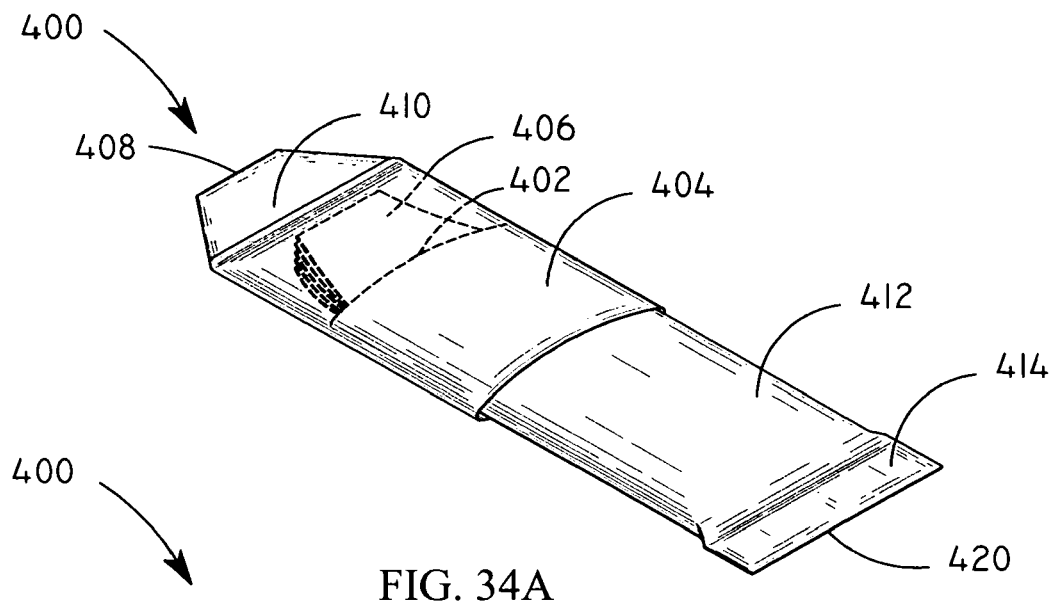
FIG. 34A is a perspective view illustration of a sixth embodiment of a container assembly incorporating a flexible outer wrapper having a body portion and a removable top portion.

A perspective view illustration of a sixth embodiment of a container assembly incorporating a flexible outer wrapper having a body portion and a removable top portion is shown in FIG. 34A. The container assembly 400 comprises a flexible body portion 412 and a removable top portion 404. The flexible body portion is formed from a flexible sheet of material (e.g., treated paper) wrapped around and securely attached to a plurality of packages to form a dispensing pack. The flexible body portion comprises an open end 402 and a closed end 420. The closed end of the body portion is flattened and attached to itself (using adhesive, etc.) to seal one end of the body portion and to form a first holding tab 414 which is suitable for grasping. The first tabs 406 of the dispensing pack extend outward from the open end of the body portion so that they are easy to grasp. The dispensing pack is secured to the body portion using any suitable bonding method (e.g., adhesive, staples, pressure, etc.).

The top portion comprises a flexible cylindrical member having an open end 416 and a closed end 410. The top portion is constructed from the same material as the body portion. The closed end of the top portion is flattened and attached to itself (using adhesive, etc.) so as to seal one end of the top portion and to form a second holding tab 408 which is suitable for grasping. The open end of the top portion has an inner circumference which is slightly larger than the exterior circumference of the body portion so that the cover portion can be slidably attached to the body portion. In alternative embodiments the top portion may have a slight conical form to better secure the top portion to the body portion.

In alternative embodiments, the closed end of the top portion comprises a weakened line (e.g., scoring, perforating or adhesive) so that the closed end can be opened. In use, the pull tabs are accessed by slidably repositioning the top portion along the longitudinal axis of the body portion so that the pull tabs of the dispensing pack extend outward from the now open closed end of the top portion.

Figure 34B:
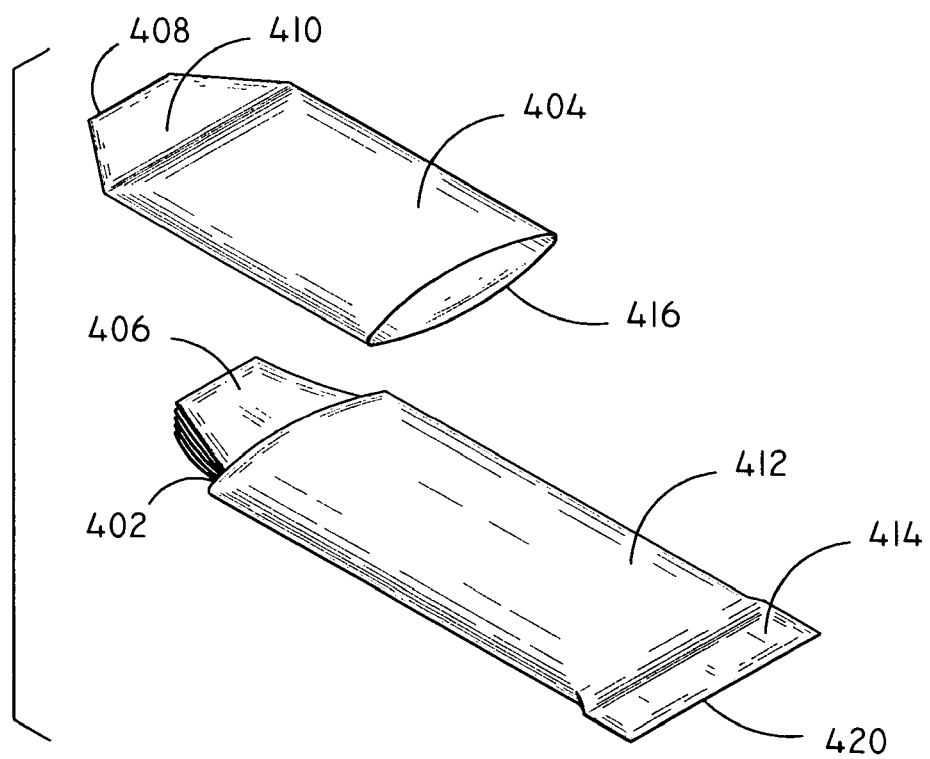
FIG. 34B is a perspective view illustration of the container assembly of FIG. 34A with the top portion removed.

A perspective view illustration of the container assembly of FIG. 34A with the top portion removed is shown in FIG. 34B. Removing the top portion exposes, and allows easy access to, the first tabs 406 of the dispensing pack contained within the body portion.

Figure 35A:
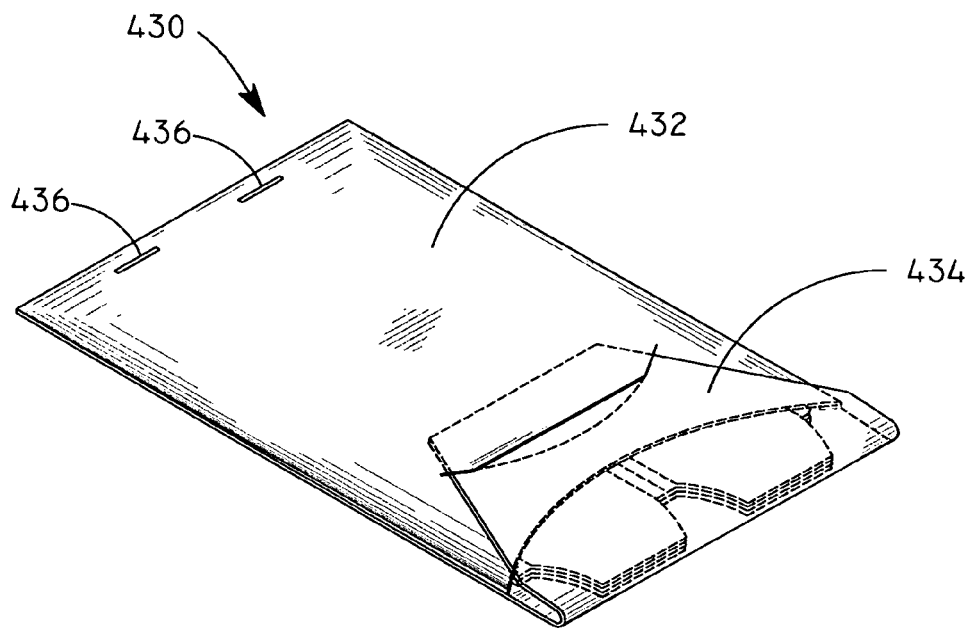
FIGS. 35A and 35B are perspective view illustrations of a seventh embodiment of a container assembly incorporating a semi-rigid body portion and a re-sealable cover in the closed and open positions respectively.
Figure 35B:
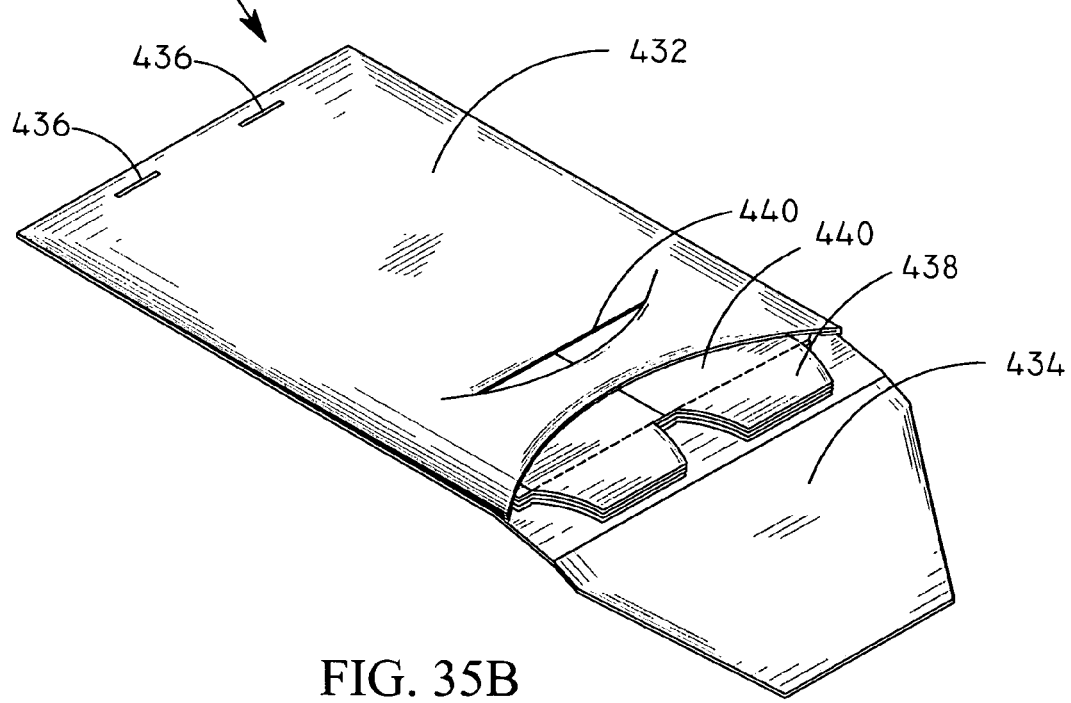

A perspective view illustration of a seventh embodiment of a container assembly incorporating a semi-rigid body portion and a re-sealable cover in the closed and open positions respectively, is shown in FIGS. 35A and 35B. The container 430 comprises a body 432 with a re-sealable cover 434. The container comprises one or more dispensing packs 440, wherein each dispensing pack contains a plurality of packages, situated such that the first tabs 438 and adhesive strips are easily removed from the package. The packages can be made in accordance with the first or second major embodiment of the present invention. The cover is articulated with the body of the container such that the first tabs are easily grasped by the user when the cover is opened. The dispensing pack is attached to the body using any suitable method (e.g., staples 436, adhesive, pressure bonding, etc.). A slot 442 is provided to releasably secure the cover in the closed position. Alternatively, a re-sealable adhesive or other suitable method can be used. An optional U-shaped slit (not shown) is provided between the body and the cover to prevent the cover from folding back upon itself during removal of the adhesive strips from the dispensing pack.

Figure 36A:
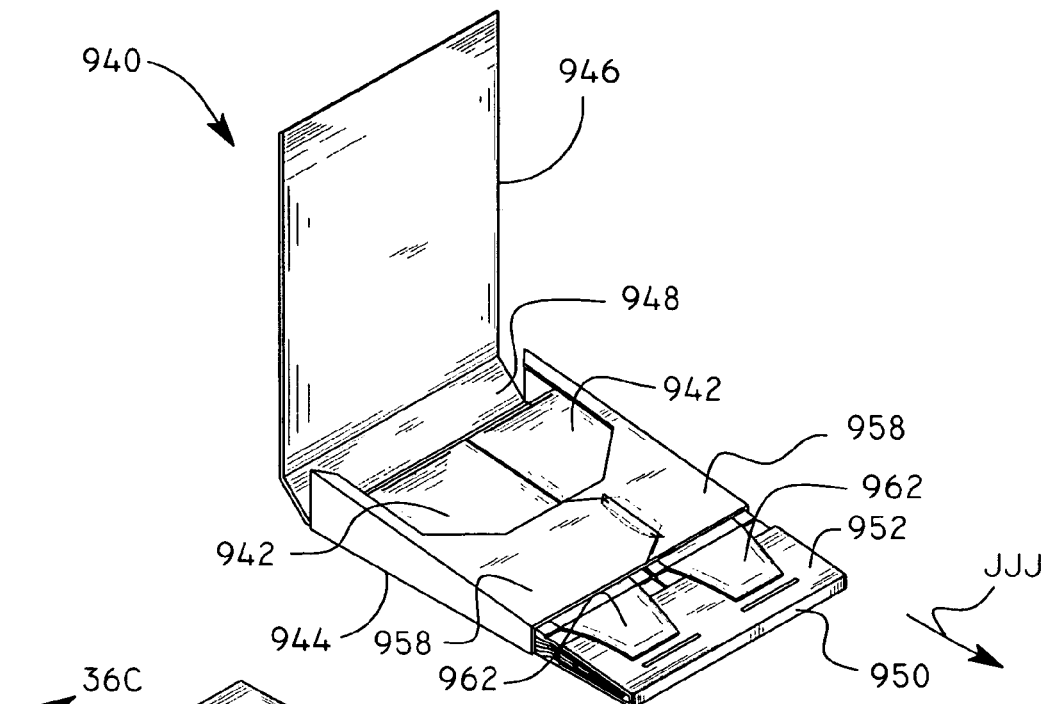
FIG. 36A is a perspective view illustration of an eighth embodiment of a container assembly incorporating a flip-cover-type box with the cover being in the semi open position.

A perspective view illustration of an eighth embodiment of a container assembly incorporating a flip-cover-type box with the cover being in the semi open position is shown in FIG. 36A.

The flipcover-type (or matchbook-like container) container 940 is wrapped around and encloses one or more dispensing packs 92. The preferred dispensing pack is of the type shown in FIGS. 19A-19B, 20A-20B and 25A-25B and described in the corresponding text. As illustrated, the dispensing pack shown is similar to the dispensing pack shown in FIGS. 25A-25B. Alternatively, other types of dispensing packs can be used as will be discussed infra. The container is constructed from a single sheet of material (e.g., thin cardboard) folded to form a back cover 944, a top portion 948, a minor portion 950, a closure portion 952, and a re-sealable front cover (or lid) 946. The dispensing pack is secured to both the back cover and the closure portion using a fastener such as a staple 954 or other suitable means such as an adhesive. An optional locating means such as side members 958 which are articulated to the rear cover are used to locate the individual packages in a desired position for dispensing. Moreover, the side members conceal and secure the dispensing packs held within the container assembly thus making the container assembly suitable for store-displays and merchandising fixtures without requiring additional packaging materials.

The optional side members 958 are folded around the dispensing packs and are secured to each other using a suitable attachment means such as a notch and tab-type design 960 shown or any other suitable means (e.g., a tab, adhesive, adhesive tape, staple, pressure bond, etc.) so that they locate the dispensing pack contained within the container assembly in a desired position for dispensing. The side member attachment means is optionally releasable and reattachable so that the side members can be opened in case the first tabs jam in use. In alternative embodiments, side members are attached to the rear cover using a weakened line (e.g., scoring or perforating) so that the side member can be removed after the container assembly is initially opened. In use the cover can be in the semi open position, or optionally in an almost closed position depending on whether side members are incorporated into the design. The first tabs 962 are seen extending from the dispensing packs. In use, the first tab is pulled, optionally, in the direction indicated by arrows JJJ. The dispenser assembly may optionally be oriented in the vertical position for hanging on display rails, storage rails or posts. In alternative embodiments the dispenser can have small cutouts which help it stand upright on all or a portion of the minor portion.

In alternative embodiments, side members are attached to the rear cover 944 using a weakened line (e.g., scoring or perforating) so that the side member can be removed after the container assembly is initially opened.

In alternative embodiments only one dispensing pack is used. While, in yet other alternative embodiments, two or more dispensing packs are aligned side by side within the container assembly as shown.

Figure 36B:
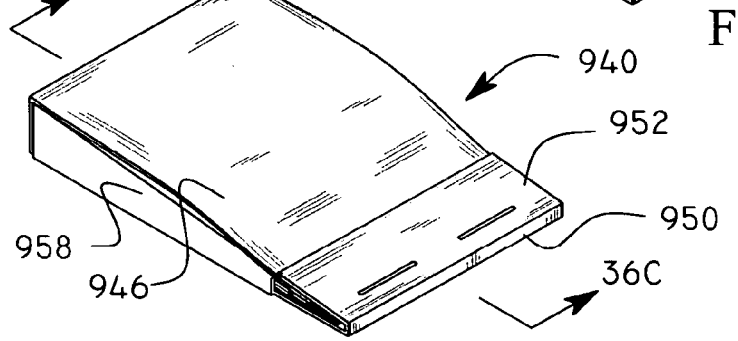
FIG. 36B is a perspective view illustration of the container assembly of FIG. 36A with the front cover in the closed position.

A perspective view illustration of the container assembly of FIG. 36A with the front cover in the closed position is shown in FIG. 36B. The front cover is held in the closed position by tucking it under the closure portion. The first tabs are optionally folded back over themselves before the front cover is closed as will be discussed infra.

Figure 36C:
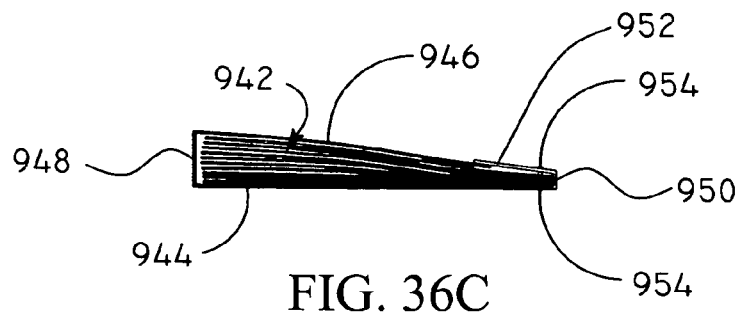
FIG. 36C is a side view illustration of the container assembly of FIG. 36A taken along line 36C-36C of FIG. 36B.

A cross sectional side view illustration of the container assembly of FIG. 36B taken along line 36C-36C of FIG. 36B is shown in FIG. 36C. A plurality of packages is seen within the container. The first tabs are not shown. The front cover is in the closed position.

Figure 36D:
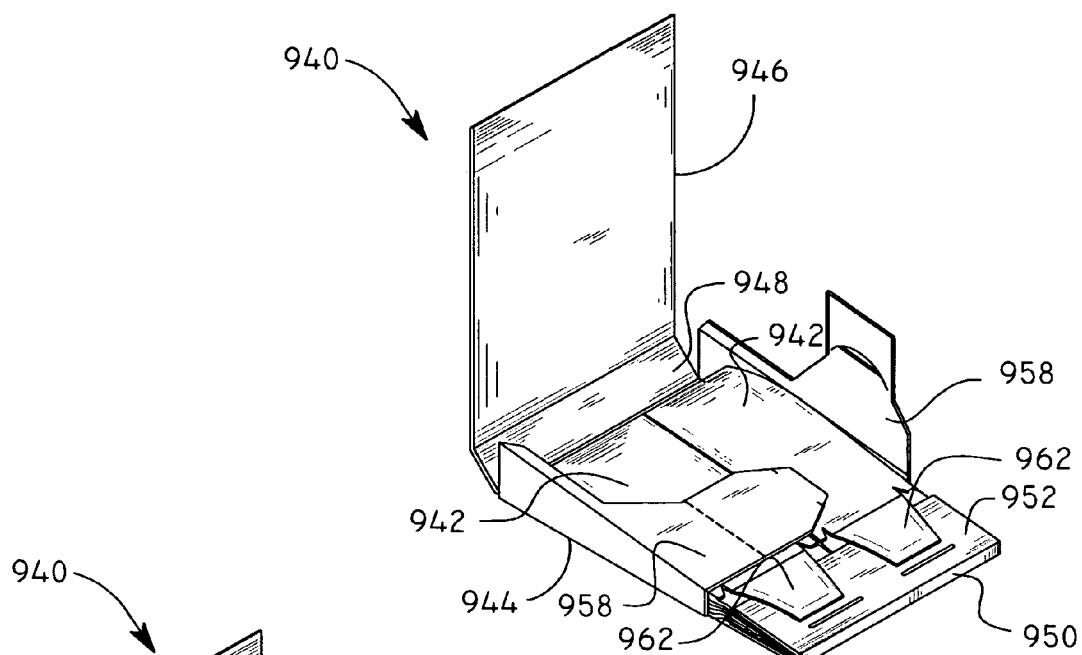
FIG. 36D is a perspective view illustration of the container assembly of FIG. 36A with the front cover and one side member being in a semi-open position.

A perspective view illustration of the container assembly of FIG. 36A with the front cover and one side member being in a semi-open position is shown in FIG. 36D. The front cover 946 and top portion 948 are rotatably located relative to each other and to the back cover 944. Additionally, the front cover is preferably adapted to allow easy access to the first tabs 962. Alternatively, the bandage packages can be reversed so that the first tabs are located proximate to the top portion. The side members are closed using a notched tab design.

Figure 36E:
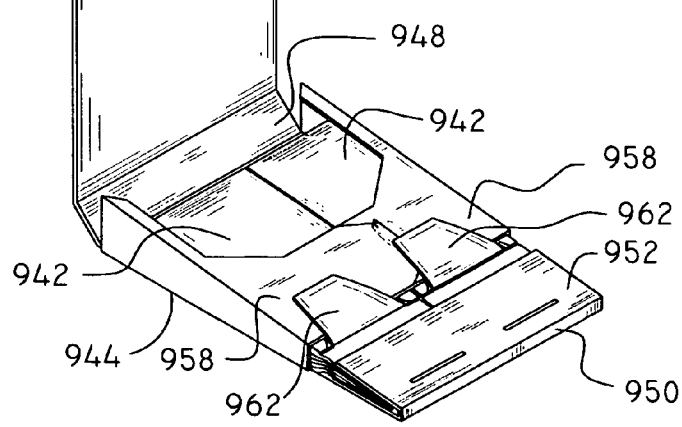
FIG. 36E is a perspective view illustration of the container assembly of FIG. 36A with side members secured to each other and the first tabs folded back over themselves.

A perspective view illustration of the container assembly of FIG. 36A with side members secured to each other and the first tabs folded back over themselves, is shown in FIG. 36E. The first tabs are optionally folded back over themselves prior to closing the package.

Figure 37A:
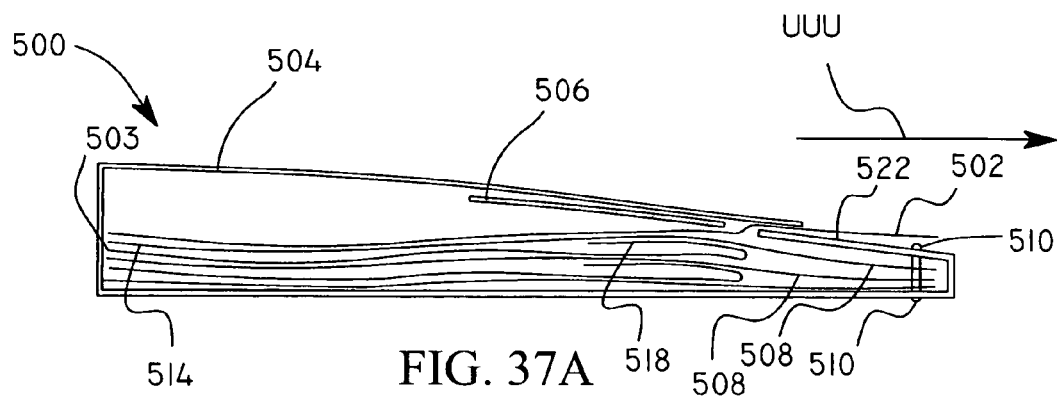
FIG. 37A is a detailed side view illustration of the container assembly of FIG. 36A with the front cover being partially opened and a first tab extending from a package.

A detailed side view illustration of the container assembly of FIG. 36A with the front cover being partially opened and a first tab extending from a package is shown in FIG. 37A. The container assembly 500 holds a dispensing pack. The first tab 502 of the upper most package 501 extends from an opening created by the front cover 504, the side members 506 (which are partially removed so as to shown the dispensing pack contained with the container), and the closure portion 522. Alternatively, when not using the optional side members, the first tab extends from an opening created by the front cover and the closure portion. Alternatively, the first tab extends from an opening created by any other suitable locating means. If using optional side members the front cover can be placed in the fully opened position as the adhesive strips are dispensed from the package.

The second tabs 508 are attached to each other and to the flip cover container using a fastener such as a staple 510 of other suitable means (e.g., adhesives).

In use, the user grasps the first tab of the uppermost package and pulls it away from the dispenser linearly in the direction indicated by arrow UUU.

Figure 37B:
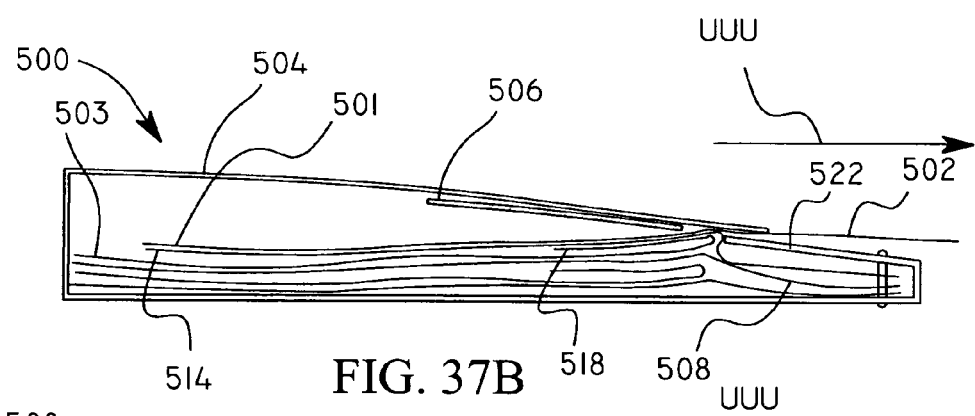
FIG. 37B is a detailed side view illustration of the container assembly of FIG. 37A as the package is opened.

A detailed side view illustration of the container assembly of FIG. 37A as the package is opened is shown in FIG. 37B. Note that for illustration, the following drawings are line drawings, and that the upper sheet is attached to the lower sheet as described elsewhere in this document. The first tab is pulled which causes the package to advance and pass through locating means 512 (which, as depicted, comprises the closure portion and the side member) and also cause at least the lower sheet to fold over itself. The first tab of the successive package 503, which is optionally releasably attached to the lower surface of the lower sheet 514 of the preceding package, begins to fold over itself.

Figure 37C:
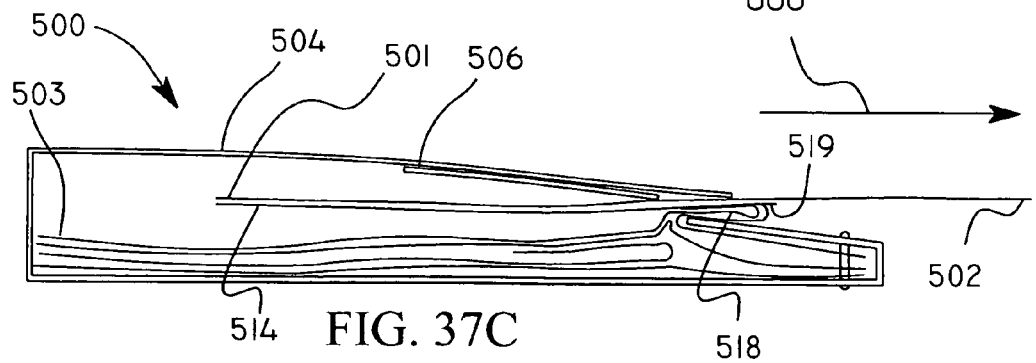
FIG. 37C is a detailed side view illustration of the container assembly of FIG. 37A as the package is opened.

A detailed side view illustration of the container assembly of FIG. 37A as the package is opened is shown in FIG. 37C. The first tab 518 of the successive package is seen unfolding over itself. If the first tab is attached to the adjacent lower sheet of the proceeding package using a low tack adhesive or a cohesive, then the bond between the first tab and the adjacent lower sheet should break as the bandage package is pulled. This effect is desirable in some applications. The leading end of the adhesive strip 519 is partially exposed.

A detailed side view illustration of the container assembly of FIG. 37A as the package is opened is shown in FIG. 37D. The pull cover 513 is seen separating from both the upper sheet and the lower sheet. The adhesive strip 517 is seen peeling away from the release liner 515 and lower sheet. The first tab 518 of the succeeding package has fully folded over itself and is in position for dispensing the next bandage. The bond between the first tab and the lower surface of the lower sheet should be such that the first tab preferably separates from the lower sheet as the first tab is unfolded. Alternatively, the first tab can be separated from the lower sheet when the lower sheet is removed from the dispensing pack, using an adhesive with a low shear force-type bond.

A detailed side view illustration of the container assembly of FIG. 37A as the package is opened is shown in FIG. 37E. The pull cover 513 and the releasably attached adhesive strip 517 have separated from the package. The lower sheet is optionally pulled by the user and separated from the second tab 508 at weakened line 503, thus exposing the first tab of the succeeding package. Alternatively, the lower sheet is pulled against the edge 509 of the closure portion which causes the lower sheet to tear and separate from the dispensing pack. In yet other embodiments, the closure portion includes an edge or other surface to promote separation of the lower sheet.

Other alternative embodiments of the container means are envisioned for use with either the sheet or the roll form dispensing packs as shown and described above. For example, the roll form dispenser can be used in combination with a suitable dispenser such as shown in FIG. 3 of U.S. Pat. No. 5,891,078, to Turngren, entitled "Sterile adhesive bandage and associated methods," incorporated herein by reference in its entirety, or with other suitable roll dispensers as are commonly known in the art.

It should be appreciated that the present invention, either alone, in a dispensing pack, or with a dispensing pack and an optional container, is well suited for use by medical emergency personnel and others such as soldiers and pilots who have limited time to open a conventional package and remove a release liner, especially under urgent conditions or conditions which allow use of only a single hand. In other embodiments, the package may be constructed from waterproof materials so that it does not have to be enclosed in a container to maintain sterility.

The particular materials which may be employed in the practice of this invention are well known in the art. Preferably, the upper and lower sheets are constructed from paper of the same type as is now commonly used to wrap bandages or materials of similar nature. The release liner is preferably constructed from paper which is coated (or treated) on at least one side with a release material, the reverse side being suitable for adhering to the lower sheet. In many embodiments, the bandage itself is known and may be constructed from cloth, plastic, polyester, polyurethane, foam, film, fibrous webs, woven webs, or any other suitable material or any combination thereof.

Moreover, the flexible adhesive strip (or bandage) of the present invention can comprise a hydrocolloidal wound dressing.

Furthermore, the flexible strip may be made from a combination of materials to obtain the desired properties. For example, the flexible strip, the absorbent pad or the adhesive coating on the surface of the flexible strip may be treated so as to possess antimicrobial properties. Such inventions are disclosed in the following: U.S. Pat. No. 4,728,323, to Matson, entitled "Antimicrobial wound dressings," U.S. Pat. No. 4,323,557, to Rosso, et al., entitled "pressure-sensitive adhesive containing iodine," and U.S. Pat. No. 4,310,509, to Berglund, et al., entitled "Pressure-sensitive adhesive having a broad spectrum antimicrobial therein," all of which are incorporated herein by reference in their entirety. In addition, U.S. Pat. No. 5,976,117, to Dunshee, entitled "Wound dressing," incorporated herein by reference in its entirety, discloses a bandage which has at least two regions, one which is proximate to the wound and encourages cell regeneration and provides a space for wound exudates, and a second region which substantially surrounds the first region comprising an antimicrobial agent in an amount that is at least sufficient to inhibit or essentially prevent migration of microorganisms to the first region from the external environment along the interface between the sheet material and the skin to which the sheet material has been adhered. Additionally, the absorbent pad (also known as a wound pad) or the flexible strip may be treated with a medicament or an antimicrobial film. Furthermore, the flexible strip, adhesive strip and/or absorbent pad may be used for transdermal drug delivery or chemical indicators (used for monitoring). It will also be appreciated that the adhesive that is used in adhesive strips and bandages is preferably a dermatologically acceptable pressure-sensitive adhesive. Moreover, the bandages may comprise "smart bandages" which are known in the art.

Furthermore, the flexible strip, adhesive strip, and/or bandage can comprise a film and/or coating which is sensitive to U.V. light and that can change shades or colors when the strip has been exposed to U.V. light which exceeds a given value. The strip is placed on a given location on the users' body (e.g., the hand, neck etc.) or placed on the users' clothing (e.g., a shirt sleeve or glove).

In other alternative embodiments, the dispensing pack, the package, the flexible strip, the adhesive strip, and/or the bandage comprises a flexible power source such as the commonly known POWER PAPER™ (by Power Paper Ltd., Petah Tikva, Israel) is printed upon a desired surface (e.g., a dispensing pack, the package or an adhesive strip or a bandage. An optional alerting means (e.g., a light source, and/or a speaker) is be printed upon, or otherwise attached to, the dispensing pack, the package and/or the flexible strip, adhesive strip and/or bandage. An optional circuit means is coupled to the power source and the light source such that the light source can be activated or deactivated at certain desired times. The circuit means employs an optional activation means such as a passive and/or active switch, a logic means, and/or a timer. A dispensing pack, dispensing package and/or adhesive strip with the alerting means (e.g., a light source or sound source) is useful, when, it is desired that a medical patch be applied at certain desired intervals.

For example, in one embodiment, a dispensing pack with a plurality of packages each incorporating a medical patch is used. A POWER PAPER™ power source is printed upon the dispensing pack and coupled to a circuit means. The circuit means is further coupled to a LED which is in communication with the dispensing pack and is placed in a location such that it is visible to the user. The circuit means employs an optional timer which is optionally activated when the dispensing pack is used for the first time. The timer then causes the circuit means to activate the LED at a desired time period which will alert the user to change medical patches.

Other examples of adhesive strips include a means for securing catheter tubes, etc., or may be made from laminated materials that possess the desired properties.

Throughout this invention, it will be appreciated that the combination formed by the release liner and the releasably attached flexible strip, adhesive strip, or bandage can be folded transversely across its width to minimize the space required by the package as well as the amount of packaging materials used to manufacture the package. If an adhesive strip and attached release liner are folded over then it is preferred that the combination not be too rigid, in order that the bandage can be removed from the package without an undue amount of force. If using a rigidity-enhancing carrier or other laminates upon the adhesive strip, then care should be taken so that the laminates do not delaminate from each other. If using an adhesive strip, then the adhesive strip is preferably folded at or near its midpoint. Alternatively, if using a bandage, then the bandage is preferably folded at a location that is somewhere between the wound pad and the end that is furthest from the leading edge of the bandage (before folding).

The user is further directed to the aforementioned U.S. Pat. Nos. 5,160,315 and 4,472,480, both of which are incorporated herein by reference in their entirety, which describe the selection of release liners and carrier sheets as well as the methods of bonding them to an adhesive strip. Furthermore, the user is directed to the 3M Product Selection Guide, Label Stocks, Laminating Adhesives and Printable Tapes, Mar. 1, 1996. The user is further directed to the Pressure Sensitive Tape Council, Northbrook, Ill., http://www.pstc.org, and to AIMCAL, Fort Mill, S.C., http://www.aimcal.org.

Certain additional advantages and features of this invention may be apparent to those skilled in the art upon studying the disclosure, or may be experienced by persons employing the novel structure of the present package and dispenser, chief of which is that it minimizes the risk of touching and contaminating the absorbent pad. Other advantages are quicker dispensing, easier application, and reduction of the number of individual components requiring disposal.

While the invention has been described with a limited number of embodiments, it will be appreciated that changes may be made without departing from the scope of the original claimed invention, and it is intended that all matter contained in the foregoing specification and drawings be taken as illustrative and not in an exclusive sense.

What is claimed is:

1. An adhesive strip package apparatus, comprising:
   an adhesive strip having an upper surface and a lower surface, said lower surface being releasably attached to a release liner;
   upper and lower sheets attached to each other to form at least part of an enclosure for holding said adhesive strip;
   a weakened area extending at least partially across said package, said weakened area delineating a first tab suitable for grasping;
   said release liner attached to said lower sheet proximate to said first tab;
   an inner tab member releasably attached to said adhesive strip and said first tab; and
   wherein the act of pulling said first tab causes the separation of said release liner from said adhesive strip and the removal of said adhesive strip from said package.

2. The apparatus according to claim 1, further comprising a second tab suitable for grasping and attached to the combination formed by said upper sheet and said lower sheet such that said second tab is located opposite said first tab.

3. The apparatus according to claim 1, wherein said adhesive strip comprises one or more of a bandage and a medical patch.

4. The apparatus according to claim 1, wherein said adhesive strip further comprises a wound pad.

5. An adhesive strip package apparatus, comprising:
   an adhesive strip releasably attached to a release liner;
   upper and lower sheets attached to each other so as to form at least part of an enclosure for holding at least part of said adhesive strip;
   a weakened area extending at least partially across said package and delineating at least part of a first tab suitable for grasping;
   said release liner attached to said lower sheet proximate to said first tab;
   an inner tab member located between said upper and lower sheets and extending across at least part of said weakened area; and
   wherein the act of pulling said first tab causes the separation of said first tab from one or more of said upper sheet and said lower sheet, the separation of said release liner from said adhesive strip, and the removal of said adhesive strip from said package.

6. A package for dispensing adhesive strips, comprising:
   an adhesive strip releasably attached to a release liner;
   a lower sheet;
   an upper sheet attached to said lower sheet so as to form at least part of a cavity for holding said adhesive strip;
   a weakened area extending across said package and defining at least part of a first tab;
   said release liner attached to said lower sheet proximate to said first tab;
   an inner tab member attached to said first tab and releasably attached to said adhesive strip; and
   wherein the act of pulling said first tab causes the separation of said release liner from said adhesive strip and the removal of said adhesive strip from said cavity.

7. The package according to claim 6, wherein said inner tab member extends across at least part of said weakened area when said package is in a closed position.

8. The package according to claim 6, further comprising a second tab located opposite said first tab and suitable for grasping by a user.

9. The package according to claim 6, wherein said inner tab member has a removal tab suitable for grasping by a user.

10. The package according to claim 9, wherein said removal tab is contained within said cavity and is exposed when said adhesive strip is removed from said cavity.

* * * * *